(12) United States Patent
Vo-Dinh et al.

(10) Patent No.: US 8,951,561 B2
(45) Date of Patent: Feb. 10, 2015

(54) METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)

(75) Inventors: Tuan Vo-Dinh, Durham, NC (US); Frederic A. Bourke, Jr., Greenwich, CT (US)

(73) Assignees: Duke University, Durham, NC (US); Immunolight, Detroit, MI (US)

( * ) Notice: Subject to any disclaimer, the term of this patent is extended or adjusted under 35 U.S.C. 154(b) by 667 days.

(21) Appl. No.: 12/389,946

(22) Filed: Feb. 20, 2009

(65) Prior Publication Data

US 2010/0003316 A1    Jan. 7, 2010

Related U.S. Application Data

(60) Provisional application No. 61/030,437, filed on Feb. 21, 2008, provisional application No. 61/080,429, filed on Jul. 14, 2008, provisional application No. 61/042,561, filed on Apr. 4, 2008, provisional application No. 61/035,559, filed on Mar. 11, 2008, provisional application No. 61/080,140, filed on Jul. 11, 2008, provisional application No. 60/954,263, filed on Aug. 6, 2007.

(51) Int. Cl.
| | | |
|---|---|---|
| *A61K 41/00* | (2006.01) | |
| *A61K 9/14* | (2006.01) | |
| *A61K 31/34* | (2006.01) | |
| *A61K 31/35* | (2006.01) | |
| *A61K 31/365* | (2006.01) | |
| *C07D 493/00* | (2006.01) | |
| *A61N 5/06* | (2006.01) | |
| *A61K 39/00* | (2006.01) | |

(52) U.S. Cl.
CPC .............. *A61N 5/06* (2013.01); *A61K 41/0028* (2013.01); *A61K 41/0061* (2013.01); *A61K 41/0066* (2013.01); *A61K 39/00* (2013.01)
USPC .............................. 424/489; 514/455; 549/282

(58) Field of Classification Search
CPC ..... A61K 41/0066; A61K 9/16; A61K 31/34; A61K 31/35; A61K 31/365; C07D 493/00
See application file for complete search history.

(56) References Cited

U.S. PATENT DOCUMENTS

| | | |
|---|---|---|
| 4,111,890 A | 9/1978 | Getson et al. |
| 4,675,346 A | 6/1987 | Lin et al. |
| 4,838,852 A | 6/1989 | Edelson |
| 4,979,935 A | 12/1990 | Lindmayer |
| 5,118,422 A | 6/1992 | Cooper et al. |
| 5,120,649 A | 6/1992 | Horowitz |
| 5,360,734 A | 11/1994 | Chapman et al. |
| 5,489,590 A | 2/1996 | Gulliya et al. |
| 5,521,289 A | 5/1996 | Hainfeld |
| 5,589,590 A | 12/1996 | Ledon et al. |
| 5,728,590 A | 3/1998 | Powell |
| 5,829,448 A | 11/1998 | Fisher |
| 5,957,960 A | 9/1999 | Chen |
| 5,980,954 A | 11/1999 | Bolton |
| 6,036,941 A | 3/2000 | Bottiroli |
| 6,042,603 A | 3/2000 | Fisher et al. |
| 6,051,625 A | 4/2000 | Harkness et al. |
| 6,071,944 A | 6/2000 | Rodgers |
| 6,087,141 A | 7/2000 | Margolis-Nunno |
| 6,121,425 A | 9/2000 | Hainfeld |
| 6,204,058 B1 | 3/2001 | Bolton |
| 6,225,333 B1 | 5/2001 | Rodgers |
| 6,235,508 B1 | 5/2001 | Sowemimo-Coker et al. |
| 6,281,261 B1 | 8/2001 | Bennington |
| 6,323,253 B1 | 11/2001 | Bennington |
| 6,569,467 B1 | 5/2003 | Bolton |
| 6,627,923 B1 | 9/2003 | Lipson et al. |
| 6,669,965 B2 | 12/2003 | Bolton |
| 6,670,113 B2 | 12/2003 | Hainfeld |
| 6,849,058 B1 | 2/2005 | Levy |
| 6,955,639 B2 | 10/2005 | Hainfeld |
| 7,008,559 B2 | 3/2006 | Chen |
| 7,045,124 B1 | 5/2006 | Hamet |
| 7,183,072 B1 | 2/2007 | Hainfeld |
| 7,267,948 B2 | 9/2007 | Vo-Dinh |
| 7,294,656 B2 | 11/2007 | Bach et al. |
| 7,364,872 B1 | 4/2008 | Hainfeld |
| 7,367,934 B2 | 5/2008 | Hainfeld et al. |
| 7,530,940 B2 | 5/2009 | Hainfeld et al. |
| 2002/0127224 A1 | 9/2002 | Chen |

(Continued)

FOREIGN PATENT DOCUMENTS

| | | |
|---|---|---|
| JP | 09038503 | 2/1997 |
| JP | 09299937 | 11/1997 |

(Continued)

OTHER PUBLICATIONS

U.S. Appl. No. 12/417,779, filed Apr. 3, 2009, Bourke, et al.
U.S. Appl. No. 12/401,478, filed Mar. 10, 2009, Bourke, et al.
Opposition issued Jan. 4, 2010 in Chile Application No. 393-2009 (English Translation).
U.S. Appl. No. 13/054,279, filed Jan. 14, 2011, Bourke, et al.

(Continued)

*Primary Examiner* — Ruixiang Li
(74) *Attorney, Agent, or Firm* — Oblon, Spivak, McClelland, Maier & Neustadt, L.L.P.

(57) ABSTRACT

The use of plasmonics enhanced photospectral therapy (PEPST) and exiton-plasmon enhanced phototherapy (EPEP) in the treatment of various cell proliferation disorders, and the PEPST and EPEP agents and probes used therein.

10 Claims, 30 Drawing Sheets

(56) References Cited

U.S. PATENT DOCUMENTS

| | | |
|---|---|---|
| 2003/0022170 A1 | 1/2003 | Khodadoust |
| 2004/0214001 A1 | 10/2004 | Oldenburg et al. |
| 2005/0020869 A1 | 1/2005 | Hainfeld |
| 2006/0067889 A1 | 3/2006 | Pallenberg |
| 2006/0255292 A1 | 11/2006 | Ja |
| 2007/0059316 A1 | 3/2007 | Pallenberg |
| 2007/0063154 A1 | 3/2007 | Chen |
| 2007/0189359 A1 | 8/2007 | Chen et al. |
| 2007/0217996 A1 | 9/2007 | Levy et al. |
| 2007/0218049 A1* | 9/2007 | Chen et al. ............... 424/130.1 |
| 2007/0243137 A1 | 10/2007 | Hainfeld |
| 2007/0274909 A1 | 11/2007 | Justel et al. |
| 2007/0292353 A1 | 12/2007 | Levy et al. |
| 2008/0003183 A1 | 1/2008 | Guo |
| 2008/0039436 A1 | 2/2008 | Patel |
| 2008/0089836 A1 | 4/2008 | Hainfeld |
| 2008/0139993 A1 | 6/2008 | Bensaoula et al. |
| 2008/0248001 A1 | 10/2008 | Bourke |
| 2009/0104212 A1 | 4/2009 | Bourke |

FOREIGN PATENT DOCUMENTS

| | | |
|---|---|---|
| WO | 03/049801 | 6/2003 |
| WO | 2005/030254 | 4/2005 |
| WO | 2006/037081 A2 | 4/2006 |
| WO | 2007/048635 | 5/2007 |
| WO | 2007/108512 | 9/2007 |
| WO | 2008/007290 A2 | 1/2008 |

OTHER PUBLICATIONS

Xiaodong Wang, "The Expanding Role of Mitochondria in Apoptosis", Genes & Development, 15, 2001, pp. 2922-2933, www.genesdev.org (12 pp.).

Reproductive and Cardiovascular Disease Research Group, downloaded from http://www.sgul.ac.uk/depts/immunology/~dash/apoptosis/mito.htm on May 22, 2008, (4pp.).

Noah Scheinfeld, et al., "A Review of Studies that Have Utilized Different Combinations of Psoralen and Ultraviolet B Phototherapy and Ultraviolet A Phototherapy", Dermatology Online Journal, vol. 9, No. 5., downloaded from http://dermatology.cdlib.org/95/reviews/uv/scheinfeld.html on May 22, 2008, (8pp.).

Karen S. McGinnis, et al., "An effective and Synergistic Combined Adjunct to Therapy for Patients with Advances Cutaneous T-Cell Lymphoma", Psoralen Plus Long-Wave UV-A (PUVA) and Bexarotene Therapy, Arch Dermatol., /vol. 139, 2003, pp. 771-775,downloaded from www.archdermatol.com on May 22, 2008, (5pp.).

AB Santamaria et al., "p53 and Fas Ligand are Required for Psoralen and UVA-induces Apoptosis in Mouse Epidermal Cells", Cell Death and Differentiation (200) 9, pp. 549-560, www.nature.com/cdd (12pp.).

Pathak MA., "Mechanism of psoralen photosensitization reactions", Natl Cancer Inst. Monogr, Dec. 1984: 66:41-6, Abstract, downloaded from http://www.ncbi.nlm.nih.gov/pubmed/6531038 on May 22, 2008, (1pp.).

Stanley G. Rockson, et al., "Photoangioplasty: An Emerging Clinical Cardiovascular Role for Photodynamic Therapy", Journal of the American Heart Association, Circulation 2000; 102; pp. 591-596, downloade form http://cir.ahajournals.org/cgi/content/full/102/5/591 on Mar. 26, 2008,(7pp.).

York N. Hsiang et al., "Determining Light Dose for Photodynamic Therapy of Atherosclerotic Lesions in the Yucatan Miniswine", J. Endovasc Surg, 1995, 2, pp. 365-371. (7pp.).

Margaret T. T. Wong-Riley et al., "Photobiomodulation Directly Benefits Primary Neurons Functionally Inactivated by Toxins", The Journal of Biological Chemistry, 2005, vol. 280, No. 6, Issue of Feb. 11. pp. 4761-47771, downloaded form www.jbc.org on Mar. 27, 2008, (11pp.).

Harry Whelan, et al., "Harnessing the Cell's Own Ability to Repair and Prevent Neurodegenerative Disease", Spie, Newsroom, 10.1117/2.1200802.1014, 2008, (3pp.).

Feng Zhang et al., "Channelrhodopsin-2 and Optical Control of Excitable Cells", Nature Methods, vol. 3, No. 10, Oct. 2006, pp. 785-792, http://www.nature.com/naturemethods (8pp.).

H. Wang et al., "High-speed Mapping of Synaptic Connectivity Using Photostimulation in Channelrhodopsin-2 Transgenic mice", PNAS, May 8, 2007, vol. 104, No. 19, pp. 8143-8148, www.pnas.org/cgi/doi/10.1073/pnas.0700384104 (6pp.).

John G. McCarron, et al"Origin and Mechanisms of $Ca^{2+}$ Waves in Smooth Muscle as Revealed by Localized Photolysis of Caged Inositol 1,4,5,-Trisphosphate", The Journal of Biological Chemistry, vol. 279, No. 9, Issue of Feb. 27, pp. 8417-8427, downloaded from http://www.jbc.org on Mar. 5, 2008, (1pp.).

Edward M. Callaway, et al., "Photostimulation Using Caged Glutamate Reveals Functional Circuitry in Living Brain Slices", Proc. Natl. Acad. Sci. USA., vol. 90, Aug. 193, pp. 7661-7665, (5pp.).

S D Zakharov et al, "Light-Oxygen Effect in Cells and its Potential Applications in Tumour Therapy(review", Quantum Electronics 29 (12), 1999, pp. 1031-1053, (23pp.).

Daniel Huber et al., "Sparse Optical Microstimulation in Barrel Cortex Drives Learned Behaviour in Freely Moving Mice", vol. 451, Jan. 3, 2008, doi:10.1038, Nature 06445, Letters (6pp.).

Christopher D. Harvey et al., "Locally Dynamic Synaptic Learning Rules in Pyramidal Neuron Dendrites", vol. 450, Dec. 20/27, 2007, doi:10.1038, Nature 06416, Articles, (8pp.).

Antoine R. Adamantidis et al., "Neural Substrates of Awakening Probed with Optogenec Controll of Hypocretin Neurons", vol. 450, Nov. 15, 2007, doi: 10.1038, Nature 06310, Letters, (6pp.).

N. I. Smith et al., "Photostimulation of Two Types of $Ca^{2+}$ Waves in Rat Pheochoromocytoma PC12 Cells by Ultrashort Pulsed Near-infrated Laser Irradiation", Letters, Wilwy-VCH Verlag GmbH & Co. DGaA, Published Oct. 13, 2005, (8pp.).

Susana W. Lima et al., "Remote Control of Behavior Through Genetically Targeted Photostimulation of Neurons", Resource Department of Cell Biology, Yale University School of Medicine, Cell, vol. 121, Apr. 8, 2005, pp. 141-152, (12pp.).

Matthias Eder et al., "Shining Light on Neurons—Elucidation of Neuronal Functions by Photostimulation", Clinical Neuropharmacology, Max-Planck-Institute of Psychiatry, Munich, Germany, Reviews in the Neurosciences, 15, 2004, pp. 167-183, (16pp.).

Katleen Braet et al., "Photoliberating Inositol-1,4,5-Trisphosphate Triggers ATP Release That is Blocked by the Connexin Mimetic Peptide Gap 26", Churchill Livingstone, Cell Calcium 33, 2003, pp. 37-48, (12pp.).

Karel Svoboda, "New Studies Illuminate the Computational Power of Neurons", HHMI, Research News, Dec. 20, 2007, (3pp.).

Photobiomodulation, Wikipedia, downloaded from http://en.wikipedia.org/wiki/Laser_therapy on Mar. 26, 2008, (2pp.).

Science News, "Pulsing Light Silences Overactive Neurons", ScienceDaily, Mar. 28, 2007, downloaded from http://sciencedaily.com/releases/2007/03/070327161418.htm on Mar. 26, 2008, (2pp.).

Science News, Scientist Directly Control Brain Cell Activity With Light, ScienceDaily, Apr. 5, 2007, downloaded from http://www.sciencedaily.com/releases/2007/04/070704162400.htm on Mar. 26, 2008, (2pp.).

ScienceDaily, Optical Technique Studies Brain Activity without Surgery on Skull, Aug. 2, 2001 Champaign, III, downloaded from http://www.sciencedaily.com/releases/2001/08/010802081211.htm on Mar. 26, 2008, (2pp.).

Jay Motola, "Enlarged Prostate Treatment: Green Light PVP", ProstateCommons.com, Monday, Nov. 5, 2007, downloaded from http://healthcentral.com/prostate/c/95/15917/gree-light-pvp/ on Mar. 26, 2008, (2pp.).

Judy Foreman, "What is'Green Light' Laser Therapy to Treat an enlarged Prostate?", The Boston Globe, Health Answere, Sep. 3, 2007, downloaded form http://.boston.com/news/golbe/health_science/articles/2007/09/03/what_is_green_light, on Mar. 26, 2008, (2pp.).

Prof. Tiina Karu's, "Cellular Mechanism of Low-Power Laser Therapy", Photobiomodulation, downloaded from www.tinnitus.us/tiinakarupresentaion.html on Mar. 26, 2008, (6pp.).

Pascal Carmody Medical Director, "Photodynamic Therapy", The Photodynamic Treatment Center at East Clinic, Killaloe, Co. Clare,

(56) References Cited

OTHER PUBLICATIONS

Ireland, http://www.famma.ru/technical/articles-1/photodynamic_therapy.htm downloaded on Mar. 26, 2008, (4pp.).
William E. Grant, et al., "Photodynamic Therapy of Arteries: Preservation of Mechanical Integrity", Photodynamic Therapy of Arteries: Preservation of Mechanical Integrity, http://www.lumacare.com/paper6.htm downloaded on Mar. 26, 2008, (6pp.).
S D Zakharov et al., Light-Oxygen Effect in Cells and its Potential Applications in Tumor Therapy (review), Quantum electron 29, pp. 1031-1053, 1999, Abstract, http://www.iop.org/EJ/abstract/1063-7818/29/12/r03, downloaded on Mar. 26, 2008,(1pp.).
Zhang F. et al., "Multimodal Fast Optical Interrogation", Comment in Nature Apr. 5, 2007; 446 (7136):617-9, Abstract, (1pp.).
Marleny Elizabeth Marquez Martinez et al., "Effect of IR Laser Photobiomodulation on the Repair of Bone Defect Grafted with Organic Bovine Bone", Journal Lasers in Medical Science, Springerlink Date, Thursday, Sep. 20, 2007, Abstract, (2pp.).
Yasuyuki Nemota et al., "Inductive and Inhibitory Effects of Light on Cell Division in Chattonella Antigua", Plant and Cell Physiology, Oxford Journals, vol. 26, No. 4, pp. 669-674, Abstract, downloaded from http://pcp.oxfordournals.org/cgi/content/abstract/26/4/669 on Mar. 26, 2008, (1pp.).
Arany PR. et al., "Activation of Latent TGF-beta1 by Low-Power Laser in Vitro Correlates with Increased TGF-beta 1 Levels in Laser-enhanced Oral Wound Healing", Wound Repair Regen, Nov.-Dec. 2007;15(6):866-74, Abstract, (1pp.).
Lopes CB. et al., "Infrared Laser Photobiomodulation (lambda 830 nm) on Bone Tissue Around Dental Implants: a Raman Spectroscopy and Scanning Electronic Microscopy Study in Rabbits", Photomed Laser Surg. Apr. 2007, 25(2):96-101, Abstract, (1pp.).
Kim KH, et al., "Laser Lipolysis Using a Novel 1,064nm Nd:YAG Laser", Dermatol Surg. Feb. 2006; 32(2) :241-48; discussion 247, (1pp.).
Kim HS, et al., "Endovenous Laser Ablation of the Great Saphenous Vein with a 980-nm Diode Laser in Continuous Mode: Early Treatment Failures and Successful Repeat Treatments", Comment in: J. Vasc. Interv Radiol, Jun. 2007; 18(6):811; Author Reply 812-3, (2pp.).
Heinrich E., et al, "Technique and Short-Term Outcome of Green Light Laser (KTP, 80w) Vaporisation of the Prostate", Eur Urol. Dec. 2007;52 (6):1632-7. Epub July 31, 2007 (1pp.).
Liu, Timon et al., "Photobiomodulation: Phenomenology and its Mechanism" (c) 2005; SPIE—The International Society for Optical Engineering, Abstract, downloaded from http://adsabs.harvard.edu/abs/2005SPIE.5630..185L on Mar. 26, 2008 (1pp.).
Han X, et al., "Multiple-color Optical Activation, Silencing, and Desynchronization of Neural Activity with Single-Spike Temporal Resolution", PLoS One, Mar. 21, 2007; 2(3):e299, Abstract, downloaded form www.ncbi.nlm.nih.gov on Apr. 2, 2008, (1pp.).
N.I.Smith et al., "Photostimulation of Two Types of $Ca^{2+}$ Waves in Rat Pheochoromocytoma PC12 Cells by Ultrashort Pulsed Near-Infrared Laser Irradiation", Laser Physics Letters, vol. 3, Issue 3, pp. 154-116, pulbished online Oct. 13, 2005, downloaded from http://www.3.interscience.wiley.com on Mar. 4, 2008, Abstract, (1pp.).
Katz LC, et al., "Scanning Laser Photostimulation: A New Approach for analyzing Brain Circuits", J. Neurosci Methods, Oct. 1994;54 (2):205-18, Abstract, downloaded from http://www.ncbi.nlm.nih.gov/pubmed/7869753 on Mar. 4, 2008, (1pp.).
Cha-Min Tang, "Unit 6.21 Photolysis of Caged Neurotransmitters: Theory and Procedures for Light Delivery", InterScience, Baltimore VA Medical Center and University of Maryland School of Medicine, Abstract, 2006, (1pp.).
Godwin DW, et al., "Photostimulation with Caged Neurotransmitters Using Fiber Optic Lightguides", J. Neurosci Methods, Apr. 25, 1997;73(1):91-106, Abstract, http://www.ncbi.nlm.nih.gov/pubmed/9130682, (1pp.).
Kadir Asian et al., "Multicolor Microwave-Triggered Metal-Enhances Chemiluminescence", JACS Communication, J. Am. Chem. Soc., online published Sep. 23, 2006, (6pp.).

F.V. Santos et al., "Photocatalysis as a Tertiary Treatment for Petroleum Refinery Wastewaters", Brazilian Journal of Chemical Engineering, vol. 23, No. 04, Oct.-Dec. 2006, pp. 451-460, www.abeq.org.br/bjche, (10pp.).
Mai Thu Thi Tran et al., "Ultraviolet Treatment of Orange Juice", Elsevier, Innovative Food Science and Emerging Technologies 5 (2004), pp. 495-502, www.s.sciencedirect.com, (8pp.).
M. Thoms[a0] et al., "Method for the determination of Photostimulable defect Center Concentrations, Production Rates, and Effective Formation Energies", J. Appl. Phys. 75 (9), May 1, 1994, (4pp.).
Surbhi Lal et al., "Nano-optics from Sensing to Waveguiding", Review Article, Nature Photonics, vol. 1, Nov. 2007, pp. 641-648. www.nature.com/naturephotonics, (8pp.).
Mustafa H. Chowdhury et al., "Metal-Enhanced Fluorescence of Phycobiliprotein from Heterogeneous Plasmonic Nanostructures", J. Phys. Chem. C 2007, 111, pp. 18856-18863, Articles, (8pp.).
Harry A. Atwater, "The Promise of Plasmonics", Scientific American, published Apr. 2007, www.sciam.com, (8pp.).
Stefan A. Maier, "Plasmonic Field Enhancement and SERS in the Effective Mode Volume Picture", Optics Express, Mar. 6, 2006/ vol. 14, No. 5, pp. 1957-1964, (8pp.).
DE Bary Aqua—UV, "Sterilizers for Frest or Marine Water Aquarium, Garden Ponds, Breeder Tanks and Commercial Applications in the Molluscan Shellfish Industry", Info. A4-GB-Nov. 2002, (4pp.).
Loctite, Light, Cure, Technology, Loctite Americas 2000, Technical Manual www.loctite.com, (24pp.).
Dr. Roger McCartney, Consultant, Fusion UV Systems, Inc., "UV Cocooning: CMTI Emissions Testing Results", Composites 2002 Convention and Trade Show Composites Fabricators Association, Sep. 25-27, 2002, Atlanta, Georgia USA, (11pp.).
Aaron P. VanDevender el al., "Quantum Transduction Via Frequency Upconversion" (Invited), J. Opt. Soc. Am., vol. 24, No. 2, Feb. 2007, pp. 295-297, (5pp.).
Aslan Kadir et al., "Fast and Sensitive DNA Hybridization Assays Using Microwave-accelerated Metal-enhanced Fluorescence", ScienceDirect, Biochemical and Biophysical Research Communications 348 (2006) pp. 612-617, www.sciencedirect.com, (6pp.).
Shaomin Wang et al., "Electromagnetic Excitation of Nano-carbon in Vacuum", Optics Express, May 16, 2005, vol. 13, No. 10, 3625, (6pp.).
Kadir Aslan et al., "Microwave-Accelerated Metal-Enhanced Fluorescence (MAMEF) with Silver Colloids in 96-well Plates: Application to Ultra Fast and Sensitive Immunoassays, High Throughput Screening and Drug Discovery", Journal of Immunological Method 312 (2006) pp. 137-147, (11pp.).
David J. Hurrell, Sterilization, "Recent Developments in Sterilization Technology", Medical Device Link, The Online Information Source for the Medical Device Industry, Medical Plastics and Biomaterials Magazine PB Article Index, published Sep. 1998, downloaded from http://www.devicelink.com/mpb/archive/98/09/002.html, on May 19, 2008, (8pp.).
"Viral Inactivation of Blood Products", Transfusion, The Journal of the American Association of Blood Banks, vol. 30, Jul./Aug. 1990, No. 6, (3pp.).
N. Elmnasser et al., "Pulsed-light System as a Novel Food Decontamination Technology: a Review", Can. J. Microbiol., 53, (2007), pp. 813-821, (9pp.).
Parmeswaran Diagaradjane et al., "Modulation of in Vivo Tumor Radiation Response Via Gold Nanoshell-Mediated Vascular_Focused Hyperthermia: Characterizing an Integrated Antihypoxic and Localized Vascular Disrupting Targeting Strategy", Nano Letters, 2008, vol. 8, No. 5, 1492-1500, (9PP.).
Marino A. Campo et al., "Polymeric Photosensitizer Prodrugs for Photodynamic Therapy" Photochemistry and Photobiology, 2007, 83, pp. 958-965, (8PP.).
Competitive Binging Data with one Class of Receptors, Fitting data to a one-site competitive binding curve, http://www.graphpad.com/curvefit/one_kind_of_receptor.htm, 1999, (3pp.).
Jacky Lyden, "Good Vibrations Emanate from Nanotube", NPR, Nov. 5, 2007, downloaded from http://www.npr.org/templates/story/story.php?storyId=15868800 on Nov. 5, 2007, (5pp.).

(56) References Cited

OTHER PUBLICATIONS

Martina E. Wieder et al., "Intracellular Photodynamic Therapy with Photosensitizer-nanoparticle Conjugates: Cancer Therapy Using a 'Trojan horse'", The Royal Society of Chemistry and Owner Societies, Photochemical & Photobiol.1 Sci., 2006, 5, pp. 727-734, www.rsc.org/pps, (8pp.).
Xiaohue Huang et al., "Plasmonic Photothermal Therapy (PPTT) Using Gold Nanoparticles", Review Article, Laser Med. Sci., 2007, (12pp.).
Ernst Wagner, "Programmed Drug Delivery: Nanosystems for Tumor Targeting", Editorial, Expert Opinion Biol. Ther. 2007, 7(5), pp. 587-593, (7pp.).
Giuseppe Palumbo, "Photodynamic Therapy and Cancer: a Brief Sightseeing Tour", Review, Expert Opinion, Drug Deliv. 2007, 4(2), pp. 131-148, (18pp.).
Sehoon Kim et al., "Organically Modified Silica Nanoparticles Co-encapsulating Photosensitizing Drug and Aggregation—Enhances Two-Photon Absorbing Fluorescent Dye Aggregates for Two-Photon Photodynamic Therapy", JACS Articles, J. Am. Chem. Soc., vol. 129, No. 9, 2007, (8pp.).
Ivan Charamisinau et al., "Semiconductor Laser Insert with Uniform Illumination for Use in Photodynamic Therapy", Applied Optics, Aug. 20, 2005, vol. 44, No. 24, pp. 5055-5068, (14pp.).
Brian M. Caullum, "Smart Medical and Biomedical Sensor Technology", Spie Proceeding Series—The International Society for Optical Engineering, vol. 5261, Oct. 28-29, 2003, (14pp.).
Akimichi Morita et al, "Evidence that Singlet Oxygen-Induced Human T. Helper Cell Apoptosis is the Basic Mechanism of Ultraviolet-A Radiation Phototherapy", Brief Definitive Report, J. Exp. Med., vol. 186, No. 10, Nov. 17, 1997, pp. 1763-1768, downloaded from http://www.jem.org on Sep. 6, 2007, (6pp.).
M. F. Nichols et al., "Oxygen Diffusion and Reaction Kinetics in the Photodynamic Therapy of Multicell Tumour Speroid", Phys. Med. Biol. 39, 1994, 2161-2181, (21pp.).
H. Peter Van Iperen et al., "Singlet Oxygen Producing Photosensitizers in Photophoresis", Journal of Photochemistry and Photobiology B: Biology 38, 1997, pp. 203-208, (6pp.).
Irene Georgakoudi et al."The Mechanism of Photofrin © Photobleaching and Its Consequences for Photodynamic Dosimetry", Photochemistry and Photobiology, 1997, 65(1), pp. 135-144, 10pp.).
Brian W. Pogue et al.,"A Photobiological and Photophysical-based Study of Phototoxicity of Two Chlorins[1]", Cancer Research 61, Jan. 15, 2001, pp. 717-724, (8pp.).
Wei Chen et al., "Using Nanoparticles to Enable Simultaneous Radiation and Photodynamic Therapies for Cancer Treatment", J. Nanoscience Nanotechnology, 2006, vol. 6, No. 4, pp. 1159-1166, (8pp.).
Junkoh Yamamoto et al., "Monitoring of Singlet Oxygen Is Useful for Predicting the Photodynamic Effects in the Treatment for Experimental Glioma", Clin Cancer Res 2006: 12(23) Dec. 1, 2008, pp. 7132-7139, www.aacrjournals.org, (10pp.).
Jurgen Baier et al, "Direct Detection of Singlet Oxygen Generated by UVA Irradiation in Human Cells and Skin", Original Article, Journal of Investigative Dermatology, 2007, vol. 127, pp. 1498-1506, (9pp.).
Timothy C. Zhu, "Modeling of Singlet Oxygen During Photodynamic Therapy Using COMSOL Multiphysics", Expert from the Proceedings of the COMSOL Users Conference 2006 Boston, (5pp.).
Fernando L. Primo et al., "Magnetic Nanoemulsions as Drug Delivery System for Foscan : Skin Permeation and retension in Vitro Assays for Topical Application in Photodynamic Therapy (PDT) of Skin Cancer", Journal of Magnetism and Magnetic Materials 311, (2007), pp. 354-357, available online at www.sciencedirect.com, (5pp.).
Harry A. Atwater, "The Promise of Plasmonics, a Technology the Squeezed Electromagnetic Waves into Minuscule Structures May Yield a New Generation of Superfast Computer Chips and Ultrasensitive Molecular Detectors", Scientific American Magazine—Mar. 18, 2007, http://www.sciam.com/arlicle.cfm?id=the-promise-of-plasmonics&pring=true, (4pp.).
Carraro C, Pathak MA., "Studies on the Nature of In Vitro and In Vivo Photosensitization Reactions by Psoralens and Porphyrins", J. Invest Dermatol. 1988, Mach 90(3) pp. 267-275, Abstract, (1pp.).
Paul D. Wood et al., "Reactions of Psoralen Radical Cations with Biological Substrates", Photochemistry and Photobiology, Article, pp. 155-162 (Abstract), Bioone Online Journal Access Control, vol. 72, Jun. 2008, http://www.bioone.org/perlserv, 1pp.).
Reynel Cancio et al., "High Potency of Indolyl Aryl Sulfone non-nucleoside Inhibitors Towards Drug-Resistant Human Immunodeficiency Virus Type 1 Reverse Transcriptase Mutants Is Due to Selective Targeting of Different Mechanistic Form of the Enzyme", Antimicrobial Agents and Chemotherapy,vol. 49, No. 11, Nov. 2005, pp. 4546-4554 downloaded from aac.asm.org on Oct. 17, 2007, (9pp.).
Jacek Bartkowiak et al.,"Selective Displacement of Nuclear Proteins by Antitumor Drugs Having Affinity for Nucleic Acids", Proc.Natl. Acad.Sci. vol. 86, pp. 5151-5154, Jul. 1989, Medical Sciences, Abstract, (1pp.).
Sylvie Giacchetti et al., "Phase III Trial Comparing 4-Day Chronomodulated Therapy Versus 2-Day Conventional Delivery of Fluorouracil, Leucovorin, and Oxaliplatin As First-Line Chemotherapy of Metastatic Colorectal Cancer: The European Organisation for Research and Treatment of Cancer Chronotherapy Group", Journal of Clinical Oncology, Original Report, vol. 24, No. 22, Aug. 1, 2008, (8pp.).
Fr G. McConnell, "Visit to Lassie (Apr. 2008): Initiating an International Colaboration to Develop Laser Sources for Spatially-Localised, Deep-Tissue Photostimulation", University of Strathclyde, Centre for Biophotonics, EPSRC Reference: EP/F036213/1, EPDRC, http://gow.epsrc.ac.uk/ViewGrant.aspx?GrantRef=EP/F036213/1 (2pp.).
K. Jensen, J. Weldon, H. Garcia, and A. Zettl, "Nanotube Radio," *Nano Lett.*, vol. 7, No. 11, 3508-3511 (2007).
Douglas D. Young and Alexander Deiters, "Photochemical Hammerhead Ribozyme Activation", *Bioorganic & Medicinal Chemistry Letters*, 16(10),pp. 2658-2661 (2006).
Hirsch, L.R., Stafford, R.J., Bankson, J.A., Sershen, S.R., Rivera, B., Price, R.E., Hazle, J. D., Halas, N. J., and West, J. L., *Nanoshell-mediated near-infrared thermal therapy of tumors under magnetic resonance guidance*. PNAS, 2003. 100(23): p. 13549-13554.
Xiaohua Huang & Prashant K. Jain & Ivan H. El-Sayed & Mostafa A. El-Sayed, Plasmonic photothermal therapy (PPTT) using gold nanoparticles, *Lasers in Medical Science*, Aug. 2007.
Mircea Cotlet, Tom Vosch, Satoshi Habuchi, Tanja Weil, Klaus Mullen, Johan Hofkens, and Frans De Schryver, "*Probing Intramolecular Forster Resonance Energy Transfer in a Naphthaleneimide-Peryleneimide-Terrylenediimide-Based Dendrimer by Ensemble and Single-Molecule Fluorescence Spectroscopy*", J. Am. Chem. Soc. 2005, 127, 9760-9768.
M.O. Guler, "Singlet-Singlet and Triplet-Triplet Energy Transfer in Bichromophoric Cyclic Peptides," Worcester Polytechnic Institute, May 18, 2002.
Young and Deiters in "Photochemical Control of Biological Processes", *Org. Biomol. Chem.*, 5, pp. 999-1005 (2007).
T. Vo-Dinh, M.Y.K. Hiromoto, G. M. Begun and R. L. Moody, "Surface-enhanced Raman spectroscopy for trace organic analysis," *Anal. Chem.*, vol. 56, 1667, 1984.
M. M. Kerker, Electromagnetic Model for Surface-Enhanced Raman Scattering (SERS) on Metal Colloids, *Acc. Chem. Res.*, 17, 370 (1984).
T. Vo-Dinh, "Surface-Enhanced Raman Spectroscopy Using Metallic Nanostructures," *Trends in Anal. Chem.*, 17,557 (1998).
J. B. Jackson, S. L. Westcott, L. R. Hirsch, J. L. West and N. H. Halas, "Controlling the surface enhanced Raman effect via the nanoshell geometry," *Appl. Phys. Lett.*, vol. 82, 257-259, 2003.
S. J. Norton and T. Vo-Dinh, "Plasmonic Resonances of nanoshells of Spheroidal Shape", *IEEE Trans. Nanotechnology*, 6, 627-638 (2007).
R. Elghanian, J.J. Storhoff, R.C. Mucic, R.L. Letsinger and C.A. Mirkin, Selective colorimetric detection of polynucleotides based on the distance-dependent optical properties of gold nanoparticles. *Science* 277 (1997), pp. 1078-1081.

(56) References Cited

OTHER PUBLICATIONS

Z. Li, R.C. Jin, C.A. Mirkin and R.L. Letsinger, Multiple thiol-anchor capped DNA-gold nanoparticle conjugates. *Nucleic Acids Res.* 30 (2002), pp. 1558-1562.

Y.W. Cao, R. Jin and C.A. Mirkin, DNA-modified core-shell Ag/Au nanoparticles. *J. Am. Chem. Soc.* 123 (2001), pp. 7961-7962.

Burgess, J. D.; Hawkridge, F. M., "*Octadecyl Mercaptan Submonolayers on Silver Electrodeposited on Gold Quartz Crystal Microbalance Electrodes*", Langmuir 1997, 13, 3781-6.

Hainfeld et al, Gold nanoparticles: a new X-ray contrast agent, *The British Journal of radiology*, 79, 248, 2006.

Ma et al, DNA-Passivated CdS Nanocrystals : Luminescence, Bioimaging, and Toxicity Profiles, *Langmuir*, 23 (26), 12783-12787 (2007).

Hua et al, Soft x-ray excited optical luminescence : Some recent applications, *Rev. Sci. Instrum.,*, 73, 1379, 2002.

Jaegle et al, Ultraviolet luminescence of CsI and CsCl excited by soft x-ray laser, *J. Appl. Phys.*, 81, 2406, 1997.

Kun Chen, Yang Liu, Guillermo Ameer, Vadim Backman, Optimal design of structured nanospheres for ultrasharp light-scattering resonances as molecular imaging multilabels, *Journal of Biomedical Optics*, 10(2), 024005 (Mar./Apr. 2005).

Mirkhin et al, X-ray excited luminescence of some molybdates, *Nuclear Instrum. Meth. In Physics Res. A*, 486, 295 (2002).

L. Soderholm, G. K. Liu, Mark R. Antonioc, F. W. Lytle, X-ray excited optical luminescence .XEOL. detection of x-ray absorption fine structure .XAFZ, *J. Chem. Phys*, 109, 6745, 1998.

Masashi Ishiia, Yoshihito Tanaka and Tetsuya Ishikawa, Shuji Komuro and Takitaro Morikawa, Yoshinobu Aoyagi, Site-selective x-ray absorption fine structure analysis of an optically active center in Er-doped semiconductor thin film using x-ray-excited optical luminescence, *Appl. Phys. Lett*, 78, 183, Jan. 8, 2001.

Kuiru Li, Mark I. Stockman, and David J. Bergman, Self-Similar Chain of Metal Nanospheres as an Efficient Nanolens, *Physical Review Letter*, vol. 91, No. 22, 227402-1, 2003.

Frens, G., *Controlled nucleation for the regulation of the particle size in monodisperse gold solutions.* Nature (London) Phys Sci 1973. 241: p. 20-22.

Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, vol. 101, 1719-1729, 2007.

Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, vol. 35 (2006), No. 10 p. 1192.

Martin Nikl, Scintillation detectors for x-rays, *Meas. Sci. Technol.* 17 (2006) R37-R54.

Kadshchuk, A. K., Ostapenko, N. I., Skryshevskii, Yu. A., Sugakov, V. I. and Susokolova, T. O., Clusters of Dipole Charge-Carrier Capture Centers in Organic Crystals, *Mol. Cryst. and Liq. Cryst.*, 201, 167 (1991) t.

S. V. Izvekov, V. I. Sugakov, Exciton and Electron Traps on Structural Defects in Molecular Crystals with Dipolar Molecules, *Physica Scripta.* vol. T66, 255-257, 1996.

A. P. D'Silva, G. J. Oestreich, and V. A. Fassel, X-ray excited optical luminescence of polynuclear aromatic hydrocarbons, *Anal. Chem.*; 1976; 48(6) pp. 915-917.

T. Vo-Dinh, Multicomponent analysis by synchronous luminescence spectrometry, *Anal. Chem.*; 1978; 50(3) pp. 396-401.

J. Bellessa, C. Bonnand, and J. C. Plenet, J. Mugnier, Strong Coupling between Surface Plasmons and Excitons in an Organic Semiconductor, *Phys. Rev. Lett*, 93 (3), 036404-1, 2004.

Alexander O. Govorov, Garnett W. Bryant,‡ Wei Zhang, Timur Skeini, Jaebeom Lee, § Nicholas A. Kotov, Joseph M. Slocik,| and Rajesh R. Naik, Exciton-Plasmon Interaction and Hybrid Excitons in Semiconductor-Metal Nanoparticle Assemblies, *Nano Lett.*, vol. 6, No. 5, 984, 2006.

I.V. Bondarev, K. Tatur and L.M. Woods, *Strong exciton-plasmon coupling in semiconducting carbon nanotube*, Jul. 8, 2009 Accepted paper in Physical Review B.

Yuri Fedutik, Vasily Temnov, Ulrike Woggon, Elena Ustinovich, and Mikhail Artemyev, Exciton-Plasmon Interaction in a Composite Metal-Insulator-Semiconductor Nanowire System, *J. . Am. Chem. Soc.*, 129 (48), 14939-14945, 2007.

G.W. Ford and W. H. Weber, Electromagnetic interactions of molecules with metal surfaces, *Phys. Rep.* 113, 195-287 (1984).

Gregory A. Wurtz, Paul R. Evans, William Hendren, Ronald Atkinson, Wayne Dickson, Robert J. Pollard, and Anatoly V. Zayats, Molecular Plasmonics with Tunable Exciton-Plasmon Coupling Strength in J-Aggregate Hybridized Au Nanorod Assemblies, *Nano Lett.*, vol. 7, No. 5, 1297, 2007.

Jaebeom Lee, Alexander O. Govorov, John Dulka, and Nicholas A. Kotov, Bioconjugates of CdTe Nanowires and Au Nanoparticles: Plasmon-Exciton Interactions, Luminescence Enhancement, and Collective Effects, *Nano Lett.*, vol. 4, No. 12, 2323, 2004.

N.R. Jana, L. Gearheart and C.J. Murphy, Seeding growth for size control of 5-40 nm diameter gold nanoparticles. *Langmuir* 17 (2001), pp. 6782-6786.

Brust, M.; Walker, M.; Bethell, D.; Schiffrin, D. J.; Whyman, R., *Synthesis of Thiol-derivatised Gold Nanoparticles in a Two-phase Liquid-Liquid System Chem. Commun.* 1994, 801.

Hostetler, M.J.; Wingate, J. E.; Zhong, C. J.; Harris, J. E.; Vachet, R. W.; Clark, M. R.; Londono, J. D.; Green, S. J.; Stokes, J. J.; Wignall, G. D.; Glish, G. L.; Porter, M. D.; Evans, N. D.; Murray, R. W., Alkanethiolate Gold Cluster Molecules with Core Diameters from 1.5 to 5.2 nm: Core and Monolayer Properties as a Function of Core Size, *Langmuir* 1998, 14, 17.

Schmid, G.; Pfeil, R.; Boese, R.; Bandrmann, F.; Meyer, S.; Calis, G. H. M.; van der Velden, J. W. A., $Au_{55}[P(C_6H_5)_3]_{12}Cl_6$-ein Goldcluster ungewohnlicher Größe, *Chem. Ber.* 1981, 114, 3634; with English Abstract.

Warner, M. G.; Reed, S. M.; Hutchison, J. E., Small, Water-Soluble, Ligand-Stabilized Gold Nanoparticles Synthesized by Interfacial Ligand Exchange Reactions, *Chem. Mater.* 2000, 12, 3316.

Weare, W. W.; Reed, S. M.; Warner, M. G.; Hutchison, J. E., Improved Synthesis of Small ($d_{CORE}$≈1.5 nm) Phosphine-Stabilized Gold Nanoparticles, *J. Am. Chem. Soc.* 2000, 122, 12890.

Ziyi Zhong, Benoit Male, Keith B. Luong, John H.T., More Recent Progress in the Preparation of Au Nanostructures, Properties, and Applications, *Analytical Letters*; 2003, vol. 36 Issue 15, p. 3097-3118.

Akito Masuhara, Satoshi Ohhashi, Hitoshi Kasai; Shuji Okada, Fabrication and Optical Properties of Nanocomplexes Composed of Metal Nanoparticles and Organic Dyes, *Journal of Nonlinear Optical Physics & Materials* vol. 13, Nos. 3 & 4 (2004) 587-592.

Wang et al. In "Electromagnetic excitation of nano-carbon in vacuum," in Optics Express, vol. 13, No. 10, May 10, 2005.

Aslan et al. In "Multicolor Microwave-Triggered Metal-Enhanced Chemiluminescence," in J. Am. Chem. Soc. published on Web Sep. 23, 2006.

M. A. Correa-Duarte, M. Giesig, and L. M. Liz-Marzan, *Stabilization of CdS semiconductor nanoparticles against photodegradation by a silica coating procedure*, Chem. Phys. Lett., 1998, 286: 497.

M. Thoms, H. von Seggern, *Method for the determination of photostimulable defect center concentrations, production rates, and effective formation energies*, J. Appl. Phys. 1994, 75: 4658-4661.

W. Chen, S. P. Wang, S. Westcott, J. Zhang, A. G. Joly, and D. E. McCready, Structure and luminescence of $BaFBr:Eu^{2+}$ and $BaFBr:Eu^{2+}$, $Tb^{3+}$ phosphors and thin films, J. Appl. Phys. 2005, 97: 083506.

Mai Thu Thi Tran, Mohammed Farid, "Ultraviolet Treatment of Orange Juice" published in Innovative Food Science & Emerging Technologies (vol. 5, Issue 4, Dec. 2004, pp. 495-502).

Santos et al, *Photocatalysis as a Tertiary Treatment for Petroleum Refinery Wastewaters*, Braz. J. Chem. Eng. vol. 23, No. 4, 2006.

Spatio-Resolved Hyperbranched Graft Polymerized Surfaces by Iniferter-Based Photograft Copolymerization, *Langmuir*, 2002, 18 (7), pp. 2601-2606.

(56) References Cited

OTHER PUBLICATIONS

Pettinger B., U. Wenneng, and H. Wetzel, Surface-plasmon enhanced Raman-scattering Frequency and Angular Resonance of Raman Scattered Light From Pyridine on Au, Ag and Cu Electrodes, 1980, Surf. Sci., 101, 409.

Fleishman M., P. R. Graves, and J. Robinson, *The Raman-Spectroscopy of the Ferricyanide/Ferrocyanide System at Gold, β-Palladium Hydride and Platinum Electrodes*, 1985, J. Electroanal. Chem., 182, 87.

Miller S. K., A. Baiker, M. Meier, and A. Wokaun, *Surface-enhanced Raman scattering and the preparation of copper substrates for catalytic studies*, 1984, J. Chem. Soc. Farad. Trans. I, 80, 1305.

Taranenko N., J.P. Alarie, D.L. Stokes, and T. Vo Dinh, *Surface-Enhanced Raman Detection of Nerve Agent Simulant (DMMP and DIMP) Vapor on Electrochemically Prepared Silver Oxide Substrates*, 1996, J. Raman Spectr., 27, 379-384.

Jennings C., R. Aroca, A. M. Hor, and R. O. Loutfy, *Surface-enhanced Raman scattering from copper and zinc phthalocyanine complexes by silver and indium island films*, 1984, Anal. Chem., 56, 203.

Ni F., R. Sheng, and T. M. Cotton, *Flow-injection analysis and real-time Detection of RNA bases by surface-enhanced Raman-spectroscopy*, 1990, Anal. Chem., 62, 1958.

Moody R. L., T. Vo Dinh, and W. H. Fletcher, *Investigation of Experimental Parameters for Surface-Enhanced Raman Scattering (SERS) Using Silver-Coated Microsphere Substrates*, 1987, Appl. Spectr., 41, 966.

Bello J. M., D. L. Stokes and T. Vo Dinh, *Silver-Coated Alumina as a New Medium for Surface-Enhanced Raman Scattering Analysis*, 1989, Appl. Spectrosc., 43. 1325.

Sutherland, *A Portable Surface-Enhanced Raman Spectrometer*, Instrumentation Science & Technology, vol. 22, Issue 3 Aug. 1994, pp. 231-239.

Alak A., and T. Vo Dinh, *Silver-Coated Fumed Silica as New Substrate Materials for Surface-Enhanced Raman Scattering*, 1989, Anal. Chem., 61, 656.

Liao P. F., and M. B. Stern, *Surface-enhanced Raman scattering on gold and aluminum particle arrays*, 1982, Opt. Lett., 7, 483.

Vo Dinh T., M. Meier, and A. Wokaun, 1986, *Surface Enhanced Raman Spectroscopy with Silver Particles on Stochastic Post Substrates*, Anal. Chim. Acta, 181, 139.

Enlow P. D., M. C. Buncick, R. J. Warmack, and T. Vo Dinh, *Detection of Nitro polynuclear Aromatic Compounds by Surface Enhanced Raman Spectroscopy*, 1986, Anal. Chem., 58, 1119.

Vo Dinh T., 1989, *Surface-Enhanced Raman Spectrometry, in Chemical Analysis of Polycyclic Aromatic Compounds*, Wiley, T. Vo-Dinh, Ed., New York.

M. Volkan, D.L. Stokes and T. Vo-Dinh, *A Sol-Gel Derived AgCl Photochromic Coating on Glass for SERS Chemical Sensor Application*, Sensors and Actuators B, 106, 660-667 (2004).

Lie Lin, et al., "Distribution and photobleaching of photosensitizer chlorophyll derivative (DPD) in SMCF7 cancer cells", Proc. of SPIE vol. 6534, 65342G-1 to 65342G-6.

Liang-yan Xue, et al., "The death of human cancer cells following photodynamic therapy: apoptosis competence is necessary for Bcl-2 protection but not for induction of autophagy", Photochemistry and Photobiology, 2007, 83: pp. 1016-1023.

Mamta Khurana, et al., "Quantitative in vitro demonstration of two-photon photodynamic therapy using photofrin and visudyne", Photochemistry and Photobiology, 2007, 83; pp. 1441-1448.

Dakrong Pissuwan, et al., "Targeted destruction of murine macrophage cells with bioconjugated gold nanorods", Journal of Nanoparticle Research (2007) 9: pp. 1109-1124.

Kazuyuki Ishii, et al., "Control of photobleaching in photodynamic therapy using the photodecarbonylation reaction of ruthenium phthalocyanine complexes via stepwise two-photon excitation", Journal of Phys. Chem. B 2008, 112, pp. 3138-3143.

Qingling Wan, et al., "Bid is required in NPe6-PDT-induced apoptosis", Photochemistry and Photobiology, 2008, 84: pp. 250-257.

Maria Kyriazi, et al., "Topical photodynamic therapy of murine non-melanoma skin carcinomas with aluminum phthalocyanine chloride and a diode laser: pharmacokinetics, tumor response and cosmetic outcomes", Photodermatology, Photoimmunology & Photomedicine 24, pp. 87-94.

Quanhong Liu, et al., "Sonodynamic antitumor effect of protoporphyrin IX disodium salt on S180 solid tumor", Experimental Chemotherapy, Chemotherapy, 2007; 53: pp. 429-436.

Liping Song, et al., "Naphthalocyanine-reconstituted LDL nanoparticles for in vivo cancer imaging and treatment", International Journal of Nanomedicine, 2007: 2(4), pp. 767-774.

Garif Akchurin, et al., "Gold nanoshell photomodification under a single-nanosecond laser pulse accompanied by color-shifting and bubble formation phenomena", Nanotechnology 19, (2008), 015701, 8 pp.

Express, Oct. 23, 2008, Thursday, "Peeled scotch tape emits x-rays" 1 pp.

Martina E. Wieder, et al., Intracellular photodynamic therapy with photosensitizer-nanoparticle conjugates: cancer therapy using a 'Trojan horse', Photochemical & Photobiological Sciences, 2006, 5, pp. 727-734.

Yuanfang Liu, et al., "Investigation of water-soluble x-ray luminescence nanoparticles for photodynamic activation", Applied Physics Letter 92, 043901, (2008), 043901-1 to 043901-3.

Peng Zhang, et al., "Versatile photosensitizers for photodynamic therapy at infrared excitation", Journal of the American Chemical Society, vol. 129, 2007, No. 15, pp. 4526-4527.

Joshua E. Collins, et al., "Infrared light utilized for photodynamic therapy by activation of rare earth phosphors for visible light generation", Proc. of SPIE, vol. 6427, 642717-1 to 642717-12.

Qingdong Zheng, et at., "Water-soluble two-photon absorbing nitrosyl complex for light-activated therapy through nitric oxide release", Molecular Pharmaceutics, vol. 5, No. 3, pp. 389-398.

Shane O. McDonnell, et al., "Supramolecular photonic therapeutic agents", Journal of the American Chemical Society, 2005, 127, pp. 16360-16361.

BBC News /Health, one minute world news, "Nano device times drug release", http://news.bbc.co.uk/2hi/health/7808672.stm.

Bisaccia E., et al., "Extracorporeal photopheresis in the treatment of AIDS-related complex: extended trial", J. Acuir. Immune Defic. Syndr., Apr. 1993; 6(4): pp. 386-392, (abstract)-AbstractPlus.

Martina E. Wieder, "Intracellular photodynamic therapy with photosensitizer-nanoparticle conjugates: cancer therapy using a 'Trojan horse'", Photochem. & Photobiol. Sci., 2006, 5, pp. 727-734.

Petras Juzenas, et al., "Quantum dots and nanoparticles for photodynamic and radiation therapies of cancer", ScienceDirect, Advanced Drug Delivery Reviews, vol. 60, Dec. 14, 2008, pp. 1600-1614, abstract.

Hede Shantesh et al., ""Nano": The new nemesis of cancer", Journal of Cancer Research and Therapeutics, vol. 2, No. 4, Oct.-Dec. 2006, pp. 186-195.

Maksym Yezhelyev, et al., "Inorganic Nanoparticles for predictive oncology of breast cancer", Nanomedicine, 2009, 4 (1), pp. 83-103, www.medscape.com.

James Hainfeld, et al., "Scientists in the US have shown that gold nanoparticles can help X-rays kill cancerous cells more effectively in mice. The team hopes to refine the technique so that it will eventually work on humans" (J. Hainfeld et al., 2004, Phys. Med. Biol., 49, N309).

Sonia Kumar, et al. "Optical molecular imaging agents for cancer diagnostics and therapeutics" Nanomedicine, Future Medicine, vol. 1, 2006, pp. 23-30.

Richard L. Edelson, M.D., "Phtopheresis: a New Therapeutic Concept" The Yale Journal of Biology and Medicine, vol. 62, 1989, pp. 565-577.

Office Action issued Jan. 8, 2012 in Thai Patent Application No. 0901000748.

U.S. Appl. No. 14/245,644, filed Apr. 4, 2014, Bourke, et al.

English translation of Taiwanese Search Report issued May 12, 2014 in Taiwanese Patent Application No. 098105525, filed Feb. 20, 2009.

Office Action issued May 16, 2014, Taiwan Patent Application No. 098105525, filed Feb. 20, 2009.

(56) References Cited

OTHER PUBLICATIONS

Jean R. Starkey, et al., "New two-photon activated photodynamic therapy sensitizers induce xenograft tumor regressions after near-IR laser treatment through the body of the host mouse", Clin Cancer Res 2008;14(20), Oct. 15, 2008, pp. 6564-6573.

Yongjun Chen, et al., "Apoptosis induced by methylene-blue-mediated photodynamic therapy in melanomas and the involvement of mitochondrial dysfunction revealed by proteomics", Cancer Sci, Oct. 2008, vol. 99, No. 10, pp. 2019-2027.

Ashwin A. Bhirde, et al., Targeted killing of cancer cells in vivo and in vitro with EGF-directed carbon nanotube-based drug delivery, ACSNANO, vol. 3, No. 2, 2009, pp. 307-316.

O. Mermut et al., "Time-resolved luminescence measurements of the magnetic field effect on paramagnetic photosensitizers in photodynamic reactions", Proc. of SPIE, vol. 6845, 68450T-1 to 68450T8, 2008.

Luo Jun-Ming, et al., "Fabrication and Up-conversion luminescence of $Er^{3+}$:$Y_2O_3$ nanoparticles", Journal of Nanoscience and Nanotechnology, vol. 8, 2008, pp. 1211-1213.

Petras Juzenas, et al., "Quantum dots and nanoparticles for photodynamic and radiation therapies of cancer", Advanced Drug Delivery Reviews, (2008), 15 pages.

Pil-Sook G. Kim, et al., "X-ray-Excited optical luminescence (XEOL) and X-ray absorption fine structures (XAFS) studies of gold(I) complexes with diphosphine and bipyridine ligands", Inorganic Chemistry, vol. 46, No. 3, 2007, pp. 949-957.

Parmeswaran Diagaradjane, et al., "Modulation of in vivo tumor radiation response via gold nanoshell-mediated vascular-focused hyperthermia: characterizing an integrated antihypoxic and localized vascular disrupting targeting strategy", American Chemical Society, Nano Letters, vol. 8, No. 5, 2008, pp. 1492-1500.

\* cited by examiner

Plasmonics X ray Excitation of Metal Nanoparticles to enhance Photo-active Probes

Nanoparticle Chain PA Probes for Dual Plasmonic Excitation

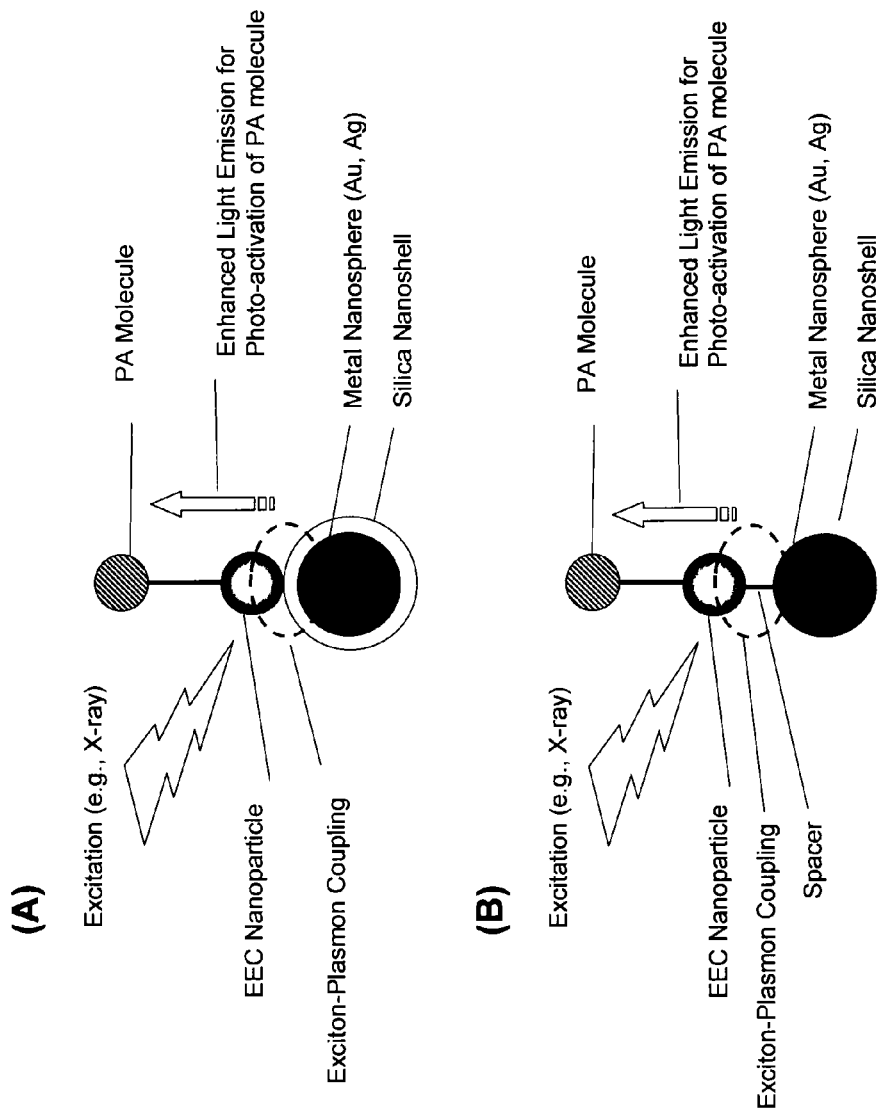

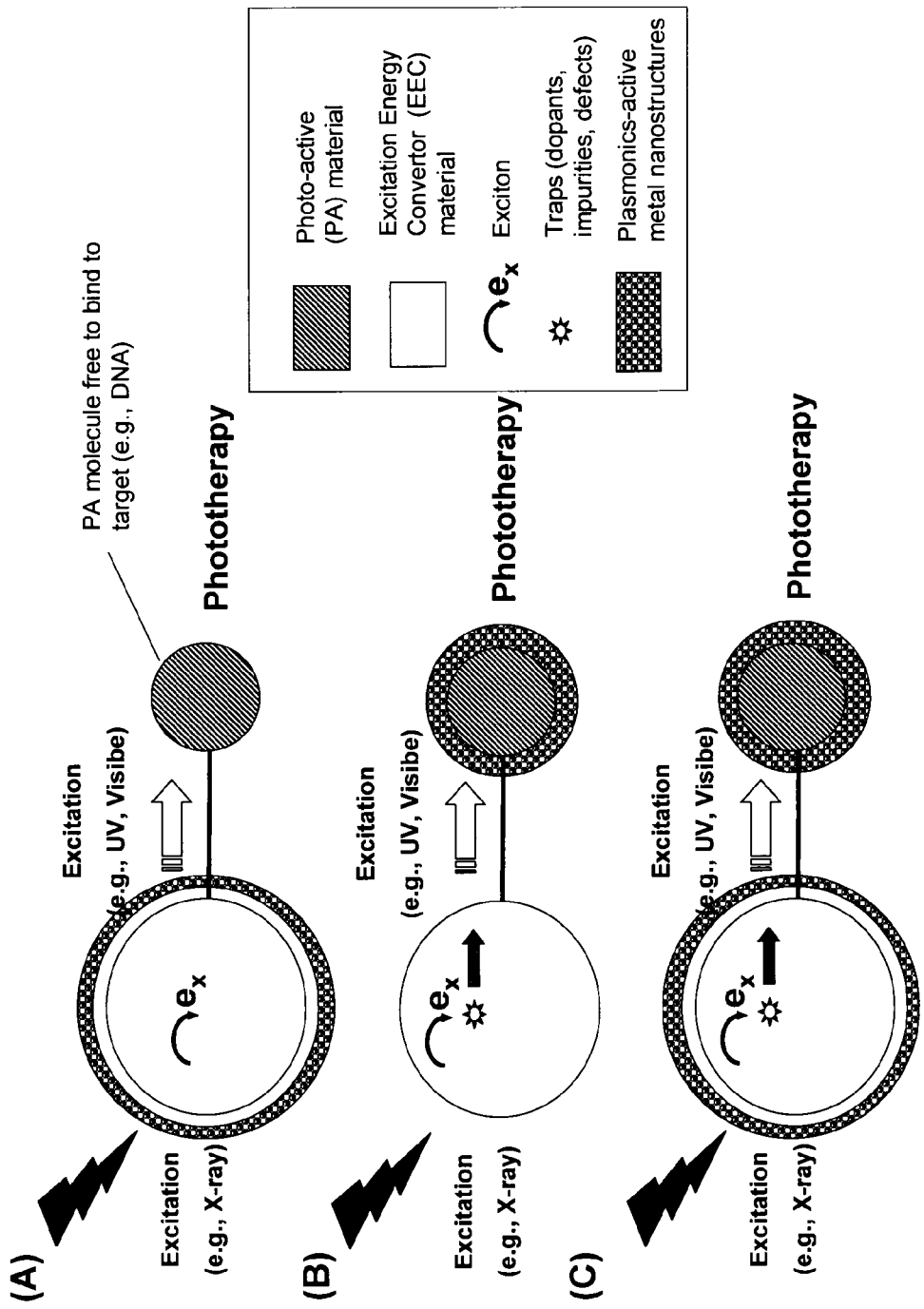

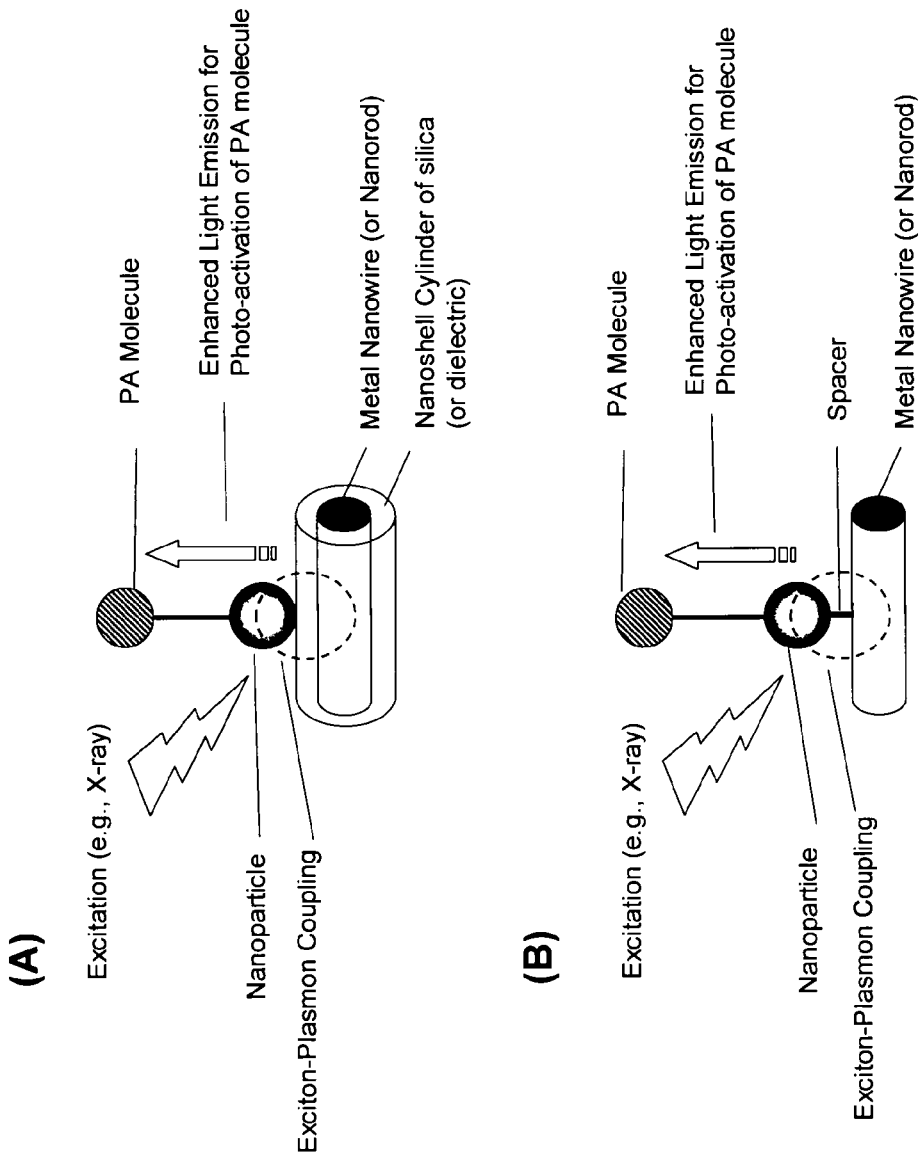

Exciton-Plasmon coupling Between Metal Nanorod Complex and EEC Nanoparticle

METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)

CROSS REFERENCE TO RELATED APPLICATIONS

This application is related to U.S. application Ser. No. 11/935,655, filed Nov. 6, 2007, and U.S. application Ser. No. 12/059,484, filed Mar. 31, 2008; and Provisional Applications Ser. No. 61/042,561, filed Apr. 4, 2008; 61/035,559, filed Mar. 11, 2008; and 61/080,140, filed Jul. 11, 2008; and 60/954,263, filed Aug. 6, 2007, the contents of each of which are hereby incorporated herein by reference. This application claims priority to U.S. Provisional Applications Ser. No. 61/080,429, filed Jul. 14, 2008 and 61/030,437, filed Feb. 21, 2008, the entire contents of each of which are hereby incorporated herein by reference.

BACKGROUND OF THE INVENTION

1. Field of Invention

The present invention relates to methods and systems for treating cell proliferation disorders, that provide better distinction between normal, healthy cells and those cells suffering a cell proliferation disorder (hereafter "target cells") and preferably that can be performed using non-invasive or minimally invasive techniques.

2. Discussion of the Background

Cell Proliferation Disorders

There are several types of cell proliferation disorders. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Of these, cancer is perhaps the most well known. The term "cancer" generally refers to a diverse class of diseases that are commonly characterized by an abnormal proliferation of the diseased cells. A unifying thread in all known types of cancer is the acquisition of abnormalities in the genetic material of the cancer cell and its progeny. Once a cell becomes cancerous, it will proliferate without respect to normal limits, invading and destroying adjacent tissues, and may even spread to distant anatomic sites through a process called metastasis. These life-threatening, malignant properties of cancers differentiate them from benign tumors, which are self-limited in their growth and do not invade or metastasize.

The impact of cancer on society cannot be overstated. The disease may affect people at all ages, with a risk factor that significantly increases with a person's age. It has been one of the principal causes of death in developed countries and, as our population continues to age, it is expected to be an even greater threat to our society and economy. Therefore, finding cures and effective treatments for cancer has been, and remains, a priority within the biomedical research community.

Treatment Methods

There are two main types of reactions in phototherapy:
(1) Type I reactions involve electrons and hydrogen atoms, which are transferred between photo-active molecules (also called photosensitizers) and substrates or solvent molecules. Oxygen may participate in subsequent reactions: e.g., psoralens in photopheresis and PUVA.
(2) Type II reactions involve singlet oxygen formation by energy transfer from PA molecules in the lowest triplet state to oxygen in the ground state: e.g., photodynamic therapy (PDT)

Existing treatments for cell proliferation disorders such as cancer include surgery, chemotherapy, radiation therapy, immunotherapy, monoclonal antibody therapy, and several other lesser known methods. The choice of therapy usually depends on the location and severity of the disorder, the stage of the disease, as well as the patient's response to the treatment.

While some treatments may only seek to manage and alleviate symptoms of the disorder, the ultimate goal of any effective therapy is the complete removal or cure of all disordered cells without damage to the rest of the body. With cancer, although surgery may sometimes accomplish this goal, the propensity of cancer cells to invade adjacent tissue or to spread to distant sites by microscopic metastasis often limits the effectiveness of this option. Similarly, the effectiveness of current chemotherapy is often limited by toxicity to other tissues in the body. Radiation therapy suffers from similar shortcomings as other aforementioned treatment methods. Most of these cancer treatment methods, including radiation therapy, are known to cause damage to DNA, which if not repaired during a critical stage in mitosis, the splitting of the cell during cell proliferation, leads to a programmed cell death, i.e. apoptosis. Further, radiation tends to damage healthy cells, as well as malignant tumor cells.

In one existing treatment known as extracorporeal photopheresis (ECP), excellent results have been observed since its initial approval by the FDA in 1988.

Extracorporeal photopheresis is a leukapheresis-based immunomodulatory therapy that has been approved by the US Food and Drug Administration for the treatment of cutaneous T-cell lymphoma (CTCL). ECP, also known as extracorporeal photochemotherapy, is performed at more than 150 centers worldwide for multiple indications. Long-term follow-up data are available from many investigators that indicate ECP produces disease remission and improved survival for CTCL patients. In addition to CTCL, ECP has been shown to have efficacy in the treatment of other T-cell mediated disorders, including chronic graft versus host disease (GVHD) and solid organ transplant rejection. ECP use for the treatment of autoimmune disease, such as systemic sclerosis and rheumatoid arthritis, is also being explored.

ECP is generally performed using the UVAR XTS Photopheresis System developed by Therakos, Inc (Exton, Pa.). The process is performed through one intravenous access port and has 3 basic stages: (1) leukapheresis, (2) photoactivation, and (3) reinfusion, and takes 3-4 hours to complete. A typical treatment session would resemble the following sequence of events:

(1) One 16-gauge peripheral intravenous line or central venous access is established in the patient;

(2) Blood (225 mL) is passed through 3 cycles of leukapheresis, or 125 mL of blood is passed through 6 cycles, depending on the patient's hematocrit value and body size. At the end of each leukapheresis cycle, the red blood cells and plasma are returned to the patient;

(3) The collected WBCs (including approximately 5% of the peripheral blood mononuclear cells) are mixed with heparin, saline, and 8-methoxypsoralen (8-MOP), which intercalates into the DNA of the lymphocytes upon exposure to UVA light and makes them more susceptible to apoptosis when exposed to UVA radiation;

(4) The mixture is passed as a 1-mm film through a sterile cassette surrounded by UVA bulbs for 180 minutes, resulting in an average UVA exposure of 2 J/cm$^2$ per lymphocyte; and (5) The treated WBC mixture is returned to the patient.

Over the past 20 years, on-going research has explored the mechanism of action of ECP. The combination of 8-MOP and UVA radiation causes apoptosis of the treated T cells and may cause preferential apoptosis of activated or abnormal T cells, thus targeting the pathogenic cells of CTCL or GVHD. However, given that only a small percentage of the body's lymphocytes are treated, this seems unlikely to be the only mechanism of action.

Other evidence suggests that ECP also induces monocytes to differentiate into dendritic cells capable of phagocytosing and processing the apoptotic T-cell antigens. When these activated dendritic cells are reinfused into the systemic circulation, they may cause a systemic cytotoxic CD8$^+$ T-lymphocyte-mediated immune response to the processed apoptotic T-cell antigens.

Finally, animal studies indicate that photopheresis may induce antigen-specific regulatory T cells, which may lead to suppression of allograft rejection or GVHD.

However, there are still many limitations to ECP. For example, ECP requires patient to be connected to a machine for hours per treatment. It requires establishing peripheral intravenous line or central venous access, which may be difficult to do in certain disease states such as systemic sclerosis or arthritis. There is also a risk of infection at the venous or central line site, or in the central line catheter. Further, it requires removing typically several hundred milliliters of whole blood from the patient, hence, the treatment is limited to patients who has sufficiently large initial volume of blood to be withdrawn. The American Association of Blood Blanks recommend a limit of extracorporeal volume to 15% of the patient's whole body blood volume. Therefore, the size of the volume that can be treated generally has to be at least 40 kg or more. Risk of contracting blood-born pathogen (Hepatitis, HIV, etc.) due to exposure to contaminated operating system is also a concern.

Alternatively, a patient can be treated in vivo with a photosensitive agent followed by the withdrawal of a sample from the patient, treatment with UV radiation in vitro (ex vivo), and reinjecting the patient with the treated sample. This method is known for producing an autovaccine. A method of treating a patient with a photosensitive agent, exposing the patient to an energy source and generating an autovaccine effect wherein all steps are conducted in vivo has not been described. See WO 03/049801, U.S. Pat. Nos. 6,569,467; 6,204,058; 5,980,954; 6,669,965; 4,838,852; 7,045,124, and 6,849,058. Moreover, the side effects of extracorporeal photopheresis are well known and include nausea, vomiting, cutaneous erythema, hypersensitivity to sunlight, and secondary hematologic malignancy. Researchers are attempting to use photopheresis in experimental treatments for patients with cardiac, pulmonary and renal allograft rejection; autoimmune diseases, and ulcerative colitis.

A survey of known treatment methods reveals that these methods tend to face a primary difficulty of differentiating between normal cells and target cells when delivering treatment, often due to the production of singlet oxygen which is known to be non-selective in its attack of cells, as well as the need to perform the processes ex vivo, or through highly invasive procedures, such as surgical procedures in order to reach tissues more than a few centimeters deep within the subject.

U.S. Pat. No. 5,829,448 describes simultaneous two-photon excitation of photo-agents using irradiation with low-energy photons such as infrared or near infrared light (NRI). A single photon and simultaneous two-photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest.

Chen et al., J. Nanosci. and Nanotech., 6:1159-1166 (2006); Kim et al., JACS, 129:2669-2675 (2007); U.S. 2002/0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 discloses methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multicellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue. However, the method is not suitable for treating a patient and does not teach any mechanisms for stimulating the photosensitizers, indirectly.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photosensitizer, inactivating substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

Also, U.S. Pat. No. 6,235,508 suggests that halogenated photosensitizers and blocking agents might be suitable for replacing 8-methoxypsoralen (8-MOP) in photopheresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photophoresis for antiviral treatments of raw blood and plasma.

U.S. Pat. No. 6,235,508 teaches away from 8-MOP and 4'-aminomethyl-4,5',8-trimethylpsoralen (AMT) and many other photoactivatable molecules, which are taught to have certain disadvantages. Fluorescing photosensitizers are said to be preferred, but the reference does not teach how to select a system of fluorescent stimulation or photoactivation using fluorescent photosensitizers. Instead, the fluorescing photosensitizer is limited to the intercalator that is binding to the DNA. The reference suggests that fluorescence indicates that such an intercalator is less likely to stimulate oxygen radicals. Thus, the reference fails to disclose any mechanism of photoactivation of an intercalator other than by direct photoactivation by UV light, although use of a UV light probe or X-rays is suggested for penetrating deeper into tissues. No examples are provided for the use of a UV light probe or for use of X-rays. No example of any stimulation by X-ray radiation is taught.

Psoralens and Related Compounds

U.S. Pat. No. 6,235,508 further teaches that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The crosslinking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

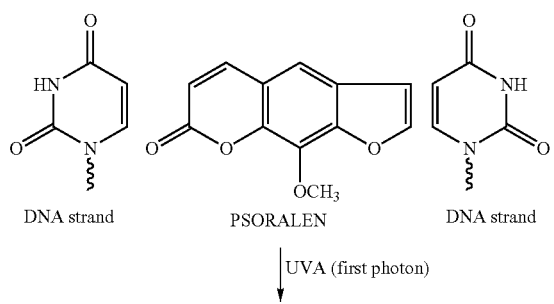

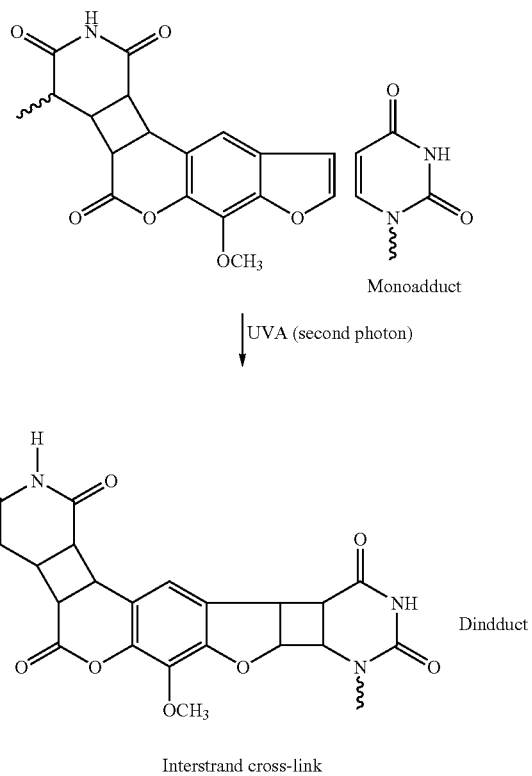

Monoadduct

Dindduct

Interstrand cross-link

In addition, the reference teaches that 8-MOP is unsuitable for use as an antiviral, because it damages both cells and viruses. Lethal damage to a cell or virus occurs when the psoralen is intercalated into a nucleic acid duplex in sites containing two thymines (or uracils) on opposing strands but only when it sequentially absorbs 2 UVA photons and thymines (or uracils) are present. U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens. Regardless, it is believed that no auto vaccine effect has been observed.

The best known photoactivatable compounds are derivatives of psoralen or coumarin, which are nucleic acid intercalators. The use of psoralen and coumarin photosensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species, such as shown below for coumarin:

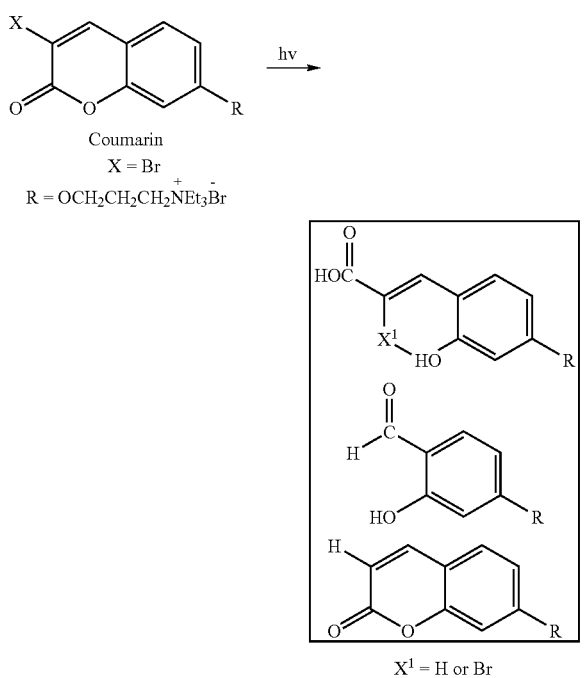

Research in this field over-simplifies mechanisms involved in the photoactivating mechanism and formation of highly reactive oxygen species, such as singlet oxygen. Both may lead to inactivating damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photophoresis causes the activation of an immune response with cytotoxic effects on untreated malignant cells. While the complexity of the immune response and cytotoxid effects is fully appreciated by researchers, a therapy that harnesses the system to successfully stimulate an auto vaccine effect against a targeted, malignant cell has been elusive, except for extracorporeal photophoresis for treating lymphoma.

Midden (W. R. Midden, Psoralen DNA photobiology, Vol 11 (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. U.S. Pat. No. 6,235,508 teaches that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 of Heindel discloses a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference.

U.S. Pat. No. 5,984,887 discloses using extracorporeal photophoresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Photodynamic Therapy (PDT)

PDT is a relatively new light-based treatment, which has recently been approved by the United States Food & Drug Administration (FDA) for the treatment of both early and late-stage lung cancer. Other countries have approved PDT for treatment of various cancers as well. Unlike chemotherapy, radiation, and surgery, PDT is useful in treating all cell types, whether small cell or non-small cell carcinoma. PDT involves treatment of diseases such as cancer using light action on a special photoactive class of drugs, by photodynamic action in vivo to destroy or modify tissue [Dougherty T. J. and Levy J. G., "Photodynamic Therapy and Clinical Applications", in *Biomedical Photonics Handbook*, Vo-Dinh T., Ed., CRC Press, Boca Raton Fla. (2003)]. PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration (AMD). Photodynamic therapy (PDT) is approved for commercialization worldwide both for various cancers (lung, esophagus) and for AMD.

The PDT process requires three elements: (1) a PA drug (i.e., photosensitizer), (2) light that can excite the photosensitizer and (3) endogenous oxygen. The putative cytotoxic agent is singlet oxygen, an electronically excited state of ground state triplet oxygen formed according to the Type II photochemical process, as follows.

$PA + h\nu \rightarrow {}^1PA^*(S)$ Excitation
$^1PA^*(S) \rightarrow {}^3PA^*(T)$ Intersystem crossing for singlet to triplet state
$^3PA^*(T) \rightarrow O_2 \rightarrow {}^1O^*_2 + PA$ Energy transfer from the drug to singlet oxygen where PA=photo-active drug at the ground state; $^1PA^*(S)$= excited singlet state; $^3PA^*(T)$=excited triplet state; $^1O^*_2$=singlet excited state of oxygen Because the triplet state has a relatively long lifetime (μsec to seconds) only photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared at ~1270 nm. Most PA photosensitizers in clinical use have triplet quantum yields in the range of 40-60% with the singlet oxygen yield being slightly lower. Competing processes include loss of energy by deactivation to ground state by fluorescence or internal conversion (loss of energy to the environment or surrounding medium).

However, while a high yield of singlet oxygen is desirable it is by no means sufficient for a photosensitizer to be clinically useful. Pharmacokinetics, pharmacodynamics, stability in vivo and acceptable toxicity play critical roles as well [Henderson B W, Gollnick S O, "*Mechanistic Principles of Photodynamic Therapy*", in *Biomedical Photonics Handbook*, Vo-Dinh T, Ed., CRC Press, Boca Raton Fla. (2003)]. For example, it is desirable to have relatively selective uptake in the tumor or other tissue being treated relative to the normal tissue that necessarily will be exposed to the exciting light as well. Pharmacodynamic issues such as the subcellular localization of the photosensitizer may be important as certain organelles appear to be more sensitive to PDT damage than others (e.g. the mitochondria). Toxicity can become an issue if high doses of photosensitizer are necessary in order to obtain a complete response to treatment. An important mechanism associated with PDT drug activity involves apoptosis in cells. Upon absorption of light, the photosensitiser (PS) initiates chemical reactions that lead to the direct or indirect production of cytotoxic species such as radicals and singlet oxygen. The reaction of the cytotoxic species with subcellular organelles and macromolecules (proteins, DNA, etc) lead to apoptosis and/or necrosis of the cells hosting the PDT drug. The preferential accumulation of PDT drug molecules in cancer cells combined with the localized delivery of light to the tumor, results in the selective destruction of the cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorbs light shorter than 640 nm in wavelength. For tumors occurring deep in tissue, second generation sensitizers, which have absorbance in the NIR region, such as porphyrin-based systems [R. K. Pandey, "*Synthetic Strategies in designing Porphyrin-Based* Photosensitizers', in *Biomedical Photonics Handbook*, Vo-Dinh T., Ed., CRC Press, Boca Raton Fla. (2003)], chlorines, phthalocyanine, and naphthalocyanine have been investigated.

PDT retains several photosensitizers in tumors for a longer time than in normal tissues, thus offering potential improvement in treatment selectivity. See Corner C., "Determination of [3H]- and [14C] hematoporphyrin derivative distribution in malignant and normal tissue," Cancer Res 1979, 3 9: 146-15 1; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favourable selectivity," Br J Cancer 1986, 54:717-725. Photodynamic therapy uses light of a specific wavelength to activate the photosensitizing agent. Various light sources have been developed for PDT, which include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Furthermore, when laser light is administered via external illumination of tissue surfaces, the treatment effect of PDT is confined to a few millimeters (i.e. superficial). The reason for this superficial limitation is mainly the limited penetration of the visible light used to activate the photosensitizer. Thus, PDT is used to treat the surfaces of critical organs, such as lungs or intra-abdominal organs, without damage to the underlying structures. However, even these treatments require significantly invasive techniques to treat the surface of the affected organs. Clinical situations use the procedure in conjunction with surgical debulking to destroy remnants of microscopic or minimal gross disease. It is possible that the laser light and small amount of remaining microscopic and minimal gross disease results in too little or highly damaged structures. Pre-clinical data show that some immune response is generated, but clinical trials have reported no auto vaccine effect similar to that produced by extracorporeal photophoresis in clinical conditions. Instead, the immune response appears to be vigorous only under limited conditions and only for a limited duration.

Problems

It is well recognized that a major problem associated with the existing methods of diagnosis and treatment of cell proliferation disorders is in differentiation of normal cells from target cells. Such target specificity is difficult to achieve by way of surgery since the strategy there is simply to cut out a large enough portion of the affected area to include all diseased cells and hope that no diseased cells have spread to other distant locations.

With chemotherapy, while some degree of differentiation can be achieved, healthy cells are generally adversely affected by chemo-agents. As in surgery, the treatment strategy in chemotherapy is also to kill off a large population of cells, with the understanding that there are far more normal cells than diseased cells so that the organism can recover from the chemical assault.

Radiation therapy works by irradiating cells with high levels of high energy radiation such as high-energy photon, electron, or proton. These high energy beams ionize the atoms which make up a DNA chain, which in turn leads to cell death. Unlike surgery, radiation therapy does not require placing patients under anesthesia and has the ability to treat tumors deep inside the body with minimal invasion of the body. However, the high doses of radiation needed for such therapies damages healthy cells just as effectively as it does diseased cells. Thus, similar to surgery, differentiation between healthy and diseased cells in radiation therapy is only by way of location. There is no intrinsic means for a radiation beam to differentiate between a healthy cell from a diseased cell either.

Other methods may be more refined. For example, one form of advanced treatment for lymphoma known as extracorporeal photopheresis involves drawing the patient's blood from his body into an instrument where the white cells (buffy coat) are separated from the plasma and the red blood cells. A small amount of the plasma separated in this process is then isolated and mixed with a photosensitizer (PS), a drug that can be activated by light. The buffy coat is then exposed to a light to activate the drug. The treated blood is then returned to the patient. In this example, one may think of the target-specificity problem as being solved by separating the blood from the rest of the body where the target components are easily exposed.

However, this procedure has its drawbacks; it requires drawing blood from the patient, thus requiring cumbersome machinery to perform and may require blood transfusion in order to maintain the volume of blood flow in the machine. Further, this also limits the size of the patient that can be treated, since the extracorporeal volume is great and too much withdrawal of blood increases the risk of hypovolemic shock. The method is also limited to treating blood-born cell proliferation related disorders such as lymphoma, and is not capable of treating solid tumors or other types of non-blood related cell proliferation disorders.

A problem encountered in PDT therapy is the inability to treat target areas that are more than a few centimeters beneath the surface of the skin without significant invasive techniques, and the fact that PDT typically operates by generation of sufficient quantities of singlet oxygen to cause cell lysis. However, singlet oxygen in sufficient concentration will lyse not only target cells, but also healthy cells rather indiscriminately.

Therefore, there still exists a need for better and more effective treatments that can more precisely target the diseased cells without causing substantial side-effects or collateral damages to healthy tissues, and which are capable of treating even solid tumors or other types of non-blood related cell proliferation disorders.

SUMMARY OF THE INVENTION

Accordingly, one object of the present invention is to provide a method for the treatment of a cell proliferation disorder that permits treatment of a subject in any area of the body while being non-invasive and having high selectivity for targeted cells relative to healthy cells through the use of plasmonics materials.

A further object of the present invention is to provide a method for treatment of a cell proliferation disorder which can use any suitable energy source as the initiation energy source in combination with plasmonics materials to activate the activatable pharmaceutical agent and thereby cause a predetermined cellular change to treat cells suffering from a cell proliferation disorder.

A further object of the present invention is to provide a method for treatment of a cell proliferation disorder using plasmonics in an energy cascade to activate an activatable pharmaceutical agent that then treats cells suffering from a cell proliferation disorder.

A further object of the present invention is to provide a method for treatment of a cell proliferation disorder using an energy cascade that has amplified electromagnetic fields to activate an activatable pharmaceutical agent that then treats cells suffering from a cell proliferation disorder.

A further object of the present invention is to provide a method for the treatment of a cell proliferation disorder that permits treatment of a subject in any area of the body while being non-invasive and having high selectivity for targeted cells relative to healthy cells through the use of exciton-plasmon enhancement.

A further object of the present invention is to provide a method for treatment of a cell proliferation disorder which can use any suitable energy source as the initiation energy source in combination with exciton-plasmon enhancement to activate the activatable pharmaceutical agent and thereby cause a predetermined cellular change to treat cells suffering from a cell proliferation disorder.

A further object of the present invention is to provide a method for treatment of a cell proliferation disorder using exciton-plasmon enhancement in an energy cascade to activate an activatable pharmaceutical agent that then treats cells suffering from a cell proliferation disorder.

These and other objects of the present invention, which will become more apparent in conjunction with the following detailed description of the preferred embodiments, either alone or in combinations thereof, have been satisfied by the discovery of a method for treating a cell proliferation disorder in a subject, comprising:

(1) administering to the subject at least one activatable pharmaceutical agent that is capable of effecting a predetermined cellular change when activated and at least one plasmonics agent; and (2) applying an initiation energy from an initiation energy source to the subject, wherein the plasmonics agent enhances the applied initiation energy, such that the enhanced initiation energy activates the activatable agent in situ, thus causing the predetermined cellular change to occur, wherein said predetermined cellular change treats the cell proliferation related disorder.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIGS. 24-1 and 24-2 are graphical representations of various embodiments of basic EPEP probes.

FIG. 25 is a graphical representation of various embodiments of EPEP probes having NPs, NWs and NRs.

DETAILED DESCRIPTION OF THE INVENTION

Figure 1:
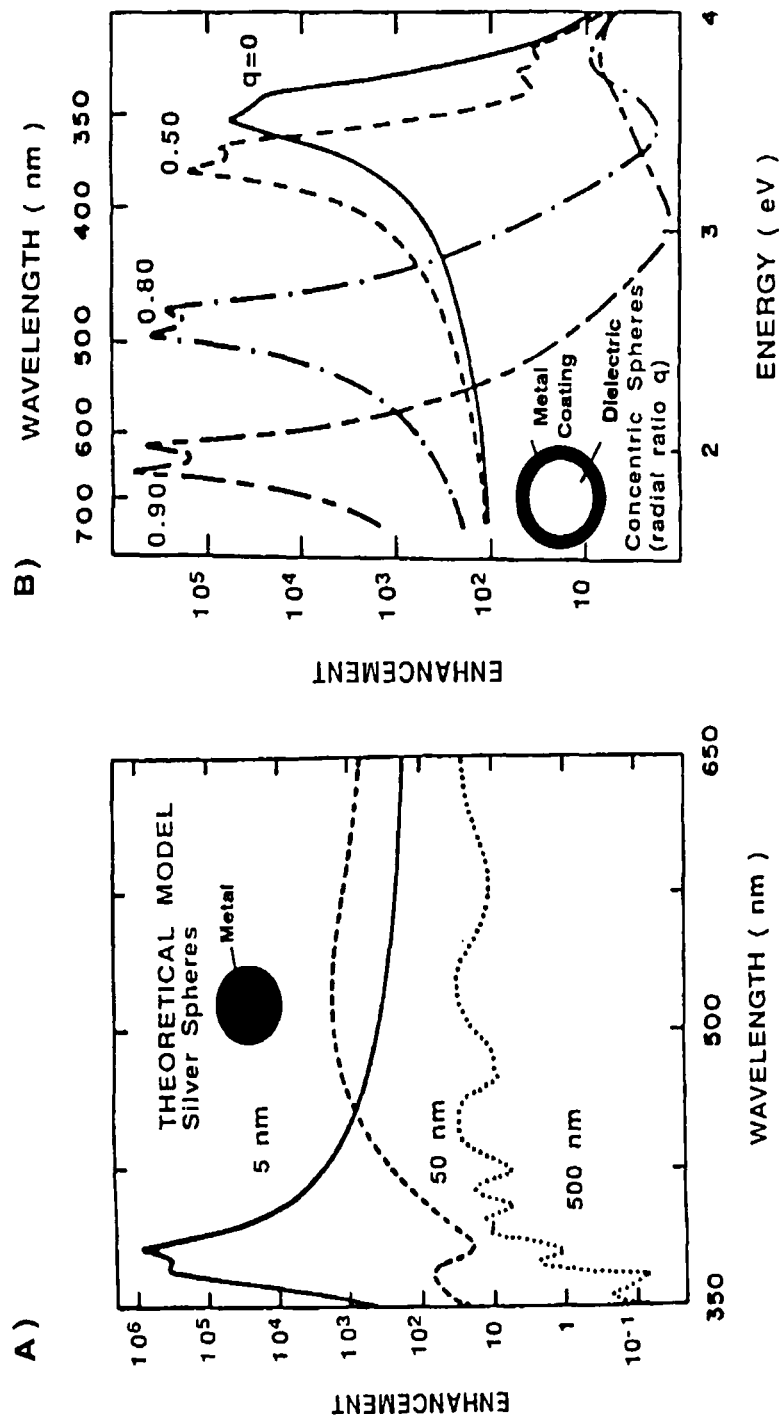
FIG. 1 is a graphical representation of plasmonic nanostructures and their theoretical electromagnetic enhancement at different excitation wavelengths.

The present invention sets forth a novel method of treating cell proliferation disorders that is effective, specific, and has few side-effects. Those cells suffering from a cell proliferation disorder are referred to herein as the target cells. A treatment for cell proliferation disorders, including solid tumors, is capable of chemically binding cellular nucleic acids, including but not limited to, the DNA or mitochondrial DNA or RNA of the target cells. For example, a photoactivatable agent, such as a psoralen or a psoralen derivative, is exposed in situ to an energy source capable of activating the photoactivatable agent or agents selected. In another example, the photoactivatable agent is a photosensitizer. The photoactivatable agent may be a metal nanocluster or a molecule or group of molecules, or a combination thereof. In particular, the present invention method takes advantage of the unique properties of plasmonics to enhance the photospectral therapy methods described in U.S. Ser. No. 11/935,655, filed Nov. 6, 2007 by one of the current inventors, the entire contents of which are hereby incorporated by reference. A preferred embodiment of the present invention is thus called "plasmonics-enhanced photospectral therapy" or PEPST for short.

As noted above, an object of the present invention is to treat cell proliferation disorders. Exemplary cell proliferation disorders may include, but are not limited to, cancer, as well as bacterial and viral infections where the invading bacteria grows at a much more rapid rate than cells of the infected host. In addition, treatment for certain developmental stage diseases related to cell proliferation, such as syndactyl), are also contemplated. Accordingly, in one embodiment, the present invention provides methods that are capable of overcoming the shortcomings of the existing methods. In general, a method in accordance with the present invention utilizes the principle of energy transfer or energy excitation, to and among molecular agents to control delivery and activation of pharmaceutically active agents such that delivery of the desired pharmacological effect is more focused, precise, and effective than the conventional techniques.

Generally, the present invention provides methods for the treatment of cell proliferation disorders, in which an initiation energy source provides an initiation energy that activates an activatable pharmaceutical agent to treat target cells within the subject. In one preferred embodiment, the initiation energy source is applied indirectly to the activatable pharmaceutical agent, preferably in proximity to the target cells. Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject.

Although not intending to be bound by any particular theory or be otherwise limited in any way, the following theoretical discussion of scientific principles and definitions are provided to help the reader gain an understanding and appreciation of the present invention. As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

As used herein, an "activatable pharmaceutical agent" (alternatively called a "photoactive agent" or PA) is an agent that normally exists in an inactive state in the absence of an activation signal. When the agent is activated by a matching activation signal under activating conditions, it is capable of effecting the desired pharmacological effect on a target cell (i.e. preferably a predetermined cellular change).

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof.

Activation of the agent may be as simple as delivering the signal to the agent or may further premise on a set of activation conditions. For example, in the former case, an activatable pharmaceutical agent, such as a photosensitizer, may be activated by UV-A radiation. Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors. Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic (electromagnetic) energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, production of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

The treatment of the present invention can be by the unique methods described in U.S. application Ser. No. 11/935,655, filed Nov. 6, 2007 (incorporated by reference above), or by a modified version of a conventional treatment such as PDT, but using a plasmonics-active agent to enhance the treatment by modifying or enhancing the applied energy or, in the case of using an energy modulation agent, modifying either the applied energy, the emitted energy from the energy modulation agent, or both.

In one preferred embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; a nanostructure, or combinations thereof; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention. Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 1 lists some photoactivatable molecules capable of being photoactivated to induce an auto vaccine effect.

TABLE 1

| | | | | | SSET and TTET rate constants for bichromophoric peptides | | | | | |
|---|---|---|---|---|---|---|---|---|---|---|
| Compound | $\lambda_{ex}$ (nm) | $E_{SSET}$ | $k_s$ of donor ($s^{-1}$) | $k_{SSET}$ ($s^{-1}$) | $K_{SSET}(s^{-1})$ (Average) | $R_0$ (Å) | R (Å) | $R_{model}$(Å) (Average) | $E_{TTET}$ | $k_{TTET}(s^{-1})$ |
| 1B | 224 | 96.3 | $9.5 \times 10^5$ | $2.44 \times 10^8$ | $1.87 \times 10^8$ | 14.7 | 9 | 9.5 | | |
| | 266 | 95 | | $1.8 \times 10^8$ | | | | | 2.5 | $5 \times 10^2$ |
| | 280 | 94 | | $1.36 \times 10^8$ | | | | | | |
| 1A | 224 | 80 | $9.5 \times 10^6$ | $3.8 \times 10^7$ | $3.67 \times 10^7$ | 14.7 | 11.8 | 14.1 | | |
| | 266 | 79 | | $3.6 \times 10^7$ | | | | | 2 | $3.6 \times 10^2$ |
| | 280 | 79 | | $3.6 \times 10^7$ | | | | | | |
| 2B | 224 | 77 | $9.5 \times 10^5$ | $3.1 \times 10^7$ | $3.9 \times 10^7$ | 14.7 | 11.9 | 5.5 | | |
| | 266 | 81 | | $3.9 \times 10^7$ | | | | | 32 | $9.4 \times 10^3$ |
| | 280 | 83 | | $4.7 \times 10^7$ | | | | | | |
| 2A | 224 | 69 | $9.5 \times 10^5$ | $2.1 \times 10^7$ | $3 \times 10^7$ | 14.7 | 12.2 | 8.1 | 74.3 | $5.7 \times 10^4$ |
| | 266 | 80 | | $3.7 \times 10^7$ | | | | | | |
| | 280 | 77 | | $3.2 \times 10^7$ | | | | | | |

TABLE 1-continued
SSET and TTET rate constants for bichromophoric peptides
| Compound | $\lambda_{ex}$ (nm) | $E_{SSET}$ | $k_s$ of donor (s$^{-1}$) | $k_{SSET}$ (s$^{-1}$) | $K_{SSET}$(s$^{-1}$) (Average) | $R_0$ (Å) | R (Å) | $R_{model}$(Å) (Average) | $E_{TTET}$ | $k_{TTET}$(s$^{-1}$) |
|---|---|---|---|---|---|---|---|---|---|---|
1A
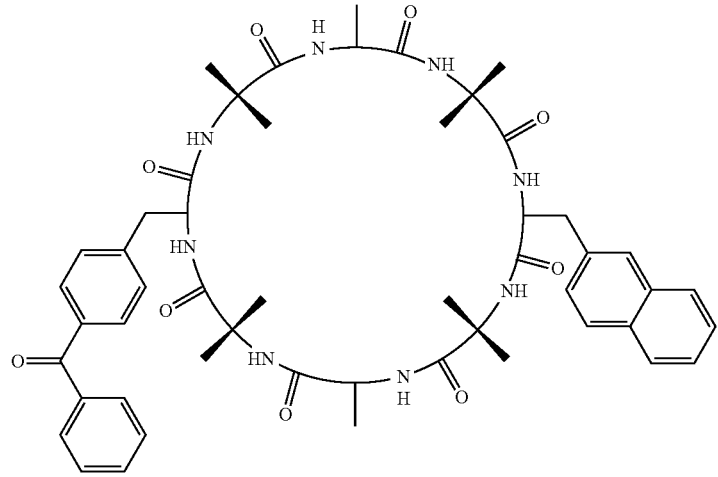
1B
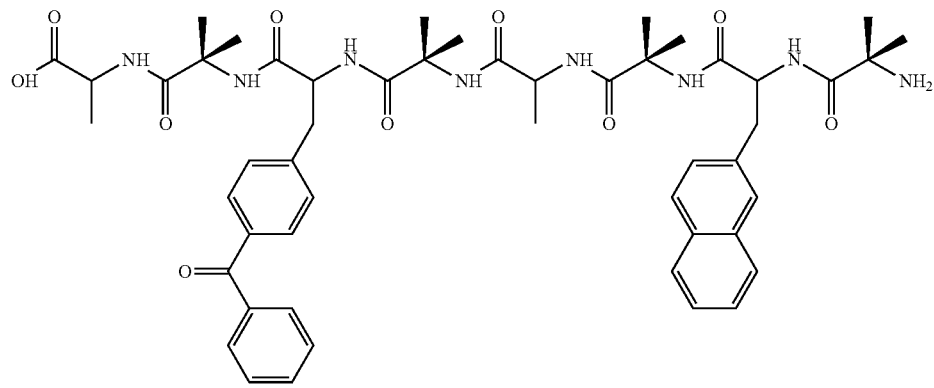
2A
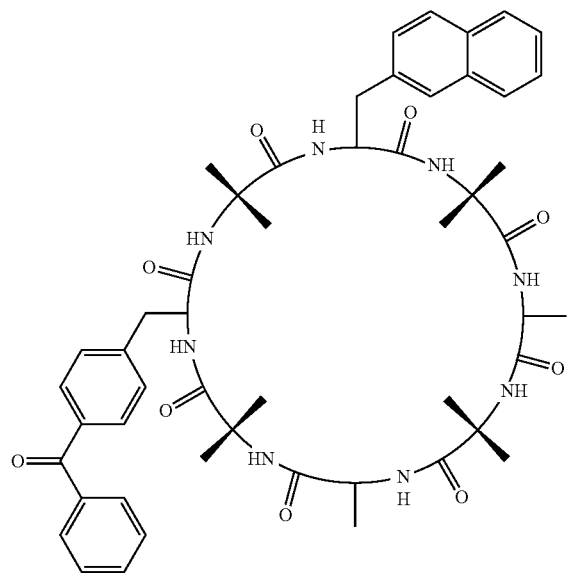

TABLE 1-continued

SSET and TTET rate constants for bichromophoric peptides

| Compound | $\lambda_{ex}$ (nm) | $E_{SSET}$ | $k_s$ of donor (s$^{-1}$) | $k_{SSET}$ (s$^{-1}$) | $K_{SSET}$(s$^{-1}$) (Average) | $R_0$ (Å) | $R$ (Å) | $R_{model}$(Å) (Average) | $E_{TTET}$ | $k_{TTET}$(s$^{-1}$) |
|---|---|---|---|---|---|---|---|---|---|---|
| 2B | | | | | | | | | | |

Table 2 lists some additional endogenous photoactivatable molecules.

TABLE 2

Biocompatible, endogenous fluorophore emitters.

| Endogenous Fluorophores | Excitation Max. (nm) | Emission Max. (nm) |
|---|---|---|
| Amino acids: | | |
| Tryptophan | 280 | 350 |
| Tyrosine | 275 | 300 |
| Phenylalanine | 280 | 280 |
| Structural Proteins: | | |
| Collagen | 325, 360 | 400, 405 |
| Elastin | 290, 325 | 340, 400 |
| Enzymes and Coenzymes: | | |
| flavin adenine dinucleotide | 450 | 535 |
| reduced nicotinamide dinucleotide | 290, 351 | 440, 460 |
| reduced nicotinamide dinucleotide phosphate | 336 | 464 |
| Vitamins: | | |
| Vitamins A | 327 | 510 |
| Vitamins K | 335 | 480 |
| Vitamins D | 390 | 480 |
| Vitamins $B_6$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, or a combination thereof.

As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. The energy can be modulated up to emit higher energy from the energy modulation agent compared to the input initiation energy, or can be modulated down to emit lower energy from the energy modulation agent compared to the input initiation energy. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In preferred embodiments, the energy modulation agent receives higher energy (e.g. x-ray) and re-emits in lower energy (e.g. UV-A). Energy transfer processes are also referred to as molecular excitation. Some modulation agents may have a very short energy retention time (on the order of fs-ns, e.g. fluorescent molecules) whereas others may have a very long half-life (on the order of seconds to hours, e.g. luminescent inorganic molecules or phosphorescent molecules). Suitable energy modulation agents include, but are not limited to, a biocompatible metal nanoparticle, metal coated with a biocompatible outer layer, a chemiluminescent molecule whose rate of luminescence is increased by microwave activation, fluorescing dye molecule, gold nanoparticle, a water soluble quantum dot encapsulated by polyamidoamine dendrimers, a luciferase, a biocompatible phosphorescent molecule, a biocompatible fluorescent molecule, a biocompatible scattering molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as an antibody, nucleic acid, peptide, a lipid, chitin or chitin-derivative, a chelate, a surface cell receptor, molecular imprints, aptamers, or other functionalized carrier that is capable of concentrating the UV-A emitting source in a specific target tumor.

Additionally, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

The initiation energy source can be any energy source capable of providing energy at a level sufficient to activate the activatable agent directly, or to provide the energy modulation agent with the input needed to emit the activation energy for the activatable agent (indirect activation). Preferable initiation energy sources include, but are not limited to, UV-A lamps or fiber optic lines, a light needle, an endoscope, and a linear accelerator that generates x-ray, gamma-ray, or electron beams. The energy used can be any type, including but not limited to, gamma ray, x-ray, UV, near-UV, visible, Near IR, IR, microwave, radio wave, etc. In a preferred embodiment the initiation energy capable of penetrating completely through the subject. Within the context of the present invention, the phrase "capable of penetrating completely through the subject" is used to refer to energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, x-rays, gamma rays, electron beams, microwaves and radio waves.

In one embodiment, the source of the initiation energy can be a radiowave emitting nanotube, such as those described by K. Jensen, J. Weldon, H. Garcia, and A. Zettl in the Department of Physics at the University of California at Berkeley. These nanotubes can be administered to the subject, and preferably would be coupled to the activatable pharmaceutical agent or the energy modulation agent, or both, such that upon application of the initiation energy, the nanotubes would accept the initiation energy (prefereably radiowaves), then emit radiowaves in close proximity to the activatable pharmaceutical agent, or in close proximity to the energy modulation agent, to then cause activation of the activatable pharmaceutical agent. In such an embodiment, the nanotubes would act essentially as a radiowave focusing or amplification device in close proximity to the activatable pharmaceutical agent or energy modulation agent.

Alternatively, the energy emitting source may be an energy modulation agent that emits energy in a form suitable for absorption by a further energy modulation agent. For example, the initiation energy source may be acoustic energy and one energy modulation agent may be capable of receiving acoustic energy and emitting photonic energy (e.g. sonoluminescent molecules) to be received by another energy modulation agent that is capable of receiving photonic energy. Other examples include transfer agents that receive energy at x-ray wavelength and emit energy at UV wavelength, preferably at UV-A wavelength. As noted above, a plurality of such energy modulation agents may be used to form a cascade to transfer energy from initiation energy source via a series of energy modulation agents to activate the activatable agent.

Signal transduction schemes as a drug delivery vehicle may be advantageously developed by careful modeling of the cascade events coupled with metabolic pathway knowledge to sequentially or simultaneously activate multiple activatable pharmaceutical agents to achieve multiple-point alterations in cellular function.

Photoactivatable agents may be stimulated by an energy source, such as irradiation, resonance energy transfer, exciton migration, electron injection, or chemical reaction, to an activated energy state that is capable of effecting the predetermined cellular change desired. In a preferred embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the present invention administers a photoactivatable agent to a patient, stimulates the photoactivatable agent to induce cell damage, and generates an auto vaccine effect. In one further preferred embodiment, the photoactivatable agent is stimulated via a resonance energy transfer.

One advantage is that multiple wavelengths of emitted radiation may be used to selectively stimulate one or more photoactivatable agents or energy modulation agents capable of stimulating the one or more photoactivatable agents. The energy modulation agent is preferably stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, such as apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B- absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule. Alternatively, one can administer the initiation energy source to the subject. Within the context of the present invention, the administering of the initiation energy source means the administration of an agent, that itself produces the initiation energy, in a manner that permits the agent to arrive at the target cell within the subject without being surgically inserted into the subject. The administration can take any form, including, but not limited to, oral, intravenous, intraperitoneal, inhalation, etc. Further, the initiation energy source in this embodiment can be in any form, including, but not limited to, tablet, powder, liquid solution, liquid suspension, liquid dispersion, gas or vapor, etc. In this embodiment, the initiation energy source includes, but is not limited to, chemical energy sources, nanoemitters, nanochips, and other nanomachines that produce and emit energy of a desired frequency. Recent advances in nanotechnology have provided examples of various devices that are nanoscale and produce or emit energy, such as the Molecular Switch (or Mol-Switch) work by Dr. Keith Firman of the EC Research and Development Project, or the work of Cornell et al. (1997) who describe the construction of nanomachines based around ion-channel switches only 1.5 nm in size, which use ion channels formed in an artificial membrane by two gramicidin molecules: one in the lower layer of the membrane attached to a gold electrode and one in the upper layer tethered to biological receptors such as antibodies or nucleotides. When the receptor captures a target molecule or cell, the ion channel is broken, its conductivity drops, and the biochemical signal is converted into an electrical signal. These nanodevices could also be coupled with the present invention to provide targeting of the target cell, to deliver the initiation energy source directly at the desired site. In another embodiment, the present invention includes the administration of the activatable pharmaceutical agent, along with administration of a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the activatable pharmaceutical agent in vivo after administration. The administration of the activatable pharmaceutical agent and the source of chemical energy can be performed sequentially in any order or can be performed simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

In the PEPST embodiment of the present invention, the present invention is significantly different from the phototherapy technique often referred to as Photo-thermal Therapy (PTT). To illustrate the difference between the present invention PEPST, a form of photospectral therapy (PST) and the PTT technique, the photochemical processes involved in PST and PPT is discussed below.

When drug molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_o$ to some vibrational level of one of the excited singlet states, $S_n$, in the manifold $S_1, \ldots, S_n$. In condensed media (tissue), the molecules in the $S_n$ state deactivate rapidly, within $10^{-13}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ via an internal conversion (IC) process. IC processes are transitions between states of the same multiplicity. The molecule subsequently deactivates to the lowest vibronic levels of $S_{n-1}$ via a VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local cell or tissue destruction. The light absorbing species include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of laser energy needed to induce local damage of the diseased cells, making the therapy method less invasive. A problem associated with the use of dye molecules is their photobleaching under laser irradiation. Therefore, nanoparticles such as gold nanoparticles and nanoshells have recently been used. The promising role of nanoshells in photothermal therapy of tumors has been demonstrated [Hirsch, L. R., Stafford, R. J., Bankson, J. A., Sershen, S. R., Rivera, B., Price, R. E., Hazle, J. D., Halas, N. J., and West, J. L., *Nanoshell-mediated near-infrared thermal therapy of tumors under magnetic resonance guidance*. PNAS, 2003. 100(23): p. 13549-13554]. The use of plasmonics-enhanced photothermal properties of metal nanoparticles for photothermal therapy has also been reviewed (Xiaohua Huang & Prashant K Jain & Ivan H. El-Sayed & Mostafa A. El-Sayed, "*Plasmonic photothermal therapy (PPTT) using gold nanoparticles*", Lasers in Medical Science, August 2007)

The PST method of the present invention, however, is based on the radiative processes (fluorescence, phosphorescence, luminescence, Raman, etc) whereas the PTT method is based on the radiationless processes (IC, VR and heat conversion) in molecules.

Basic Principle of Plasmonics and Enhanced Electromagnetic Fields

Whereas the photothermal properties of plasmonics metal nanoparticles have been used, the spectroscopic absorption and emission of plasmonics-active nanoparticles in phototherapy have not been reported.

In the present invention PEPST, the plasmonics-enhanced spectroscopic properties (spectral absorption, emission, scattering) are the major factors involved in the treatment.

The PEPST principle is based on the enhancement mechanisms of the electromagnetic field effect. There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified emission (luminescence, Raman, etc.) field, which further polarizes the metal particle, thereby acting as an antenna to further amplify the Raman/Luminescence signal.

Electromagnetic enhancements are divided into two main classes: a) enhancements that occur only in the presence of a radiation field, and b) enhancements that occur even without a radiation field. The first class of enhancements is further divided into several processes. Plasma resonances on the substrate surfaces, also called surface plasmons, provide a major contribution to electromagnetic enhancement. An effective type of plasmonics-active substrate comprises nanostructured metal particles, protrusions, or rough surfaces of metallic materials. Incident light irradiating these surfaces excites conduction electrons in the metal, and induces excitation of surface plasmons leading to Raman/luminescence enhancement. At the plasmon frequency, the metal nanoparticles (or nanostructured roughness) become polarized, resulting in large field-induced polarizations and thus large local fields on the surface. These local fields increase the luminescence/Raman emission intensity, which is proportional to the square of the applied field at the molecule. As a result, the effective electromagnetic field experienced by the analyte molecule on these surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$ of Raman or luminescence can, in turn, polarize the metallic nanostructures and, if $\lambda$ is in resonance with the localized surface plasmons, the nanostructures can enhance the observed emission light (Raman or luminescence).

There are two main sources of electromagnetic enhancement: (1) first, the laser electromagnetic field is enhanced due to the addition of a field caused by the polarization of the metal particle; (2) in addition to the enhancement of the excitation laser field, there is also another enhancement due to the molecule radiating an amplified Raman/luminescence field, which further polarizes the metal particle, thereby acting as an antenna to further amplify the Raman/luminescence signal. Plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents thus provides a selective and efficient phototherapy strategy. The tunability of the spectral properties of the metal nanoparticles and the biotargeting abilities of the plasmonic nanostructures make the PEPST method promising.

The present invention PEPST is based on several important mechanisms:
Increased absorption of the excitation light by the plasmonic metal nanoparticles, resulting in enhanced photoactivation of drug molecules
Increased absorption of the excitation light by the plasmonic metal nanoparticles that serve as more efficient energy modulation agent systems, yielding more light for increased excitation of PA molecules
Increased absorption of the excitation light by the photoactive drug system adsorbed on or near the plasmonic metal nanoparticles
Increased light absorption of the energy modulation agent molecules adsorbed on or near the metal nanoparticles
Amplified light emission from the energy modulation agent molecules adsorbed on or near the metal nanoparticles
Increased absorption of emission light emitted from the energy modulation agent by the PA molecule One of several phenomena that can enhance the efficiency of light emitted (Raman or luminescence) from molecules adsorbed or near a metal nanostructures Raman scatter is the surface-enhanced Raman scattering (SERS) effect. In 1984, the general applicability of SERS as an analytical technique was first reported by one of the present inventors, and the possibility of SERS measurement for a variety of chemicals including several homocyclic and heterocyclic polyaromatic compounds [T. Vo-Dinh, M Y K Hiromoto, G. M Begun and R. L. Moody, "*Surface-enhanced Raman spectroscopy for trace organic analysis,*" *Anal. Chem.*, vol. 56, 1667, 1984]. Extensive research has been devoted to understanding and modeling the Raman enhancement in SERS since the mid 1980's. FIG. 1, for example, shows the early work by Kerker modeling electromagnetic field enhancements for spherical silver nanoparticles and metallic nanoshells around dielectric cores as far back as 1984 [M. M. Kerker, *Acc. Chem. Res.,* 17, 370 (1984)]. This figure shows the result of theoretical calculations of electromagnetic enhancements for isolated spherical nanospheres and nanoshells at different excitation wavelengths. The intensity of the normally weak Raman scattering process is increased by factors as large as $10^{13}$ or $10^{15}$ for compounds adsorbed onto a SERS substrate, allowing for single-molecule detection. As a result of the electromagnetic field enhancements produced near nanostructured metal surfaces, nanoparticles have found increased use as fluorescence and Raman nanoprobes.

The theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons"; and b) a chemical effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface.

Design, Fabrication and Operation of PEPST Probes

Figure 2:
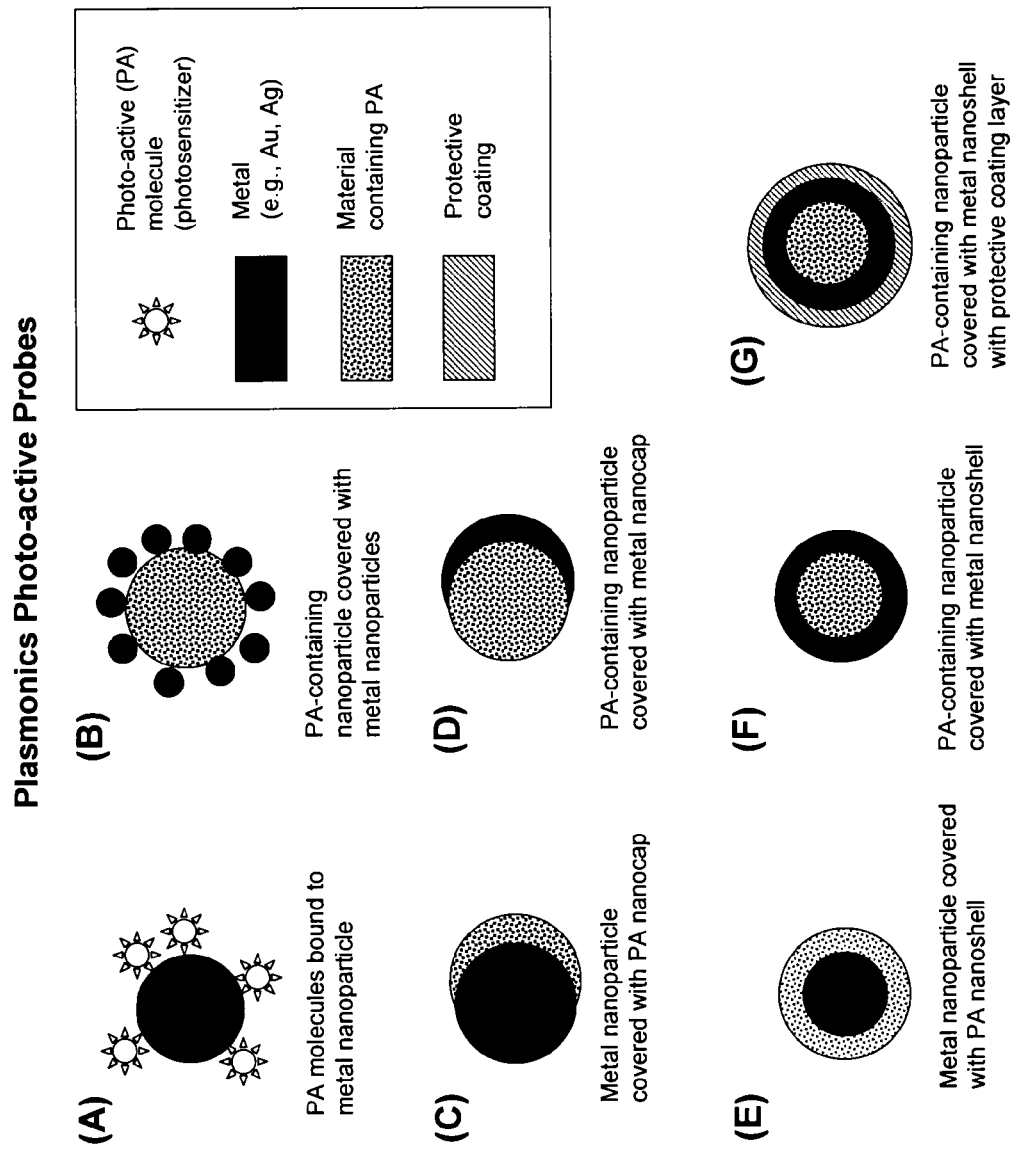
FIG. 2 provides representative embodiments of plasmonics photo-active probes useful in the present invention.

FIG. 2 shows a number of the various embodiments of PEPST probes that can be designed:
- (A) probe comprising PA molecules bound to a metal (gold) nanoparticle;
- (B) PA-containing nanoparticle covered with metal nanoparticles;
- (C) Metal nanoparticle covered with PA nanocap;
- (D) PA-containing nanoparticle covered with metal nanocap;
- (E) Metal nanoparticle covered with PA nanoshell;
- (F) PA-containing nanoparticle covered with metal nanoshell; and
- (G) PA-containing nanoparticle covered with metal nanoshell with protective coating layer.

Figure 3:
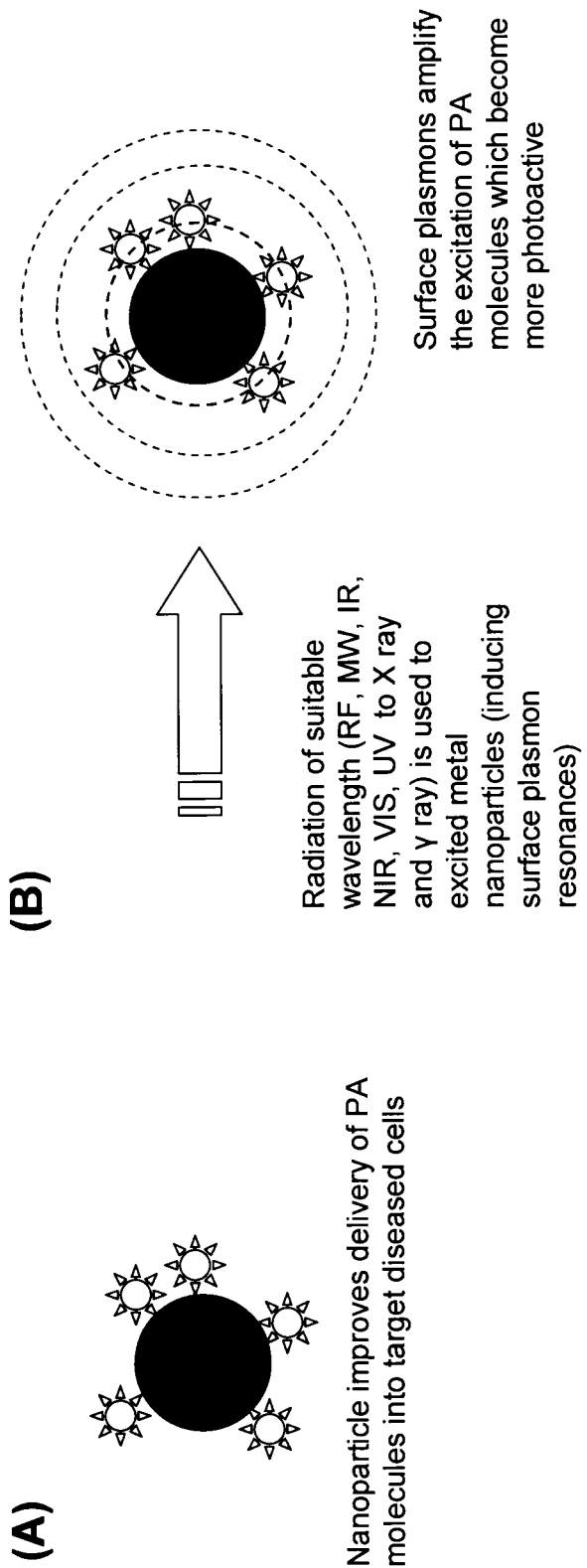
FIG. 3 is a graphical explanation of the plasmonics-enhanced effect of photospectral therapy used in the present invention.

A basic embodiment of the PEPST probe is shown in FIG. 2A. This probe comprises PA molecules bound to a metal (e.g., gold) nanoparticle. FIG. 3 illustrates the plasmonics-enhancement effect of the PEPST probe. The gold nanoparticles can serve as a drug delivery platform. Gold nanoparticles have been described as a novel technology in the field of particle-based tumor-targeted drug delivery [Giulio F. Paciotti and Lonnie Myer, David Weinreich, Dan Goia, Nicolae Pavel, Richard E. McLaughlin, Lawrence Tamarkin, "*Colloidal Gold: A Novel Nanoparticle Vector for Tumor Directed Drug Delivery, Drug Delivery,* 11:169-183, 2004]. Particle delivery systems capable of escaping phagocytic clearance by the reticuloendothelial system (RES) can facilitate targeting cancer therapeutics to solid tumors. Such delivery systems could preferentially accumulate within the tumor microenvironment under ideal conditions. A particle delivery system capable of sequestering a phototherapeutic drug selectively within a tumor may also reduce the accumulation of the drug in healthy organs. Consequently, these delivery systems may increase the relative efficacy or safety of therapy (less radiation energy and intensity), and therefore, will increase the drug's therapeutic efficiency.

Radiation of suitable energy is used to excite the PA drug molecules (e.g., aminolevulinic acid (ALA), porphyrins) and make them photoactive. For example, with the PDT drug ALA, light of a HeNe laser (632.8-nm excitation) can be used for excitation. In this case the metal nanoparticles are designed to exhibit strong plasmon resonance band around 632.8 nm. The surface plasmon resonance effect amplifies the excitation light at the nanoparticles, resulting in increased photoactivation of the PA drug molecules and improved therapy efficiency. The plasmonics-enhanced mechanism can also be used with the other PEPST probes in FIGS. 2B, 2C, 2D, 2E, 2F and 2G.

Structures of Plasmonics-Active Metal Nanostructures

Plasmon resonances arise within a metallic nanoparticle from the collective oscillation of free electrons driven by an incident optical field. The plasmonic response of nanoparticles have played a role in a growing number of applications, including surface-enhanced Raman scattering (SERS), chemical sensing, drug delivery, photothermal cancer therapy and new photonic devices. The investigation and application of plasmonics nanosubstrates for SERS detection has been used by one of the present inventors for over two decades [T. Vo-Dinh, "Surface-Enhanced Raman Spectroscopy Using Metallic Nanostructures," *Trends in Anal. Chem.*, 17, 557 (1998)]. The first report by one of the present inventors on the practical analytical use of the SERS techniques for trace analysis of a variety of chemicals including several homocyclic and heterocyclic polyaromatic compounds was in 1984 [T. Vo-Dinh, M. Y. K Hiromoto, G. M Begun and R. L. Moody, "*Surface-enhanced Raman spectroscopy for trace organic analysis,*" *Anal. Chem.*, vol. 56, 1667, 1984]. Since then, the development of SERS technologies for applications in chemical sensing, biological analysis and medical diagnostics has been ongoing. The substrates involve nanoparticles and semi-nanoshells comprising a layer of nanoparticles coated by a metal (such as silver) on one side (nanocaps or half-shells). Several groups have shown that plasmon resonances of spherical shells can be tuned by controlling the shell thickness and aspect ratios of the nanoshell structures [M. M Kerker, *Acc. Chem. Res.*, 17, 370 (1984); J. B. Jackson, S. L. Westcott, L. R. Hirsch, J L. West and N. H. Halas, "*Controlling the surface enhanced Raman effect via the nanoshell geometry,*" *Appl. Phys. Lett.*, vol. 82, 257-259, 2003; S. J. Norton and T Vo-Dinh, "*Plasmonic Resonances of nanoshells of Spheroidal Shape*", *IEEE Trans. Nanotechnology,* 6, 627-638 (2007)]. These shells typically comprise a metallic layer over a dielectric core. In one embodiment of the present invention, these shells comprise spheroidal shells, since the plasmon resonances (both longitudinal and transverse modes) are influenced by both shell thickness and aspect ratio. A number of researchers have examined the plasmonic response of the solid spheroidal particle in their analysis of surface-enhanced Raman scattering, although the spheroidal shell appears not to have been investigated. The present invention also includes prolate and oblate spheroidal shells, which show some interesting qualitative features in their plasmon resonances. The spheroidal shell presents two degrees of freedom for tuning: the shell thickness and the shell aspect ratio [S. J Norton and T Vo-Dinh, "*Plasmonic Resonances of Nanoshells of Spheroidal Shape*", *IEEE Trans. Nanotechnology,* 6, 627-638 (2007)].

Figure 4:
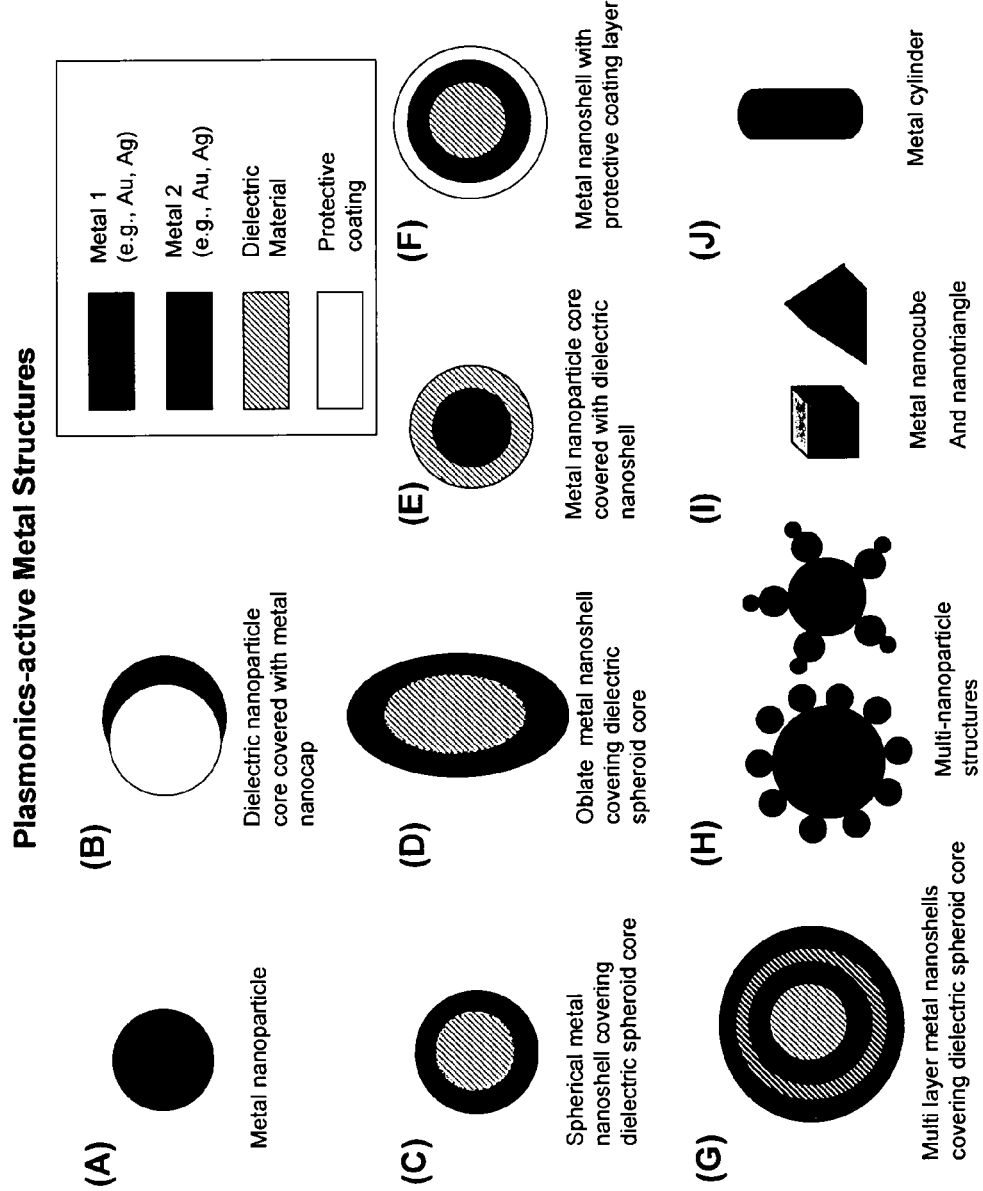
FIG. 4 provides representative embodiments of plasmonics-active nanostructures.

FIG. 4 shows some of the various embodiments of plasmonics-active nanostructures that can be designed, and are preferred embodiments of the present invention:
- (A) Metal nanoparticle;
- (B) Dielectric nanoparticle core covered with metal nanocap;
- (C) Spherical metal nanoshell covering dielectric spheroid core;
- (D) Oblate metal nanoshell covering dielectric spheroid core;
- (E) Metal nanoparticle core covered with dielectric nanoshell;
- (F) Metal nanoshell with protective coating layer;
- (G) Multi layer metal nanoshells covering dielectric spheroid core;
- (H) Multi-nanoparticle structures;
- (I) Metal nanocube and nanotriangle/nanoprism; and
- (J) Metal cylinder.

PEPST Probes with Remotely-Activated Drug Release

Figure 5:
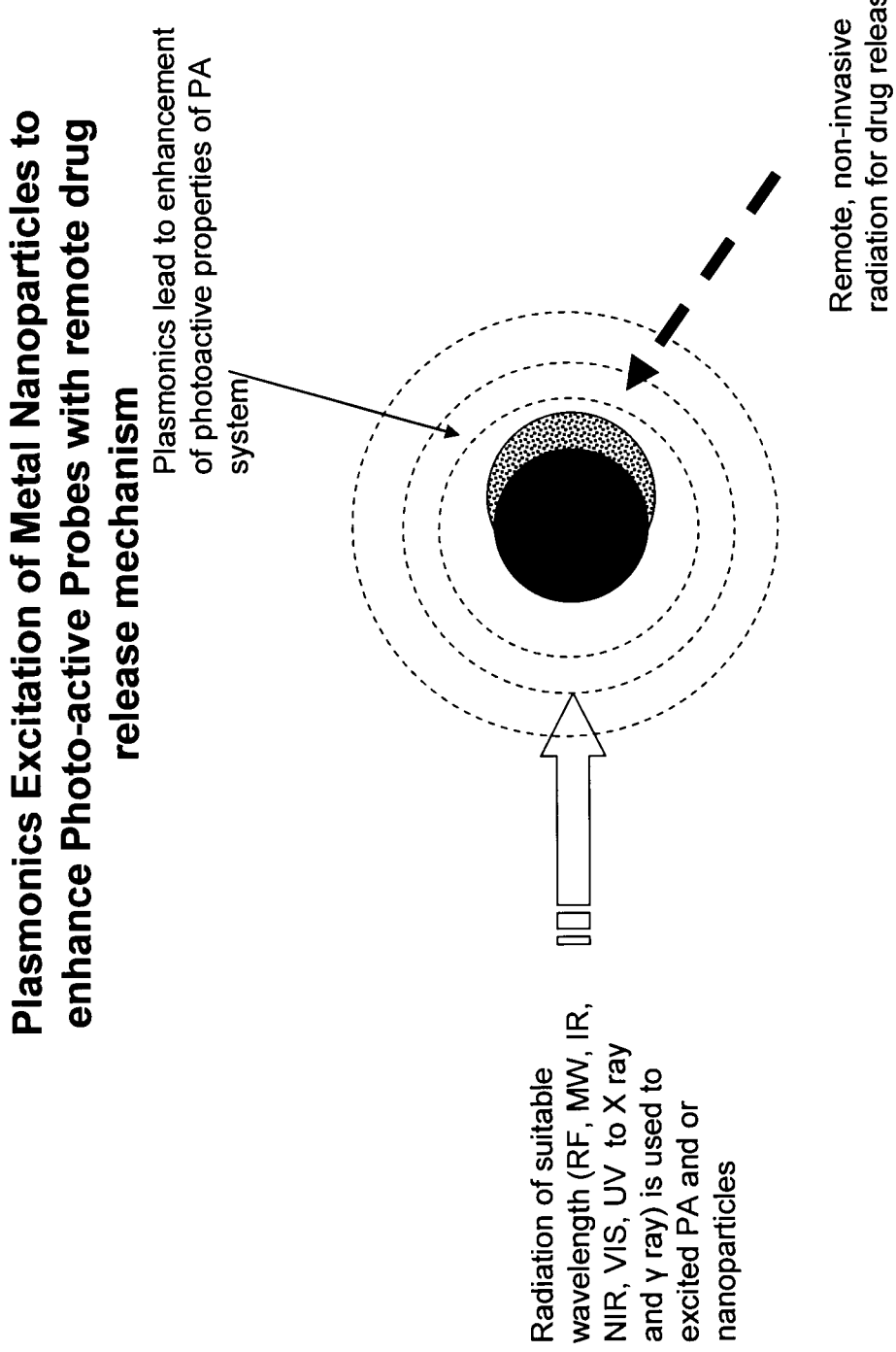
FIG. 5 is a graphical representation of one embodiment of a PEPST probe with remote drug release.

In a further embodiment of the present invention, the PA drug molecules can be incorporated into a material (e.g., biocompatible polymer) that can form a nanocap onto the metal (gold) nanoparticles. The material can be a gel or biocompatible polymer that can have long-term continuous drug release properties. Suitable gel or biocompatible polymers include, but are not limited to poly(esters) based on polylactide (PLA), polyglycolide (PGA), polycarpolactone (PCL), and their copolymers, as well as poly(hydroxyalkanoate)s of the PHB-PHV class, additional poly(ester)s, natural polymers, particularly, modified poly(saccharide)s, e.g., starch, cellulose, and chitosan, polyethylene oxides, poly(ether)(ester) block copolymers, and ethylene vinyl acetate copolymers. The drug release mechanism can also be triggered by non-invasive techniques, such as RF, MW, ultrasound, photon (FIG. 5).

Figure 6:
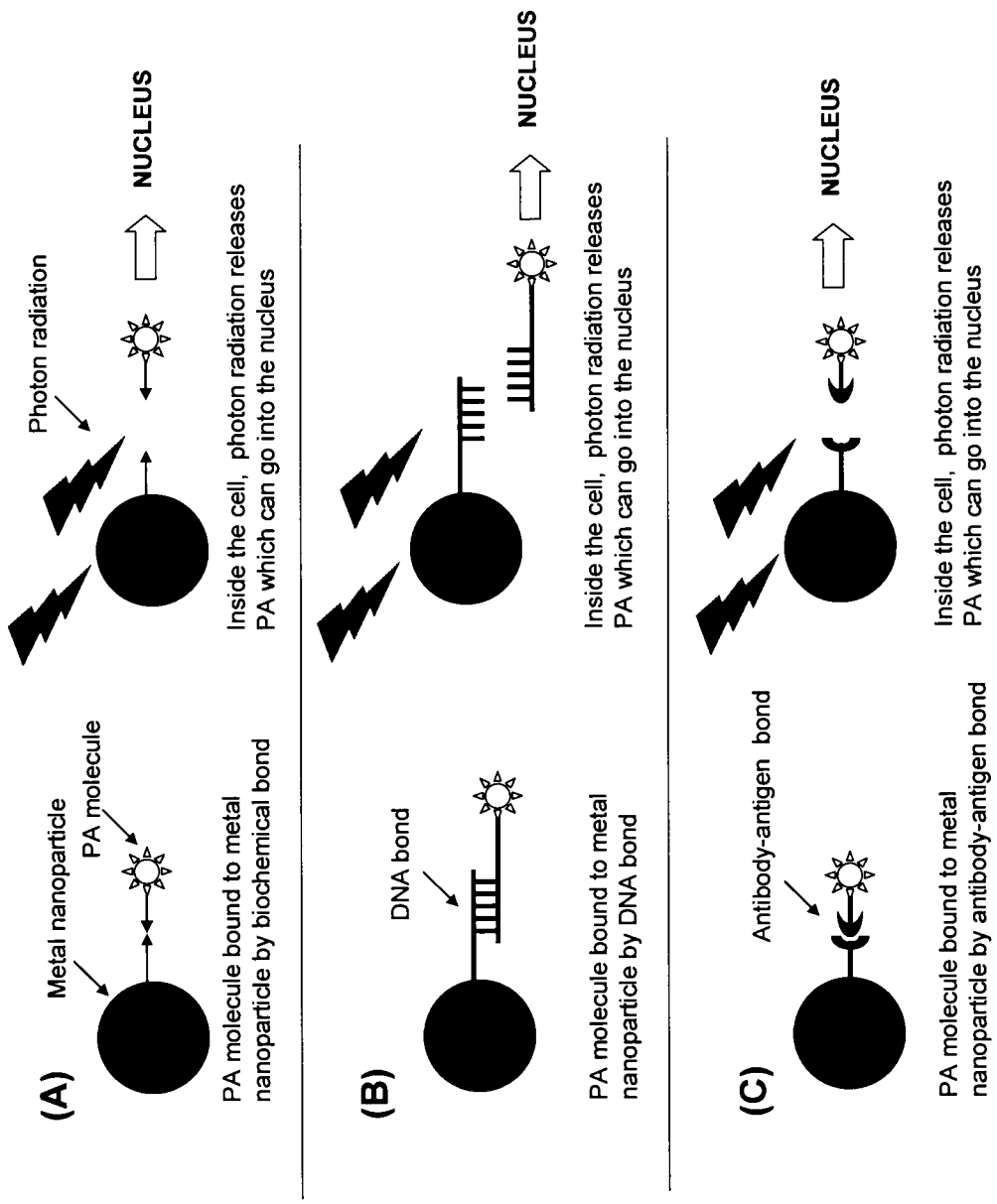
FIG. 6 is a graphical representation of several embodiments of PEPST probes with various linkers for remote drug release.

FIG. 6 shows other possible embodiments where the PA drug molecule is bound to the metal nanoparticles via a linker that can be cut by a photon radiation. Such a linker includes, but is not limited to, a biochemical bond (FIG. 6A), a DNA bond (FIG. 6B), or an antibody-antigen bond (FIG. 6C). In another embodiment, the linker is a chemically labile bond that will be broken by the chemical environment inside the cell. These types of probes are useful for therapy modalities where the PA molecules have to enter the nucleus (e.g., psoralen molecules need to enter the nucleus of cells and intercalate onto DNA). Since it is more difficult for metal nanoparticles to enter the cell nucleus than for smaller molecules, it is desirable to PEPST probes that have releasable PA molecules.

Disease-Targeted PEPST Probes

Aggregation of metal (such as silver or gold) nanoparticles (nanopsheres, nanorods, etc) is often a problem, especially with citrate-capped gold nanospheres, cetyl trimethylammonium bromide (CTAB)-capped gold nanospheres and nanorods and nanoshells because they have poor stability when they are dispersed in buffer solution due to the aggregating effect of salt ions. The biocompatibility can be improved and nanoparticle aggregation prevented by capping the nanoparticles with polyethylene glycol (PEG) (by conjugation of thiol-functionalized PEG with metal nanoparticles). Furthermore, PEGylated nanoparticles are preferentially accumulated into tumor tissues due to the enhanced permeability and retention effect, known as the "EPR" effect [Maedaa H, Fanga J. Inutsukaa T. Kitamoto Y (2003) *Vascular permeability enhancement in solid tumor: various factors, mechanisms involved and its implications. Int Immunopharmacol* 3:319-328; Paciotti G F, Myer L, Weinreich D, Goia D, Pavel N. McLaughlin R E, Tamarkin L (2004) *Colloidal gold: a novel nanoparticles vector for tumor directed drug delivery. Drug Deliv* 11:169-183]. Blood vessels in tumor tissue are more "leaky" than in normal tissue, and as a result, particles, or large macromolecular species or polymeric species preferentially extravasate into tumor tissue. Particles and large molecules tend to stay a longer time in tumor tissue due to the decreased lymphatic system, whereas they are rapidly cleared out in normal tissue. This tumor targeting strategy is often referred to as passive targeting whereas the antibody-targeting strategy is called active targeting.

To specifically target diseased cells, specific genes or protein markers, the drug systems of the present invention can be bound to a bioreceptor (e.g., antibody, synthetic molecular imprint systems, DNA, proteins, lipids, cell-surface receptors, aptamers, etc.). Immunotargeting modalities to deliver PA agents selectively to the diseased cells and tissue provide efficient strategies to achieving specificity, minimizing non-specific injury to healthy cells, and reducing the radiation intensity used. Biofunctionalization of metal nanoparticles (e.g., gold, silver) can be performed using commonly developed and widely used procedures. There are several targeting strategies that can be used in the present invention: (a) nanoparticles conjugated to antibodies that recognize biomarkers specific to the diseased cells; (b) nanoparticles passivated by poly(ethylene) glycol (PEG), which is used to increase the biocompatibility and biostability of nanoparticles and impart them an increased blood retention time.

PEPST Probes with Bioreceptors

Figure 7:
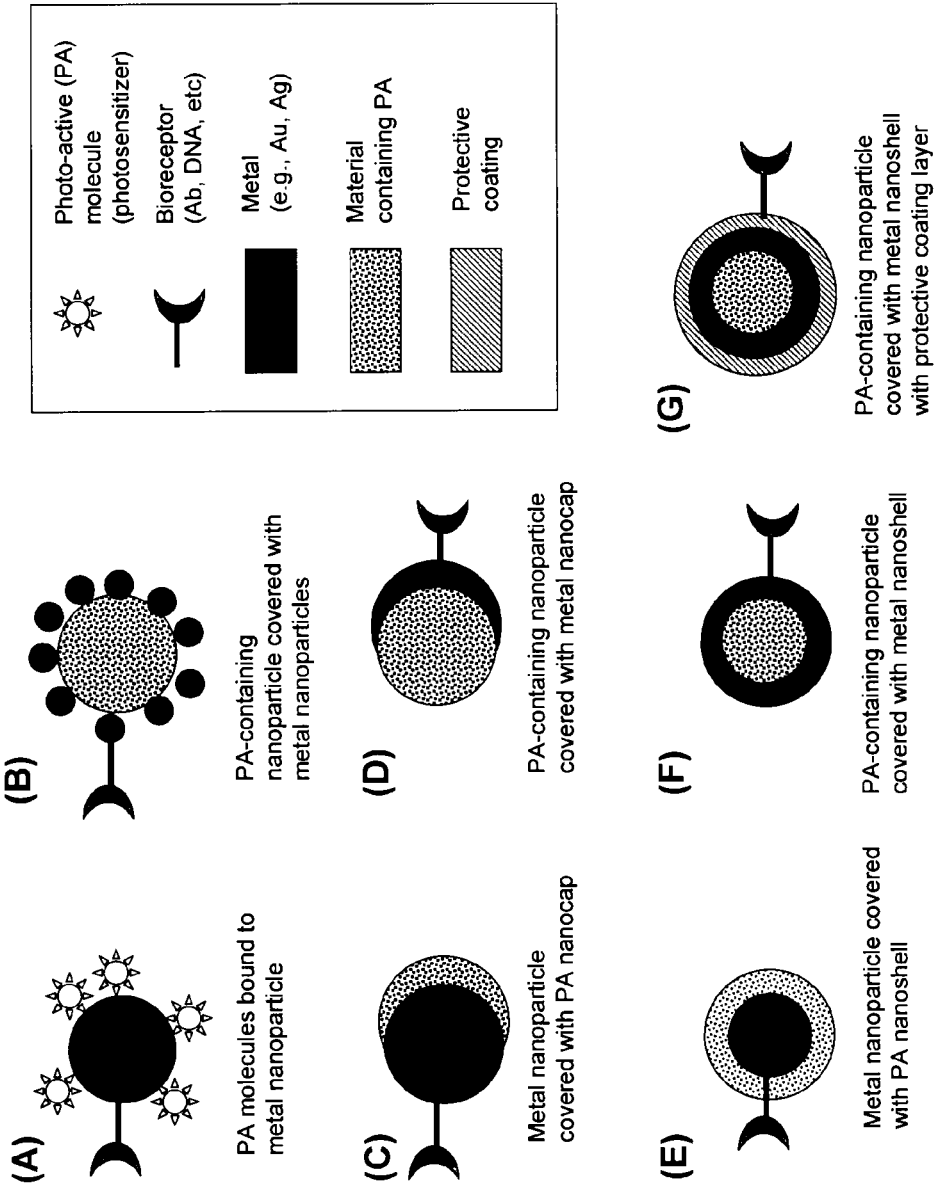
FIG. 7 is a graphical representation of several embodiments of plasmonics photo-active probes with bioreceptors.

Bioreceptors are the key to specificity for targeting disease cells, mutated genes or specific biomarkers. They are responsible for binding the biotarget of interest to the drug system for therapy. These bioreceptors can take many forms and the different bioreceptors that have been used are as numerous as the different analytes that have been monitored using biosensors. However, bioreceptors can generally be classified into five different major categories. These categories include: 1) antibody/antigen, 2) enzymes, 3) nucleic acids/DNA, 4) cellular structures/cells and 5) biomimetic. FIG. 7 illustrates a number of embodiments of the various PEPST probes with bioreceptors that can be designed. The probes are similar to those in FIG. 2 but have also a bioreceptor for tumor targeting.

Antibody Probes. Antibody based targeting is highly active, specific and efficient. The antibodies are selected to target a specific tumor marker (e.g., anti-epidermal growth factor receptor (EGFR) antibodies targeted against overexpressed EGFR on oral and cervical cancer cells; anti-Her2 antibodies against overexpressed Her2 on breast cancer cells) Antibodies are biological molecules that exhibit very specific binding capabilities for specific structures. This is very important due to the complex nature of most biological systems. An antibody is a complex biomolecule, made up of hundreds of individual amino acids arranged in a highly ordered sequence. For an immune response to be produced against a particular molecule, a certain molecular size and complexity are necessary: proteins with molecular weights greater then 5000 Da are generally immunogenic. The way in which an antigen and its antigen-specific antibody interact may be understood as analogous to a lock and key fit, by which specific geometrical configurations of a unique key enables it to open a lock. In the same way, an antigen-specific antibody "fits" its unique antigen in a highly specific manner. This unique property of antibodies is the key to their usefulness in immunosensors where only the specific analyte of interest, the antigen, fits into the antibody binding site.

DNA Probes. The operation of gene probes is based on the hybridization process. Hybridization involves the joining of a single strand of nucleic acid with a complementary probe sequence. Hybridization of a nucleic acid probe to DNA biotargets (e.g., gene sequences of a mutation, etc) offers a very high degree of accuracy for identifying DNA sequences complementary to that of the probe. Nucleic acid strands tend to be paired to their complements in the corresponding double-stranded structure. Therefore, a single-stranded DNA molecule will seek out its complement in a complex mixture of DNA containing large numbers of other nucleic acid molecules. Hence, nucleic acid probe (i.e., gene probe) detection methods are very specific to DNA sequences. Factors affecting the hybridization or reassociation of two complementary DNA strands include temperature, contact time, salt concentration, and the degree of mismatch between the base pairs, and the length and concentration of the target and probe sequences.

Biologically active DNA probes can be directly or indirectly immobilized onto a drug system, such as the energy modulation agent system (e.g., gold nanoparticle, a semiconductor, quantum dot, a glass/quartz nanoparticles, etc.) surface to ensure optimal contact and maximum binding. When immobilized onto gold nanoparticles, the gene probes are stabilized and, therefore, can be reused repetitively. Several methods can be used to bind DNA to different supports. The method commonly used for binding DNA to glass involves silanization of the glass surface followed by activation with carbodiimide or glutaraldehyde. The silanization methods have been used for binding to glass surfaces using 3 glycidoxypropyltrimethoxysilane (GOP) or aminopropyltrimethoxysilane (APTS), followed by covalently linking DNA via amino linkers incorporated either at the 3' or 5' end of the molecule during DNA synthesis.

Enzyme Probes. Enzymes are often chosen as bioreceptors based on their specific binding capabilities as well as their catalytic activity. In biocatalytic recognition mechanisms, the detection is amplified by a reaction catalyzed by macromolecules called biocatalysts. With the exception of a small group of catalytic ribonucleic acid molecules, all enzymes are proteins. Some enzymes require no chemical groups other than their amino acid residues for activity. Others require an additional chemical component called a cofactor, which may be either one or more inorganic ions, such as $Fe^{2+}$, $Mg^{2+}$, $Mn^{2+}$, or $Zn^{2+}$, or a more complex organic or metalloorganic molecule called a coenzyme. The catalytic activity provided by enzymes allows for much lower limits of detection than would be obtained with common binding techniques. The catalytic activity of enzymes depends upon the integrity of their native protein conformation. If an enzyme is denatured, dissociated into its subunits, or broken down into its component amino acids, its catalytic activity is destroyed. Enzyme-coupled receptors can also be used to modify the recognition mechanisms.

PEGylated-Vectors for PEPST Probes

The synthesis of these particles was first reported by Michael Faraday, who, in 1857, described the chemical process for the production of nanosized particles of Au0 from gold chloride and sodium citrate (Faraday 1857). Initial formulations of the vector, manufactured by binding only TNF to the particles, were less toxic than native TNF and effective in reducing tumor burden in a murine model. Subsequent studies revealed that the safety of this vector was primarily due to its rapid uptake and clearance in the RES. This vector was reformulated to include molecules of thiol-derivatized polyethylene glycol (PEG-THIOL) that were bound with molecules of TNF on the gold nanoparticles surface. The new vector, PT-cAu-TNF, avoids detection and clearance by the RES, and actively and specifically sequesters TNF within a solid tumor. The altered biodistribution correlated to improvements. In the present invention, a preferred embodiment includes the use of PEGylated-Au nanoparticles-PA drug systems to avoid detection and clearance by the RES.

Immobilization of Biomolecules to Metal Nanoparticles

The immobilization of biomolecules (PA molecules, drugs, proteins, enzymes, antibodies, DNA, etc.) to a solid support can use a wide variety of methods published in the literature. Binding can be performed through covalent bonds taking advantage of reactive groups such as amine ($—NH_2$) or sulfide (—SH) that naturally are present or can be incorporated into the biomolecule structure. Amines can react with carboxylic acid or ester moieties in high yield to form stable amide bonds. Thiols can participate in maleimide coupling, yielding stable dialkylsulfides.

A solid support of interest in the present invention is the metal (preferably gold or silver) nanoparticles. The majority of immobilization schemes involving metal surfaces, such as gold or silver, utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface, with lengths of the alkyl group from 4 to 20 carbons being preferred. For example, in the case for DNA hybridization this has been shown to displace non-specifically adsorbed HS-(CH2)-6-ss-DNA and reorient chemically attached HS-(CH2)-6-ss-DNA in such a way to make the majority of surface bound probes accessible for hybridization (M. Culha, D. L. Stokes, an dT. Vo-Dinh, "Surface-Enhanced Raman Scattering for Cancer Diagnostics: Detection of the BLC2 Gene," Expert Rev. Mol. Diagnostics, 3, 669-675 (2003)). Furthermore, to avoid direct, non-specific DNA adsorption onto the surface, alkylthiols have been used to block further access to the surface, allowing only covalent immobilization through the linker [Steel, A. B.; Heme, T. M.; Tarlov, M. J. Anal. Chem. 1998, 70, 4670-7; Heme, T. M.; Tarlov, M. J. J. Am. Chem. Soc. 1997, 119, 8916-20]

There are many methods related to the preparation of stable oligonucleotide conjugates with gold particles by using thiol-functionalized biomolecules that had previously been shown to form strong gold-thiol bonds. Oligonucleotides with 5'-terminal alkanethiol functional groups as anchors can be bound to the surface of gold nanoparticles, and the resulting labels were robust and stable to both high and low temperature conditions [R. Elghanian, J. J. Storhoff, R. C. Mucic, R. L. Letsinger and C. A. Mirkin, *Selective colorimetric detection of polynucleotides based on the distance-dependent optical properties of gold nanoparticles. Science* 277 (1997), pp. 1078-1081]. A cyclic dithiane-epiandrosterone disulfide linker has been developed for binding oligonucleotides to gold surfaces [R. Elghanian, J. J. Storhoff, R. C. Mucic, R. L. Letsinger and C. A. Mirkin, *Selective colorimetric detection of polynucleotides based on the distance-dependent optical properties of gold nanoparticles. Science* 277 (1997), pp. 1078-1081]. Li et al. have reported a trithiol-capped oligonucleotide that can stabilize gold metal nanoparticles having diameters ≥100 nm, while retaining hybridization properties that are comparable to acyclic or dithiol-oligonucleotide modified particles [Z. Li, R. C. Jin, C. A. Mirkin and R. L. Letsinger, *Multiple thiol-anchor capped DNA-gold nanoparticle conjugates. Nucleic Acids Res.* 30 (2002), pp. 1558-1562].

In general silver nanoparticles cannot be effectively passivated by alkylthiol-modified oligonucleotides using the established experimental protocols that were developed for gold particles. A method of generating core-shell particles comprising a core of silver and a thin shell of gold has allowed silver nanoparticles to be readily functionalized with alkylthiol-oligonucleotides using the proven methods used to prepare pure gold particle-oligonucleotide conjugates. [Y. W. Cao, R. Jin and C. A. Mirkin, *DNA-modified core-shell Ag/Au nanoparticles. J. Am. Chem. Soc.* 123 (2001), pp. 7961-7962].

To facilitate the use of biomolecule-conjugated plasmonics-active nanoprobes (PAN) it is important that the recognition region of the biomolecule is fully accessible to the bio-target. Commonly a polynucleotide extension sequence is incorporated to serve as a spacer between the PAN and the oligonucleotide recognition region. To achieve high sensitivity and selectivity in assays based on DNA hybridization it is important that the PAN label colloidal solution is stable. Recently, Storhoff et al. [J. J. Storhoff, R. Elghanian, C. A. Mirkin and R. L. Letsinger, *Sequence-dependent stability of DNA-modified gold nanoparticles. Langmuir* 18 (2002), pp. 6666-6670] have shown that the base composition of the oligonucleotide has a significant effect on colloid stability and on oligonucleotide surface coverage. Otsuka et al. have used a heterobifunctional thiol-PEG (polyethylene glycol) derivative as a linker to stabilize gold PRPs [H. Otsuka, Y. Akiyama, Y Nagasaki and K Kataoka, *Quantitative and reversible lectin-induced association of gold nanoparticles modified with* α*-lactosyl*-ω-*mercapto-poly*(*ethylene glycol*). *J. Am. Chem. Soc.* 123 (2001), pp. 8226-8230].

Proteins are usually bound to PANs using non-covalent, passive absorption. Alternatively, a mercapto-undecanoic acid linker/spacer molecule can be used to attach NeutrAvidin covalently to gold and silver segmented nanorods [I. D. Walton, S. M. Norton, A. Balasingham, L. He, D. F. Oviso, D. Gupta, P. A. Raju, M. J. Natan and R. G. Freeman, *Particles* for multiplexed analysis in solution: detection and identification of striped metallic particles using optical microscopy. *Anal. Chem.* 74 (2002), pp. 2240-2247]. The thiol groups bind to the metal surface, and the carboxyl functional groups on the particle surface are activated using EDC and s-NHS reagents and then cross-linked to the amino groups in NeutrAvidin. The ability to fabricate core-shell particles where the core is metal and the shell is composed of latex, silica, polystyrene or other non-metal material provides a promising alternative approach to immobilizing biomolecules and engineering particle surfaces [T. K. Mandal, M. S. Fleming and D. R. Walt, *Preparation of polymer coated gold nanoparticles by surface-confined living radical polymerization at ambient temperature. Nano Letters* 2 (2002), pp. 3-7; S. O. Obare, N. R. Jana and C. J Murphy, *Preparation of polystyrene- and silica-coated gold nanorods and their use as templates for the synthesis of hollow nanotubes. Nano Letters* 1 (2001), pp. 601-603; C. Radloff and N. J. Halas, *Enhanced thermal stability of silica-encapsulated metal nanoshells. Appl. Phys. Lett.* 79 (2001), pp. 674-676; L. Quaroni and G. Chumanov, *Preparation of polymer-coated functionalized silver nanoparticles. J. Am. Chem. Soc.* 121 (1999), pp. 10642-10643p; F. Caruso, *Nanoengineering of particle surfaces. Adv. Mater.* 13 (2001), pp. 11-22].

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold [Burges, J. D.; Hawkridge, F. M. Langmuir 1997, 13, 3781-6]. After self-assembled monolayer (SAM) formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Successful coupling procedures include, but are not limited to:

Binding Procedure Using N-Hydroxysuccinimide (NHS) and its Derivatives

The coupling approach involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [Boncheva, M.; Scheibler, L.; Lincoln, P.; Vogel, H.; Akerman, B. Langmuir 1999, 15, 4317-20]. NHS reacts almost exclusively with primary amine groups. Covalent immobilization can be achieved in as little as 30 minutes. Since $H_2O$ competes with $-NH_2$ in reactions involving these very labile esters, it is important to consider the hydrolysis kinetics of the available esters used in this type of coupling. The derivative of NHS, O—(N-succinimidyl)-N,N,N',N'-tetramethyluronium tetrafluoroborate, increases the coupling yield by utilizing a leaving group that is converted to urea during the carboxylic acid activation, hence favorably increasing the negative enthalpy of the reaction.

Binding Procedure Using Maleimide

Maleimide can be used to immobilize biomolecules through available —SH moieties. Coupling schemes with maleimide have proven useful for the site-specific immobilization of antibodies, Fab fragments, peptides, and SH-modified DNA strands. Sample preparation for the maleimide coupling of a protein involves the simple reduction of disulfide bonds between two cysteine residues with a mild reducing agent, such as dithiothreitol, 2-mercaptoethanol or tris(2-carboxyethyl)phosphine hydrochloride. However, disulfide reduction will usually lead to the protein losing its natural conformation, and might impair enzymatic activity or antibody recognition. The modification of primary amine groups with 2-iminothiolane hydrochloride (Traut's reagent) to introduce sulfhydryl groups is an alternative for biomolecules lacking them. Free sulfhydryls are immobilized to the maleimide surface by an addition reaction to unsaturated carbon-carbon bonds [Jordan, C. E., et al., 1997].

Binding Procedure Using Carbodiimide.

Surfaces modified with mercaptoalkyldiols can be activated with 1,1'-carbonyldiimidazole (CDI) to form a carbonylimidazole intermediate. A biomolecule with an available amine group displaces the imidazole to form a carbamate linkage to the alkylthiol tethered to the surface [Potyrailo, R. A., et al., 1998].

Other Experimental Procedures to Conjugate Biomolecules to Metal (e.g., Silver, Gold) Nanoparticles.

In one preferred embodiment, nanoparticles of metal colloid hydrosols are prepared by rapidly mixing a solution of $AgNO_3$ with ice-cold $NaBH_4$. For developing a SMP probes, a DNA segment is bound to a nanoparticle of silver or gold. The immobilization of biomolecules (e.g., DNA, antibodies, enzymes, etc.) to a solid support through covalent bonds usually takes advantage of reactive groups such as amine ($-NH_2$) or sulfide ($-SH$) that naturally are present or can be incorporated into the biomolecule structure. Amines can react with carboxylic acid or ester moieties in high yield to form stable amide bonds. Thiols can participate in maleimide coupling yielding stable dialkylsulfides.

In one preferred embodiment, silver nanoparticles are used. In one preferred embodiment, the immobilization schemes involving Ag surfaces utilize a prior derivatization of the surface with alkylthiols, forming stable linkages are used. Alkylthiols readily form self-assembled monolayers (SAM) onto silver surfaces in micromolar concentrations. The terminus of the alkylthiol chain can be directly used to bind biomolecules, or can be easily modified to do so. The length of the alkylthiol chain was found to be an important parameter, keeping the biomolecules away from the surface. Furthermore, to avoid direct, non-specific DNA adsorption onto the surface, alkylthiols were used to block further access to the surface, allowing only covalent immobilization through the linker.

Silver/gold surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold.

After SAM formation on silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. In one embodiment, more active intermediate (labile ester) is first formed with the carboxylic acid moiety and in a later stage reacted with the free amine, increasing the coupling yield. Successful coupling procedures include:

The coupling approach used to bind DNA to a silver nanoparticle involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [4]. NHS reacts almost exclusively with primary amine groups. Covalent immobilization can be achieved in as little as 30 minutes. Since $H_2O$ competes with —$NH_2$ in reactions involving these very labile esters, it is important to consider the hydrolysis kinetics of the available esters used in this type of coupling. The derivative of NHS used, O—(N-succinimidyl)-N,N,N', N'-tetramethyluronium tetrafluoroborate, increases the coupling yield by utilizing a leaving group that is converted to urea during the carboxylic acid activation, hence favorably increasing the negative enthalpy of the reaction.

Spectral Range of Light Used for PEPST

A plasmonics enhanced effect can occur throughout the electromagnetic region provided the suitable nanostructures, nanoscale dimensions, metal types are used. Therefore, the PEPST concept is valid for the entire electromagnetic spectrum, i.e, energy, ranging from gamma rays and X rays throughout ultraviolet, visible, infrared, microwave and radio frequency energy. However, for practical reasons, visible and NIR light are used for silver and gold nanoparticles, since the plasmon resonances for silver and gold occur in the visible and NIR region, respectively. Especially for gold nanoparticles, the NIR region is very appropriate for non-invasive therapy.

Photon Excitation in the Therapeutic Window of Tissue

Figure 8:
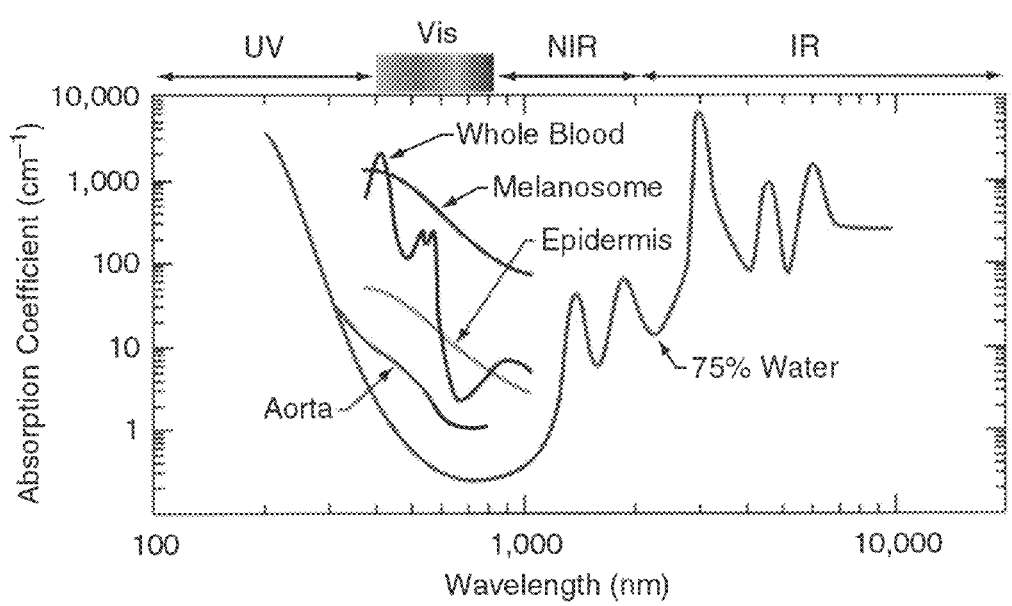
FIG. 8 is a graphical representation of the "therapeutic window" in tissue and absorption spectra of biological components.

There are several methods using light to excite photoactivate compounds non-invasively. We can use light having wavelengths within the so-called "therapeutic window" (700-1300 nm). The ability of light to penetrate tissues depends on absorption. Within the spectral range known as the therapeutic window (or diagnostic window), most tissues are sufficiently weak absorbers to permit significant penetration of light. This window extends from 600 to 1300 nm, from the orange/red region of the visible spectrum into the NIR. At the short-wavelength end, the window is bound by the absorption of hemoglobin, in both its oxygenated and deoxygenated forms. The absorption of oxygenated hemoglobin increases approximately two orders of magnitude as the wavelength shortens in the region around 600 nm. At shorter wavelengths many more absorbing biomolecules become important, including DNA and the amino acids tryptophan and tyrosine. At the infrared (IR) end of the window, penetration is limited by the absorption properties of water. Within the therapeutic window, scattering is dominant over absorption, and so the propagating light becomes diffuse, although not necessarily entering into the diffusion limit. FIG. 8 shows a diagram of the therapeutic window of tissue. The following section discusses the use of one-photon and multi-photon techniques for therapy.

Light Excitation Methods: Single-Photon and Multi-Photon Excitation

Two methods can be used, one-photon or multi-photon excitation. If the two-photon technique is used, one can excite the PA molecules with light at 700-1000 nm, which can penetrate deep inside tissue, in order to excite molecules that absorb in the 350-500 nm spectral region. This approach can excite the psoralen compounds, which absorb in the 290-350 nm spectral region and emit in the visible. With the one-photon method, the photo-activator (PA) drug molecules can directly absorb excitation light at 600-1300 nm. In this case we can design a psoralen-related system (e.g., psoralens having additional aromatic rings or other conjugation to alter the ability to absorb at different wavelengths) or use other PA systems: photodynamic therapy drugs, ALA, etc.

PEPST Modality for Photopheresis Using X ray Excitation Need for X-Ray Excitation Photopheresis has been demonstrated to be an effective treatment for a number of diseases. However, there is a strong need to develop non-invasive modalities where the excitation light can directly irradiate the photoactive compounds without the need for removal and reinfusion of blood from patients. One method for an improved and practical modality for such therapy was described in U.S. Ser. No. 11/935,655, filed Nov. 6, 2007, the entire contents of which are hereby incorporated by reference.

Although X-ray can excite compounds in deep tissue non-invasively, X-ray is not easily absorbed by organic drug compounds. The present invention provides a solution to that problem, by the providing of a molecular system that can absorb the X-ray energy and change that energy into other energies that can be used to activate drug molecules. More specifically, the molecular system that can absorb and change the X-ray energy in the present invention is the PEPST probes comprising nanoparticles.

Figure 9:
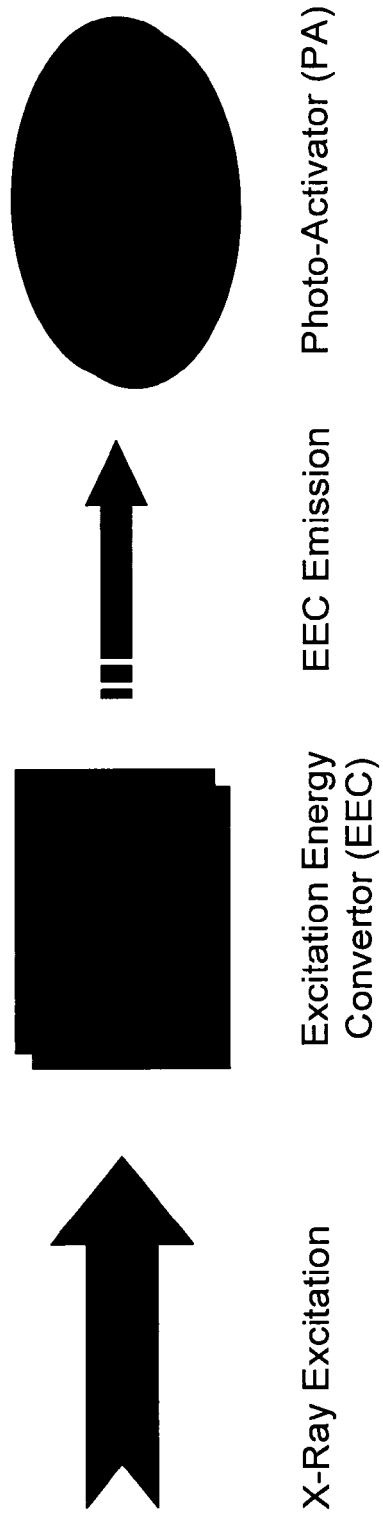
FIG. 9 is a graphical representation of an embodiment of the energy modulation agent (or excitation energy converter/EEC)-photo activator (PA) system of the present invention.

In this embodiment, the present invention uses X-rays for excitation. The advantage is the ability to excite molecules non-invasively since X-ray can penetrate deep in tissue. However, the limitation is the fact that X-ray does not interact with most molecules. In one embodiment of the present invention, the drug molecule (or PA) is bound to a molecular entity, referred to as an "energy modulation agent" that can interact with the X-rays, and then emit light that can be absorbed by the PA drug molecules. (FIG. 9)

PEPST Probes for X Ray Excitation

In the previous sections, the advantage of gold nanoparticles as plasmonics-active systems have been discussed. Furthermore, gold nanoparticles are also good energy modulation agent systems since they are biocompatible and have been shown to be a possible candidate for contrast agents for X-ray [Hainfeld et al, *The British Journal of radiology*, 79, 248, 2006]. The concept of using high-Z materials for dose enhancement in cancer radiotherapy was advanced over 20 years ago. The use of gold nanoparticles as a dose enhancer seems more promising than the earlier attempts using microspheres and other materials for two primary reasons. First, gold has a higher Z number than iodine (I, Z=53) or gadolinium (Gd, Z=64), while showing little toxicity, up to at least 3% by weight, on either the rodent or human tumour cells. The gold nanoparticles were non-toxic to mice and were largely cleared from the body through the kidneys. This novel use of small gold nanoparticles permitted achievement of the high metal content in tumours necessary for significant high-Z radioenhancement [James F Hainfeld, Daniel N Slatkin and Henry M Smilowitz, *The use of gold nanoparticles to enhance radiotherapy in mice, Phys. Med. Biol.* 49 (2004)]

Delivering a lethal dose of radiation to a tumor while minimizing radiation exposure of nearby normal tissues remains the greatest challenge in radiation therapy. The dose delivered to a tumour during photon-based radiation therapy can be enhanced by loading high atomic number (Z) materials such as gold (Au, Z=79) into the tumor, resulting in greater photoelectric absorption within the tumor than in surrounding tissues. Thus, gold clearly leads to a higher tumor dose than either iodine or gadolinium. Second, nanoparticles provide a better mechanism than microspheres, in terms of delivering high-Z materials to the tumor, overcoming some of the difficulties found during an earlier attempt using gold microspheres [Sang Hyun Cho, *Estimation of tumour dose enhancement due to gold nanoparticles during typical radiation treatments: a preliminary Monte Carlo study, Phys. Med. Biol.* 50 (2005)]

Gold (or metal) complexes with PA ligands: Gold (or metal) complexes with PA can preferably be used in the present invention. The metal can be used as an energy modulation agent system. For example, gold complexes with psoralen-related ligands can be used as a hybrid energy modulation agent-PA system. The gold molecules serve as the energy modulation agent system and the ligand molecules serve as the PA drug system. Previous studies indicated that gold(I) complexes with diphosphine and bipyridine ligands exhibit X-ray excited luminescence [Ref. 3: Kim et al, *Inorg. Chem.*, 46, 949, 2007].

Figure 10:
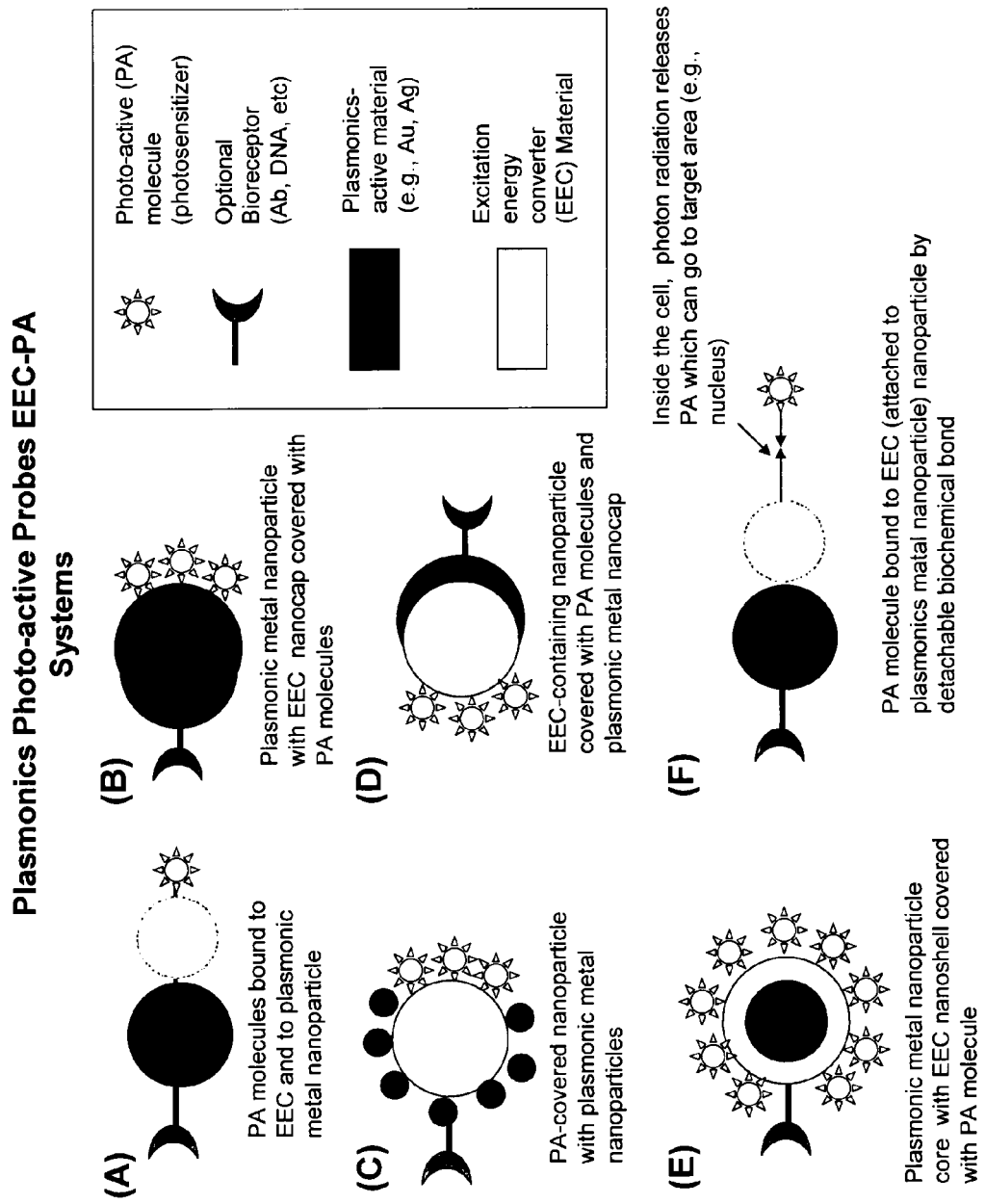
FIG. 10 is a graphical representation of several embodiments of plasmonics photo-active energy modulation agent-PA probes.

FIG. 10 shows a number of the various embodiments of PEPST probes that can be preferably used for X ray excitation of energy modulation agent-PA system. These probes comprise:
- (A) PA molecules bound to energy modulation agent and to plasmonic metal nanoparticle;
- (B) Plasmonic metal nanoparticle with energy modulation agent nanocap covered with PA molecules;
- (C) PA-covered nanoparticle with plasmonic metal nanoparticles;
- (D) Energy modulation agent-containing nanoparticle covered with PA molecules and plasmonic metal nanocap;
- (E) Plasmonic metal nanoparticle core with energy modulation agent nanoshell covered with PA molecule; and
- (F) PA molecule bound to energy modulation agent (attached to plasmonics metal nanoparticle) nanoparticle by detachable biochemical bond.

Examples of PEPST System Based on Energy Modulation Agent-PA

For purposes of simplification, the following discussion is centered on gold as the metal material and CdS as the energy modulation agent material (which can also be used as DNA stabilized CdS, see Ma et al, *Langmuir*, 23 (26), 12783-12787 (2007)) and psoralen as the PA molecule. However, it is to be understood that many other embodiments of metal material, energy modulation agent and PA molecule are possible within the bounds of the present invention, and the following discussion is for exemplary purposes only. Suitable metals that can be used in plasmon resonating shells or other plasmon resonating structures can be include, but are not limited to, gold, silver, platinum, palladium, nickel, ruthenium, rhenium, copper, gallium, and cobalt.

In the embodiment of FIG. 10A, the PEPST system comprises gold nanoparticles, an energy modulation agent nanoparticle (e.g., CdS) linked to a PA drug molecule (e.g., psoralen). X ray is irradiated to CdS, which absorbs X rays [Hua et al, *Rev. Sci. Instrum.*, 73, 1379, 2002] and emits CdS XEOL light (at 350-400 nm) that is plasmonics-enhanced by the gold nanoparticle. This enhanced XEOL light is used to photoactivate psoralen (PA molecule). In this case the nanostructure of the gold nanoparticle is designed to enhance the XEOL light at 350-400 nm.

In the embodiment of FIG. 10B, the PEPST system comprises a plasmonics-active metal (gold) nanoparticle with energy modulation agent nanocap (CdS) covered with PA molecules (e.g., psoralen). X ray is irradiated to CdS, which absorbs X ray and emits XEOL light that is plasmonics-enhanced by the gold nanoparticle. This enhanced XEOL light is used to photoactivate psoralen (PA molecule).

In the embodiment of FIG. 10C, the PEPST system comprises a PA (e.g., psoralen)-covered CdS nanoparticle with smaller plasmonic metal (gold) nanoparticles. X ray is irradiated to CdS, which absorbs X ray and emits XEOL light that is plasmonics-enhanced by the gold nanoparticle. This enhanced XEOL light is used to photoactivate psoralen (PA molecule).

In the embodiment of FIG. 10D, the energy modulation agent core comprises CdS or CsCl nanoparticles covered with a nanocap of gold. X ray is irradiated to CdS or CsCl, which absorbs X ray [[Jaegle et al, *J. Appl. Phys.*, 81, 2406, 1997] and emits XEOL light that is plasmonics-enhanced by the gold nanocap structure. This enhanced XEOL light is used to photoactivate psoralen (PA molecule).

Similarly, the embodiment in FIG. 10E comprises a spherical gold core covered by a shell of CdS or CsCl. X ray is irradiated to CdS or CsCl material, which absorbs X ray [Jaegle et al, *J. Appl. Phys.*, 81, 2406, 1997] and emits XEOL light that is plasmonics-enhanced by the gold nanosphere. This enhanced XEOL light is used to photoactivate psoralen (PA molecule).

In the embodiment of FIG. 10F, the PEPST system comprises gold nanoparticles, and an energy modulation agent nanoparticle (e.g., CdS) linked to a PA drug molecule (e.g., psoralen) by a link that can be detached by radiation. X ray is irradiated to CdS, which absorbs X ray and emits CdS XEOL light (at 350-400 nm) that is plasmonics-enhanced by the gold nanoparticle. This enhanced XEOL light is used to photoactivate psoralen (PA molecule). In this case the nanostructure of the gold nanoparticle is designed to enhance the XEOL light at 350-400 nm.

In alternative embodiments, the metal nanoparticles or single nanoshells are replaced by multi layers of nanoshells [Kun Chen, Yang Liu, Guillermo Ameer, Vadim Backman, *Optimal design of structured nanospheres for ultrasharp light-scattering resonances as molecular imaging multilabels, Journal of Biomedical Optics*, 10(2), 024005 (March/April 2005)].

In other alternative embodiments the metal nanoparticles are covered with a layer (1-30 nm) of dielectric material (e.g. silica). The dielectric layer (or nanoshell) is designed to prevent quenching of the luminescence light emitted by the energy modulation agent (also referred to as EEC) molecule(s) due to direct contact of the metal with the energy modulation agent molecules. In yet other alternative embodiments, the energy modulation agent molecules or materials are bound to (or in proximity of) a metal nanoparticle via a spacer (linker). The spacer is designed to prevent quenching of the luminescence light emitted by the energy modulation agent molecules or materials.

Other Useable Materials

The energy modulation agent materials can include any materials that can absorb X ray and emit light in order to excite the PA molecule. The energy modulation agent materials include, but are not limited to:
- metals (gold, silver, etc);
- quantum dots;
- semiconductor materials;
- scintillation and phosphor materials;
- materials that exhibit X-ray excited luminescence (XEOL);
- organic solids, metal complexes, inorganic solids, crystals, rare earth materials (lanthanides), polymers, scintillators, phosphor materials, etc.; and
- materials that exhibit excitonic properties.

Quantum dots, semiconductor nanostructures. Various materials related to quantum dots, semiconductor materials, etc. can be used as energy modulation agent systems. For example CdS-related nanostructures have been shown to exhibit X-ray excited luminescence in the UV-visible region [Hua et al, *Rev. Sci. Instrum.*, 73, 1379, 2002].

Scintillator Materials as energy modulation agent systems. Various scintillator materials can be used as energy modulation agents since they absorb X-ray and emit luminescence emission, which can be used to excite the PA system. For example, single crystals of molybdates can be excited by X-ray and emit luminescence around 400 nm [Mirkhin et al, *Nuclear Instrum. Meth. In Physics Res. A*, 486, 295 (2002].

Solid Materials as energy modulation agent systems: Various solid materials can be used as energy modulation agents due to their X-ray excited luminescence properties. For example CdS (or CsCl) exhibit luminescence when excited by soft X-ray [Jaegle et al, *J. Appl. Phys.*, 81, 2406, 1997].

XEOL materials: lanthanides or rare earth materials and their oxides, such as $Y_2O_3$, which can also contain one or more dopants [L. Soderholm, G. K Liu, Mark R. Antonioc, F. W. Lytle, *X-ray excited optical luminescence .XEOL. detection of x-ray absorption fine structure .XAFZ, J. Chem. Phys,* 109, 6745, 1998], Masashi Ishiia, Yoshihito Tanaka and Tetsuya Ishikawa, Shuji Komuro and Takitaro Morikawa, Yoshinobu Aoyagi, *Site-selective x-ray absorption fine structure analysis of an optically active center in Er-doped semiconductor thin film using x-ray-excited optical luminescence, Appl. Phys. Lett,* 78, 183, 2001]

Figure 11:
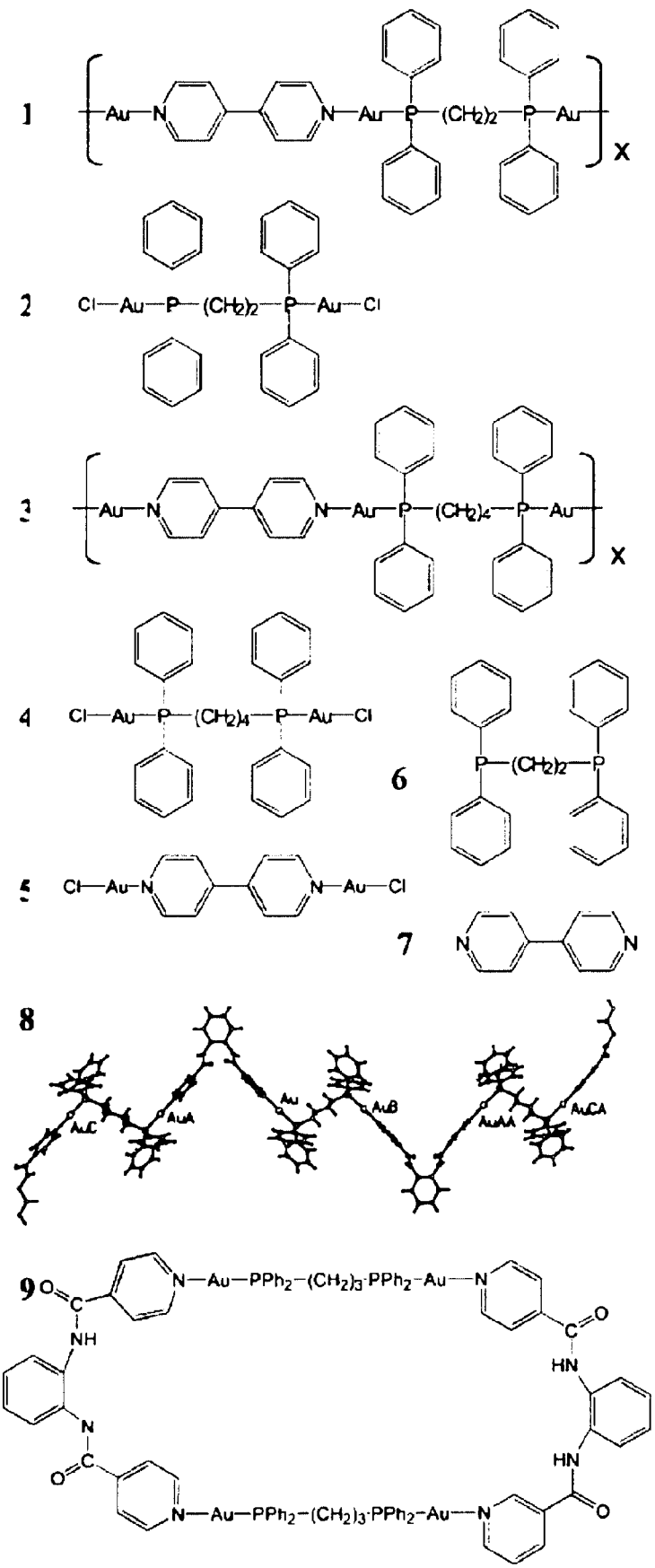
FIG. 11 shows structures of various preferred embodiments of gold complexes exhibiting XEOL.
Figure 12:
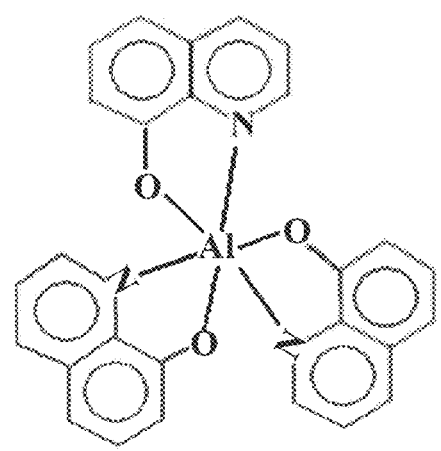
FIG. 12 shows the structure of a further embodiment of compound exhibiting XEOL, namely a tris-8-hydroxyquinoline-aluminum complex.

Some examples of metal complexes exhibiting XEOL which can be used as energy modulation agent systems are shown in FIGS. 11 and 12. Such structures can be modified by replacing the metal atom with metal nanoparticles in order to fabricate a plasmonics-enhance PEPST probe. In the present invention, the experimental parameters including size, shape and metal type of the nano structure can be selected based upon the excitation radiation (NIR or X ray excitation), the photoactivation radiation (UVB), and/or the emission process from the energy modulation agent system (visible NIR).

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention.

Further materials suitable as energy modulation agents include, but are not limited to, CdTe, CdSe, ZnO, CdS, $Y_2O_3$, MgS, CaS, SrS and BaS. Such materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\leq1$, and $0<y\leq1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq1$, $0<y\leq1$, $0<z\leq1$). Two examples of such complex compounds are $Zn_{0.4}Cd_{0.4}Mn_{0.2}S$ and $Zn_{0.9}Mn_{0.1}S_{0.8}Se_{0.2}$. Additional energy modulation materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn, Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, 0; B=S, . . . $0<z\leq1$, $o<q\leq1$).

Some nanoparticles such as $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; ZnS:Mn, $Er^{3+}$ are known in the art to function for both down-conversion luminescence and upconversion luminescence, and can thus be used in various embodiments of the present invention.

Principle of Plasmonics-Enhancement Effect of the PEPST Probe Using X-Ray Excitation One embodiment of the basic PEPST probe embodiment comprises PA molecules bound to an energy modulation agent and to plasmonic metal (gold) nanoparticles. First the metal nanoparticle can serve as a drug delivery platform (see previous discussion). Secondly, the metal nanoparticle can play 2 roles:

(1) Enhancement of the X-ray electromagnetic field
(2) Enhancement of the emission signal of the energy modulation agent system.

The X ray radiation, used to excite the energy modulation agent system, is amplified by the metal nanoparticle due to plasmon resonance. As a result the energy modulation agent system exhibits more emission light that is used to photoactivate the PA drug molecules (e.g., psoralens) and make them photoactive. In this case the metal nanoparticles are designed to exhibit strong plasmon resonance at or near the X ray wavelengths. The surface plasmon resonance effect amplifies the excitation light at the nanoparticles, resulting in increased photoactivation of the PA drug molecules and improved therapy efficiency. The plasmonics-enhanced mechanism can also be used with the other PEPST probes described above.

Figure 13:
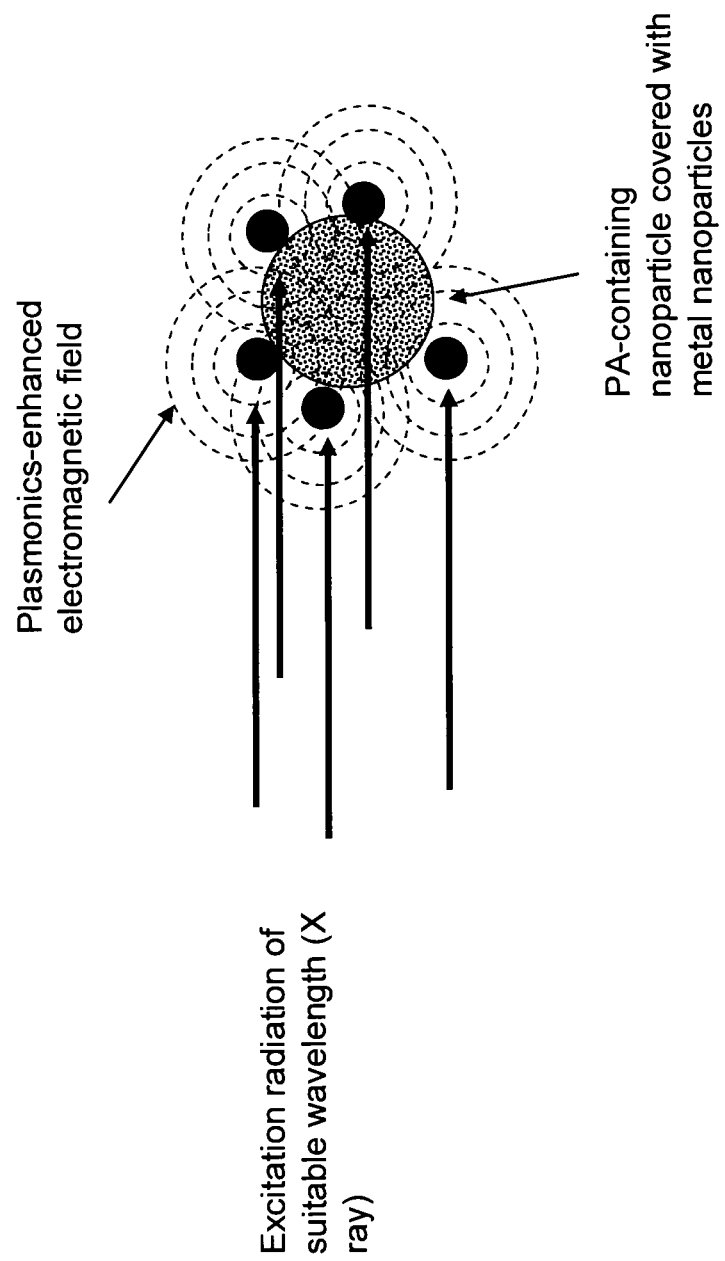
FIG. 13 is a graphical representation of a plasmonics-enhanced mechanism for a photo-active energy modulation agent-PA probe of the present invention.

FIG. 13 illustrates the plasmonics-enhancement effect of the PEPST probe. X-ray used in medical diagnostic imaging has photon energies from approximately 10 to 150 keV, which is equivalent to wavelengths range from 1.2 to 0.0083 Angstroms. [$\lambda$ (Angstrom)=12.4/E (keV)]. Soft X ray can go to 10 nm. The dimension of plasmonics-active nanoparticles usually have dimensions on the order or less than the wavelengths of the radiation used. Note that the approximate atomic radius of gold is approximately 0.15 nanometers. At the limit, for gold the smallest "nanoparticle" size is 0.14 nm (only 1 gold atom). A nanoparticle with size in the hundreds of nm will have approximately $10^6$-$10^7$ gold atoms. Therefore, the range of gold nanoparticles discussed in this invention can range from 1-$10^7$ gold atoms.

Figure 14:
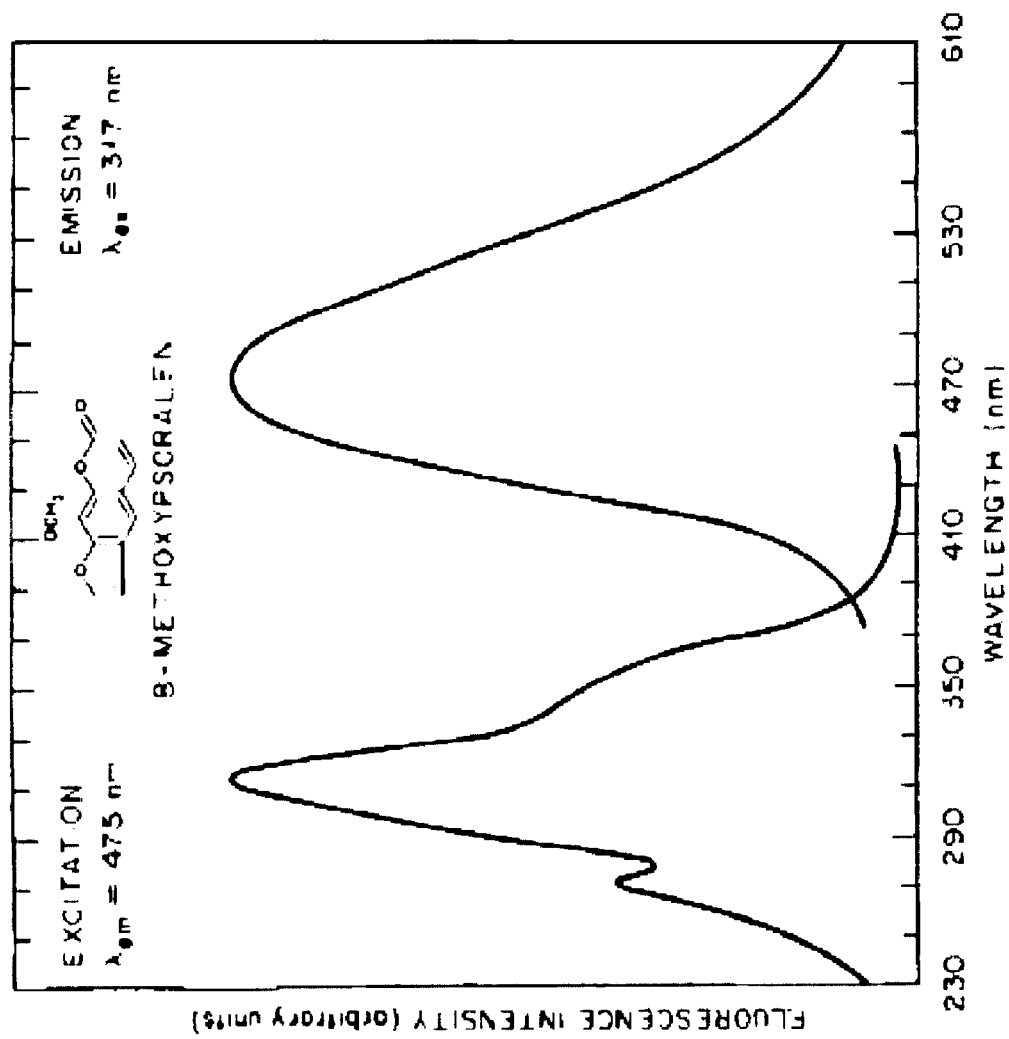
FIG. 14 is a graph showing excitation and emission fluorescence spectra of psoralens.

The gold nanoparticles can also enhance the energy modulation agent emission signal, which is use to excite the PA molecule. For psoralens, this spectral range is in the UVB region (320-400 nm). Silver or gold nanoparticles, nanoshell and nanocaps have been fabricated to exhibit strong plasmon resonance in this region. FIG. 14 shows excitation and emission fluorescence spectra of a psoralen compound (8-methoxypsoralen).

PEPST Energy Modulation Agent-PA Probe with Detachable PA.

Figure 15:
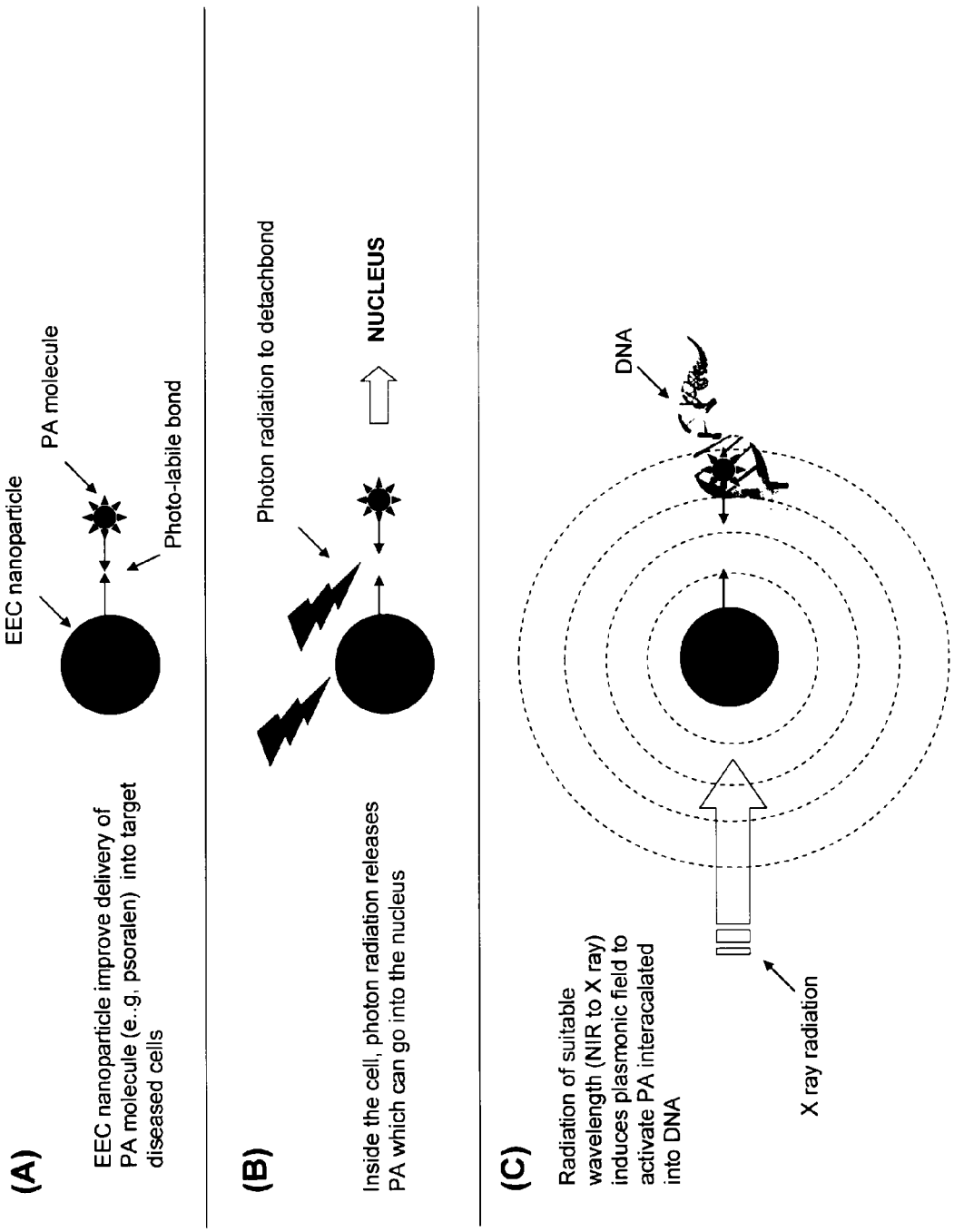
FIG. 15 is a graphical representation of an embodiment of a PEPST energy modulation agent-PA system with detachable bond.

Some photoactive drugs require that the PA molecule to enter the nucleus. FIG. 15 shows an embodiment of a PEPST probe where the PA drug molecule is bound to the metal nanoparticles via a linker (FIG. 15A) that can be cut by photon radiation (FIG. 15B). Such a probe is useful for therapy modalities where the PA molecules have to enter the nucleus, e.g., psoralen molecules need to enter the nucleus of cells and intercalate onto DNA (FIG. 15C). Since it is more difficult for metal nanoparticles to enter the cell nucleus than for smaller molecules, it is preferable to use PEPST probes that have releasable PA molecules.

Suitable linkers for linking the PA drug molecule to the metal nanoparticles include, but are not limited to, labile chemical bonds that can be broken by remote energy excitation (from outside the body, e.g., MW, IR, photoacoustic energy, ultrasound energy, etc.), labile chemical bonds that can be broken by the chemical environment inside cells, antibody-antigen, nucleic acid linkers, biotin-streptavidin, etc.

Nanoparticle Chain for Dual Plasmonics Effect

Figure 16:
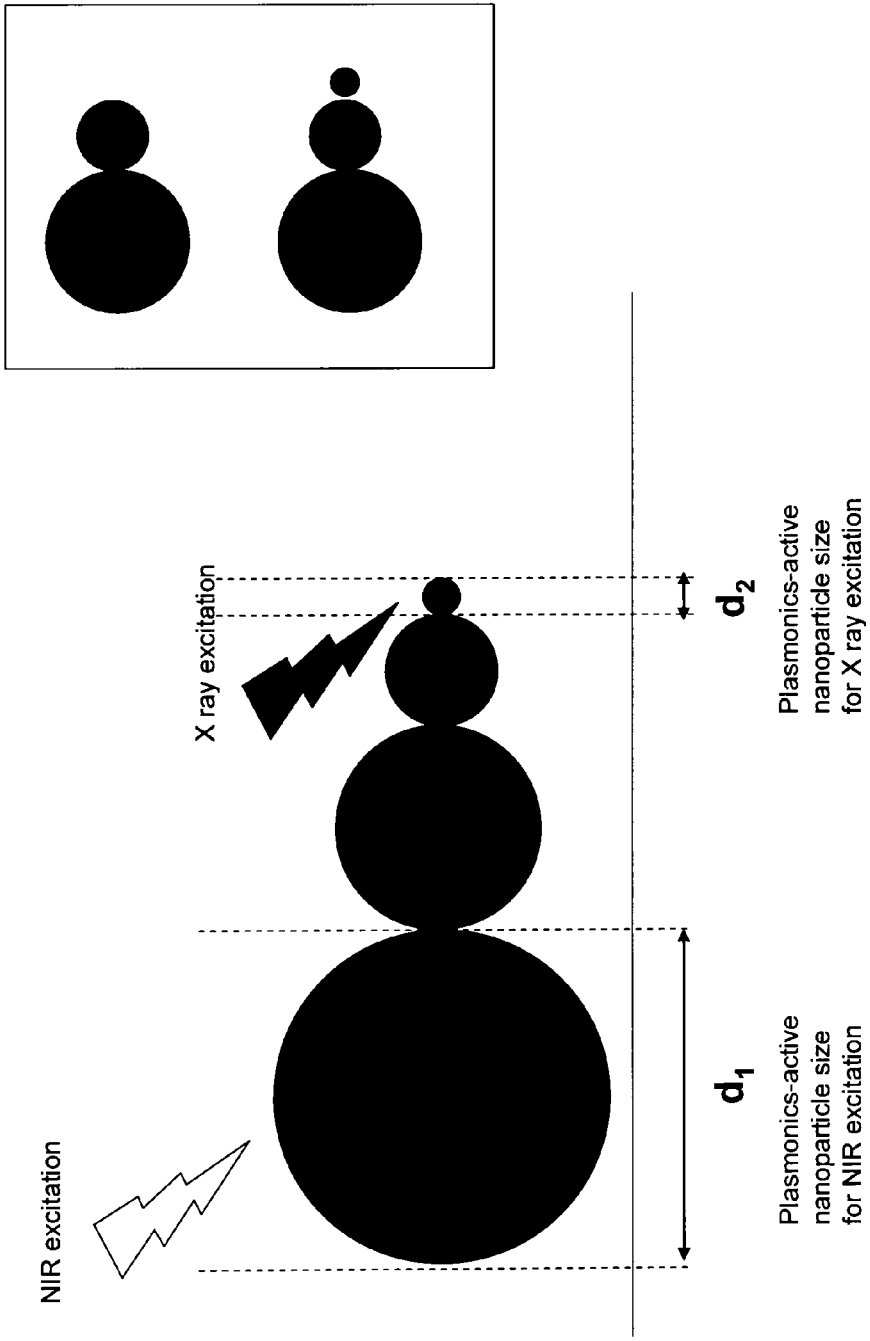
FIG. 16 is a graphical representation of an embodiment of PEPST probes for dual plasmonic excitation.
Figure 17:
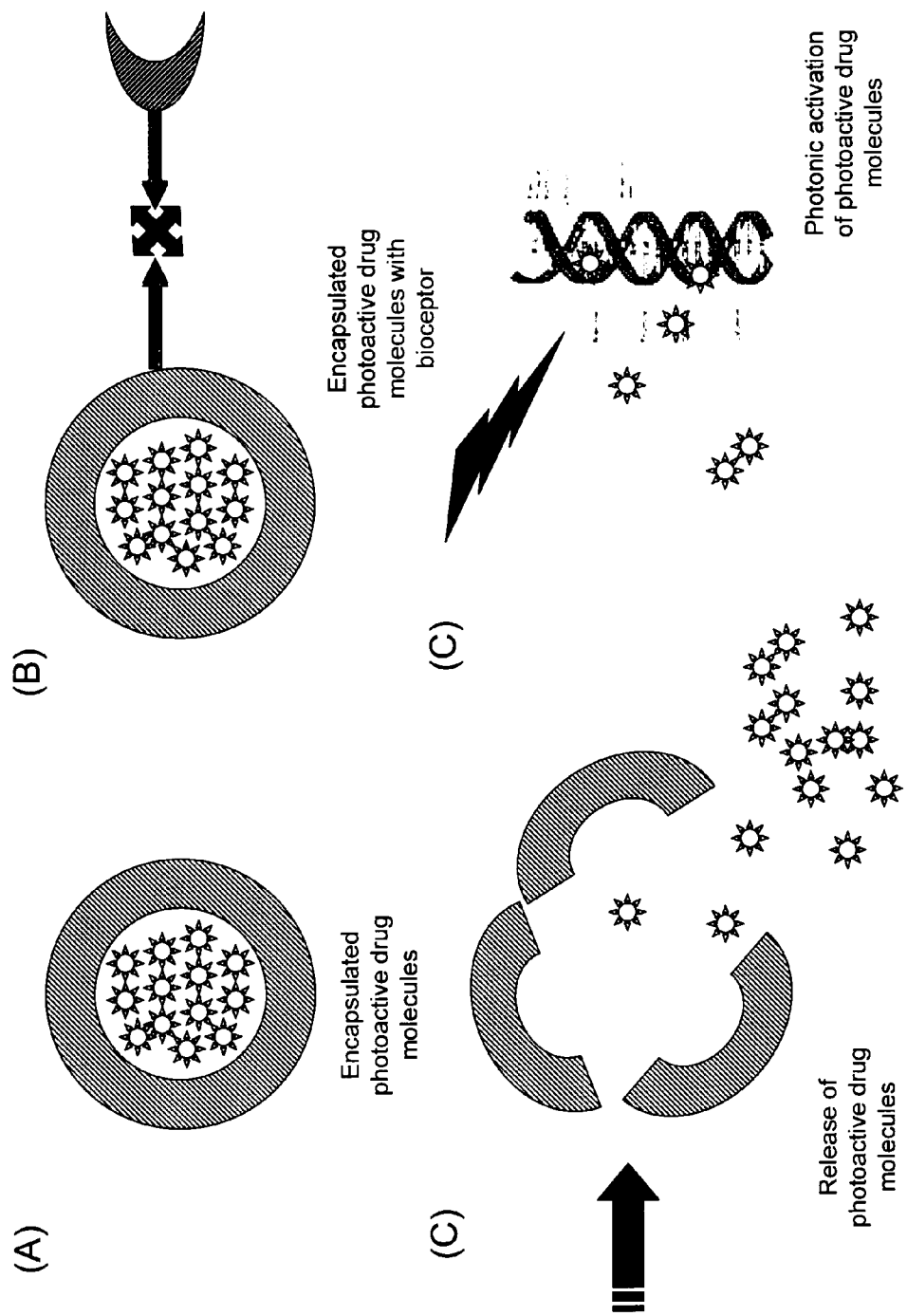
FIG. 17 is a graphical representation of an embodiment of a use of encapsulated photoactive agents.
Figure 18:
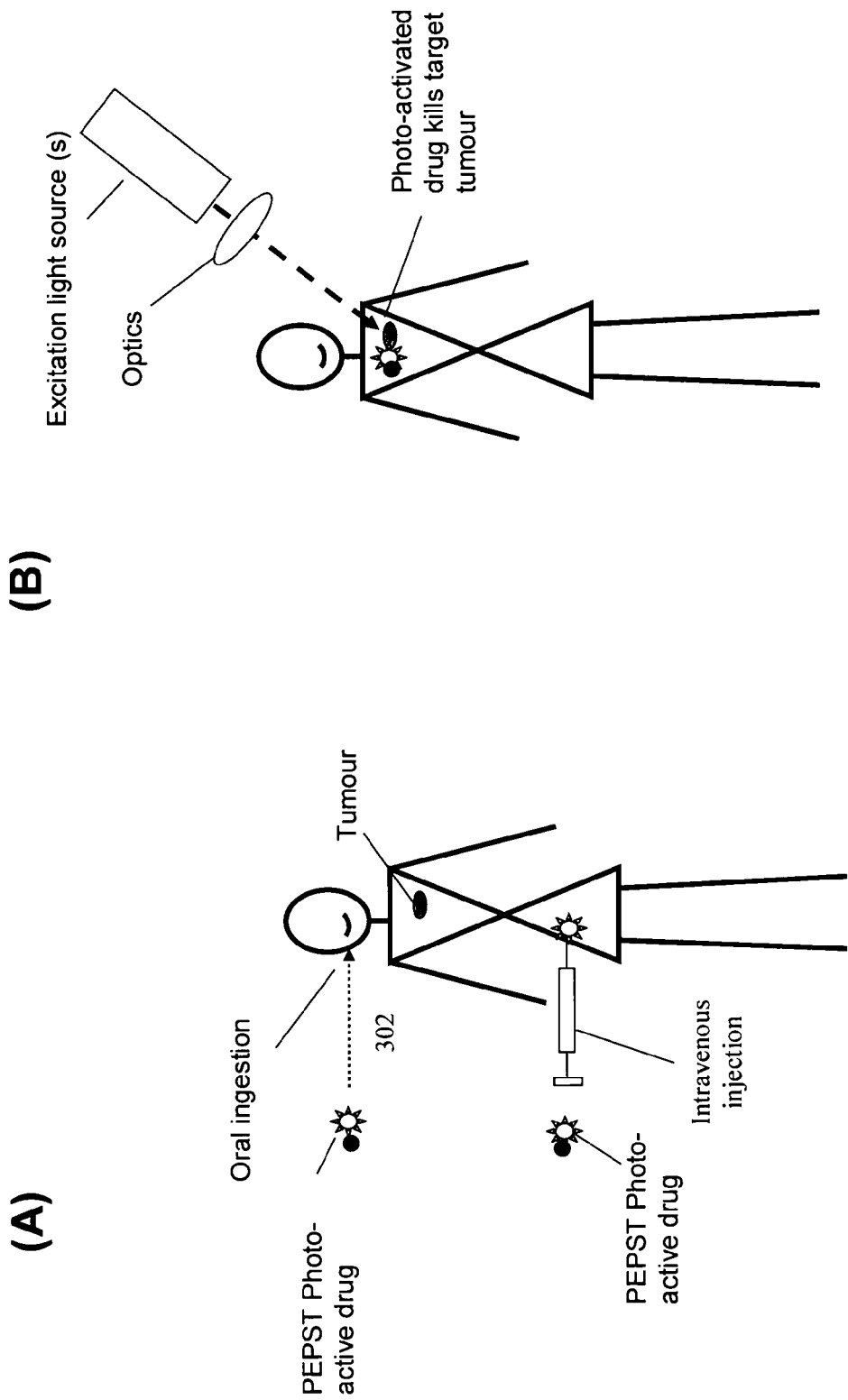
FIG. 18 is a simplified graphical representation of the use of the present invention principle of non-invasive PEPST modality.

As discussed previously, there is the need to develop nanoparticle systems that can have dual (or multi) plasmonics resonance modes. FIG. 16 illustrates an embodiment of the present invention PEPST probe having a chain of metal particles having different sizes and coupled to each other, which could exhibit such dual plasmonics-based enhancement. For example the parameters (size, metal type, structure, etc) of the larger nanoparticle (FIG. 16, left) can be tuned to NIR, VIS or UV light while the smaller particle (FIG. 16, right) can be tuned to X ray. There is also a coupling effect between these particles.

These nanoparticle chains are useful in providing plasmonics enhancement of both the incident radiation used (for example, x-ray activation of CdS) as well as plasmonics enhancement of the emitted radiation that will then activate the PA. Similar nanoparticles systems have been used as nanolens [*Self-Similar Chain of Metal Nanospheres as an Efficient Nanolens*, Kuiru Li, Mark I. Stockman, and David J. Bergman, *Physical Review Letter*, VOLUME 91, NUMBER 22, 227402-1, 2003].

Drug Delivery Platforms

Liposome Delivery of Energy Modulation Agent-PA Systems

The field of particle-based drug delivery is currently focused on two chemically distinct colloidal particles, liposomes and biodegradable polymers. Both delivery systems encapsulate the active drug. The drug is released from the particle as it lyses, in the case of liposomes, or disintegrates, as described for biodegradable polymers. One embodiment of the present invention uses liposomal delivery of energy modulation agent-PA systems (e.g., gold nanoshells) for therapy. An exemplary embodiment is described below, but is not intended to be limiting to the specific lipids, nanoparticles or other components recited, but is merely for exemplary purposes:

Preparation of Liposomes. the Liposome Preparation Method is Adapted from Hölig et. al Hölig, P., Bach, M., Völkel, T., Nahde, T., Hoffmann, S., Müller, R., and Kontermann, R. E., *Novel RGD lipopeptides for the targeting of liposomes to integrin-expressing endothelial and melanoma cells*. Protein Engineering Design and Selection, 2004. 17(5): p. 433-441]. Briefly, the lipids PEG-DPPE, PC, and Rh-DPPE are mixed in chloroform in a round bottom flask and evaporated (Hieroglyph Rotary Evaporator, Rose Scientific Ltd., Edmonton, Alberta, Canada) to eliminate chloroform. The dry film is dehydrated into aqueous phase with using PBS solution. A dry lipid film is prepared by rotary evaporation from a mixture of PC, cholesterol, and PEG-DPPE and then hydrated into aqueous phase using PBS. The mixture is vigorously mixed by overtaxing and bath solicited (Instrument, Company) and the suspension extruded through polycarbonate filter using Liposofast apparatus (Avestin Inc., Ottawa, ON, Canada) (pore-size 0.8 µm). Preparation of liposomes is performed as follows; 0.1 mmol of PC is dispersed in 8 ml of chloroform and supplemented with 0.5 mol of PEG-DPPE in 20 ml of chloroform. 0.3 mmol rhodamine-labeled phosphatidylethanolamine (Rh-DPPE) is then incorporated into the liposomes. The organic solvents are then removed by rotary evaporation at 35° C. for 2 h leaving a dry lipid film. Gold nanoshells are encapsulated into liposomes by adding them to the PBS hydration buffer and successively into the dry lipid film. This mixture is emulsified in a temperature controlled sonicator for 30 minutes at 35° C. followed by vortexing for 5 min. Encapsulated gold nanoshells are separated from unencapsulated gold nanoshells by gentle centrifugation for 5 minutes at 2400 r.p.m (1200 g). The resulting multilamellar vesicles suspension is extruded through polycarbonate filter using Liposofast apparatus (Avestin Inc., Ottawa, ON, Canada) (pore-size 0.8 µm). The aqueous mixture is obtained and stored at 4° C.

Fabrication of Gold Nanoparticles: The Frens method [Frens, G., *Controlled nucleation for the regulation of the particle size in monodisperse gold solutions*. Nature (London) Phys Sci, 1973. 241: p. 20-22] can be used in the present invention to synthesize a solution of gold nanoparticles ranging in diameter from 8-10 nm. Briefly, $5.0 \times 10^{-6}$ mol of $HAuCl_4$ is dissolved in 19 ml of deionized water producing a faint yellowish solution. This solution is heated with vigorous stirring in a rotary evaporator for 45 minutes. 1 ml of 0.5% sodium citrate solution is added and the solution is stirred for an additional 30 minutes. The color of the solution gradually changed from the initial faint yellowish to clear, grey, purple and finally a tantalizing wine-red color similar to merlot. The sodium citrate used serves in a dual capacity, first acting as a reducing agent, and second, producing negative citrate ions that are adsorbed onto the gold nanoparticles introducing surface charge that repels the particles and preventing nanocluster formation.

Preparation and Internalization of Liposome-encapsulated Gold Nanoshells: Liposome-encapsulated gold nanoshells are incubated with MCF-7 cells grown on partitioned coverslips for intracellular delivery. This is done by adding 10 µl of liposome-encapsulated gold nanoshells per 1 ml of cell culture medium. This is incubated for 30 minutes in a humidified (86% RH) incubator at 37° C. and 5% $CO_2$. This cell is used for localization studies; to track the rhodamine-DPPE-labeled liposomes into the cytoplasm of the MCF-7 cell. After incubation, the cells grown on cover-slips are washed three times in cold PBS and fixed using 3.7% formaldehyde in PBS. Rhodamine staining by rhodamine-DPPE-labeled liposomes is analyzed using a Nikon Diaphot 300 inverted microscope (Nikon, Inc., Melville, N.Y.).

Non-Invasive Cleavage of the Drug System In Vivo

After delivery of the drug system into the cell, there is sometimes the need to have the PA system (e.g. psoralen) in the nucleus in order to interact with DNA. If the PA is still linked to the energy modulation agent, both of them have to be transported into the nucleus. In the case with gold nanoparticles as the energy modulation agent system, there are several methods to incubate cells in vitro. For in vivo applications, one can link the PA to the gold nanoparticles using a chemical linkage that can be released (or cut) using non-invasive methods such as infrared, microwave, or ultrasound waves. An example of linkage is through a chemical bond or through a bioreceptor, such as an antibody. In this case, the PA is the antigen molecule bound to the energy modulation agent system that has an antibody targeted to the PA.

When the energy modulation agent-Ab-PA enters the cell, the PA molecules can be released from the energy modulation agent Ab system. To release the PA molecule from the antibody, chemical reagents can be used to cleave the binding between antibody and antigen, thus regenerating the biosensor [Vo-Dinh et al, 1988]. This chemical procedure is simple but is not practical inside a cell due to possible denaturation of the cell by the chemical. In previous studies, it has been demonstrated that the gentle but effective MHz-range ultrasound has the capability to release antigen molecules from the antibody-energy modulation agent system [Moreno-Bondi, M., Mobley, J., and Vo-Dinh, T., "Regenerable Antibody-based Biosensor for Breast Cancer," J. Biomedical Optics, 5, 350-354 (2000)]. Thus, an alternative embodiment is to use gentle ultrasonic radiation (non-invasively) to remove the PA (antigen) from the antibody at the energy modulation agent system.

In a preferred embodiment, the PA molecule is bound to the energy modulation agent by a chemically labile bond [Jon A. Wolff, and David B. Rozema, Breaking the Bonds: Non-viral Vectors Become Chemically Dynamic, Molecular Therapy (2007) 16(1), 8-15]. A promising method of improving the efficacy of this approach is to create synthetic vehicles (SVs) that are chemically dynamic, so that delivery is enabled by the cleavage of chemical bonds upon exposure to various physiological environments or external stimuli. An example of this approach is the use of masked endosomolytic agents (MEAs) that improve the release of nucleic acids from endosomes, a key step during transport. When the MEA enters the acidic environment of the endosome, a pH-labile bond is broken, releasing the agent's endosomolytic capability.

Use of Ferritin and Apoferritin as Targeted Drug Delivery

Another embodiment to deliver the energy modulation agent-PA drugs involves the use of ferritin and apoferritin compounds. There is increasing interest in ligand-receptor-mediated delivery systems due to their non-immunogenic and site-specific targeting potential to the ligand-specific biosites. Platinum anticancer drug have been encapsulated in apoferritin [Zhen Yang, Xiaoyong Wang, Huajia Diao, Junfeng Zhang, Hongyan Li, Hongzhe Sun and Zijian Guo, Encapsulation of platinum anticancer drugs by apoferritin, *Chem. Commun.* 33, 2007, 3453-3455]. Ferritin, the principal iron storage molecule in a wide variety of organisms, can also be used as a vehicle for targeted drug delivery. It contains a hollow protein shell, apoferritin, which can contain up to its own weight of hydrous ferric oxide-phosphate as a microcrystalline micelle. The 24 subunits of ferritin assemble automatically to form a hollow protein cage with internal and external diameters of 8 and 12 nm, respectively. Eight hydrophilic channels of about 0.4 nm, formed at the intersections of subunits, penetrate the protein shell and lead to the protein cavity. A variety of species such as gadolinium ($Gd^{3+}$) contrast agents, desferrioxamine B, metal ions, and nanoparticles of iron salts can be accommodated in the cage of apoferritin. Various metals such as iron, nickel, chromium and other materials have been incorporated into apoferritin [Iron incorporation into apoferritin. The role of apoferritin as a ferroxidase, The Journal of Biological Chemistry [002]-9258] Bakker yr:1986 vol:261 iss:28 pg:13182-5; Mitsuhiro Okuda[1], Kenji Iwahori[2], Ichiro Yamashita[2], Hideyuki Yoshimura[1]*, Fabrication of nickel and chromium nanoparticles using the protein cage of apoferritin, Biotechnology Bioengineering, Volume 84, Issue 2, Pages 187-194]. Zinc selenide nanoparticles (ZnSe NPs) were synthesized in the cavity of the cage-shaped protein apoferritin by designing a slow chemical reaction system, which employs tetraaminezinc ion and selenourea. The chemical synthesis of ZnSe NPs was realized in a spatially selective manner from an aqueous solution, and ZnSe cores were formed in almost all apoferritin cavities with little bulk precipitation [Kenji Iwahori, Keiko Yoshizawa, Masahiro Muraoka, and Ichiro Yamashita, Fabrication of ZnSe Nanoparticles in the Apoferritin Cavity by Designing a Slow Chemical Reaction System, Inorg. Chem., 44 (18), 6393-6400, 2005].

A simple method for synthesizing gold nanoparticles stabilized by horse spleen apoferritin (HSAF) is reported using $NaBH_4$ or 3-(N-morpholino)propanesulfonic acid (MOPS) as the reducing agent [Lei Zhang, Joe Swift, Christopher A. Butts, Vijay Yerubandi and Ivan J. Dmochowski, Structure and activity of apoferritin-stabilized gold nanoparticles, Journal of Inorganic Biochemistry, Vol. 101, 1719-1729, 2007]. Gold sulfite ($Au_2S$) nanoparticles were prepared in the cavity of the cage-shaped protein, apoferritin. Apoferritin has a cavity, 7 nm in diameter, and the diameter of fabricated $Au_2S$ nanoparticles is about the same size with the cavity and size dispersion was small. [Keiko Yoshizawa, Kenji Iwahori, Kenji Sugimoto and Ichiro Yamashita, Fabrication of Gold Sulfide Nanoparticles Using the Protein Cage of Apoferritin, Chemistry Letters, Vol. 35 (2006), No. 10 p. 1192]. Thus, in a preferred embodiment, the PA or energy modulation agent-PA compounds are encapsulated inside the apoferrtin shells.

Use of Ferritin and Apoferritin as Enhanced Targeting Agents

It was reported that ferritin could be internalized by some tumor tissues, and the internalization was associated with the membrane-specific receptors [S. Fargion, P. Arosio, A. L. Fracanzoni, V. Cislaghi, S. Levi, A. Cozzi, A Piperno and A. G. Firelli, Blood, 1988, 71, 753-757; P.C. Adams, L. W. Powell and J. W. Halliday, *Hepatology,* 1988, 8, 719-721]. Previous studies have shown that ferritin-binding sites and the endocytosis of ferritin have been identified in neoplastic cells [M. S. Bretscher and J. N. Thomson, *EMBO J,* 1983, 2, 599-603]. Ferritin receptors have the potential for use in the delivery of anticancer drugs into the brain [S. W. Hulet, S. Powers and J. R. Connor, *J. Neurol. Sci.,* 1999, 165, 48-55]. In one embodiment, the present invention uses ferritin or apoferritin to both encapsulate PA and energy modulation agent-PA systems and also target tumor cells selectively for enhanced drug delivery and subsequent phototherapy. In this case no additional bioreactors are needed.

FIG. 17 schematically illustrates the use of encapsulated photoactive agents (FIG. 17A) for delivery into tissue and subsequent release of the photoactive drugs after the encapsulated systems enter the cell. Note the encapsulated system can have a bioreceptor for selective tumor targeting (FIG. 17B). Once inside the cell, the capsule shell (e.g., liposomes, apoferritin, etc.) can be broken (FIG. 17C) using non-invasive excitation (e.g., ultrasound, RF, microwave, IR, etc) in order to release the photoactive molecules that can get into the nucleus and bind to DNA (FIG. 17D).

Non-Invasive Phototherapy Using PEPST Modality

FIG. 18 illustrates the basic operating principle of the PEPST modality. The PEPST photoactive drug molecules are given to a patient by oral ingestion, skin application, or by intravenous injection. The PEPST drugs travel through the blood stream inside the body towards the targeted tumor (either via passive or active targeting strategies). If the disease is systematic in nature a photon radiation at suitable wavelengths is used to irradiate the skin of the patient, the light being selected to penetrate deep inside tissue (e.g., NIR or X ray). For solid tumors, the radiation light source is directed at the tumor. Subsequently a treatment procedure can be initiated using delivery of energy into the tumor site. One or several light sources may be used as described in the previous sections. One embodiment of therapy comprises sending NIR radiation using an NIR laser through focusing optics. Focused beams of other radiation types, including but not limited to X ray, microwave, radio waves, etc. can also be used and will depend upon the treatment modalities used.

Exciton-Plasmon Enhanced Phototherapy (EPEP)

Basic Principle of Exciton-Induced Phototherapy

Excitons in Solid Materials

Excitons are often defined as "quasiparticles" inside a solid material. In solid materials, such as semiconductors, molecular crystals and conjugated organic materials, light excitation at suitable wavelength (such as X ray, UV and visible radiation, etc) can excite electrons from the valence band to the conduction band. Through the Coulomb interaction, this newly formed conduction electron is attracted, to the positively charged hole it left behind in the valence band. As a result, the electron and hole together form a bound state called an exciton. (Note that this neutral bound complex is a "quasiparticle" that can behave as a boson—a particle with integer spin which obeys Bose-Einstein statistics; when the temperature of a boson gas drops below a certain value, a large number of bosons 'condense' into a single quantum state— this is a Bose-Einstein condensate (BEC). Exciton production is involved in X-ray excitation of a solid material. Wide band-gap materials are often employed for transformation of the x-ray to ultraviolet/visible photons in the fabrication of scintillators and phosphors [Martin Nikl, *Scintillation detectors for x-rays, Meas. Sci. Technol.* 17 (2006) R37-R54]. The theory of excitons is well known in materials research and in the fabrication and applications of semiconductors and other materials. However, to the present inventors' knowledge, the use of excitons and the design of energy modulation agent materials based on exciton tunability for phototherapy have not been reported.

During the initial conversion a multi-step interaction of a high-energy X-ray photon with the lattice of the scintillator material occurs through the photoelectric effect and Compton scattering effect; for X-ray excitation below 100 keV photon energy the photoelectric effect is the main process. Many excitons (i.e., electron-hole pairs) are produced and thermally distributed in the conduction bands (electrons) and valence bands (holes). This first process occurs within less than 1 ps. In the subsequent transport process, the excitons migrate through the material where repeated trapping at defects may occur, leading to energy losses due to nonradiative recombination, etc. The final stage, luminescence, consists in consecutive trapping of the electron-hole pairs at the luminescent centers and their radiative recombination. The electron-hole pairs can be trapped at the defects and recombine, producing luminescent. Luminescent dopants can also be used as traps for exciton.

Exciton Traps

Figure 20:
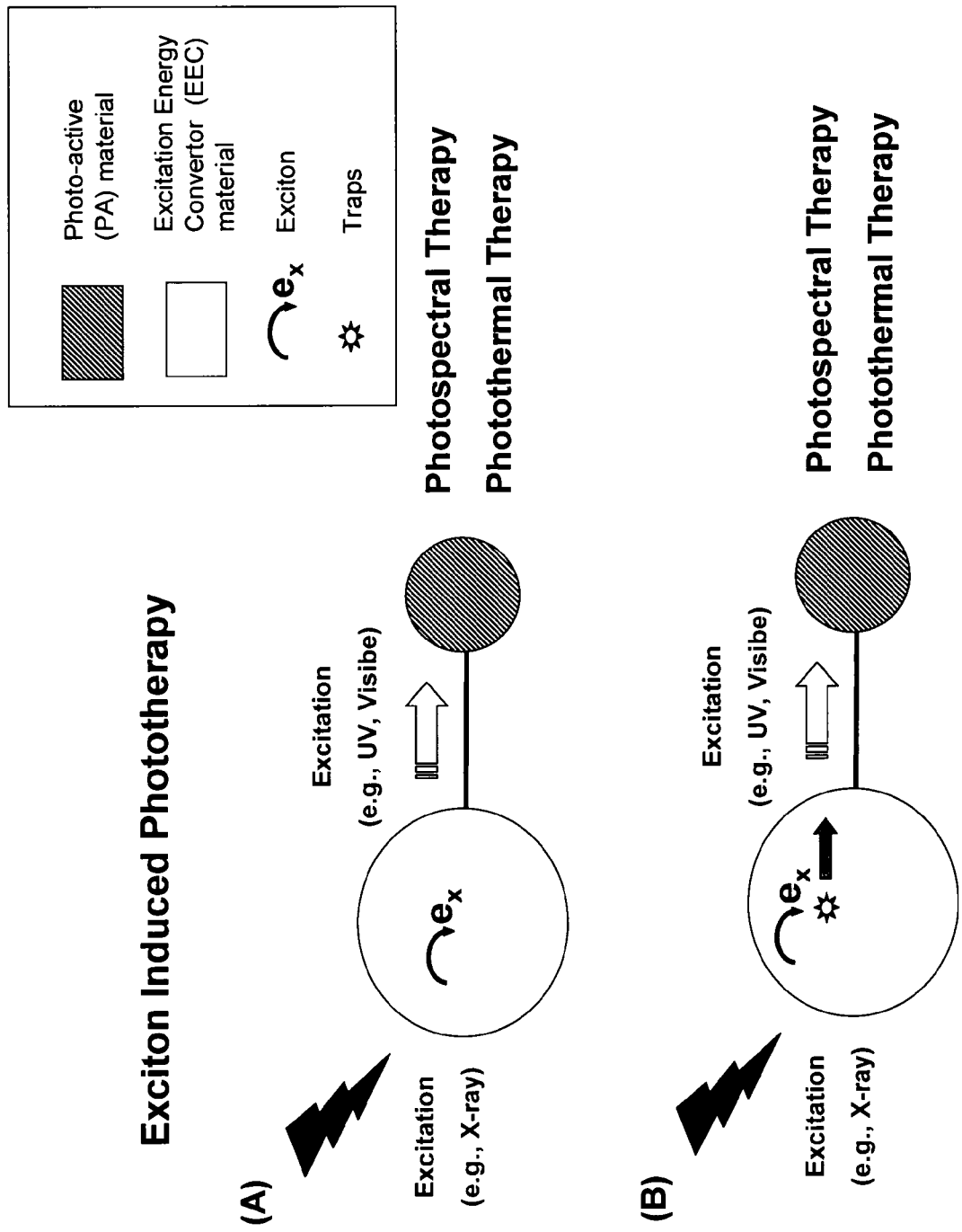
FIG. 20 shows various schematic embodiments of basic EIP probes.
Figure 21A:
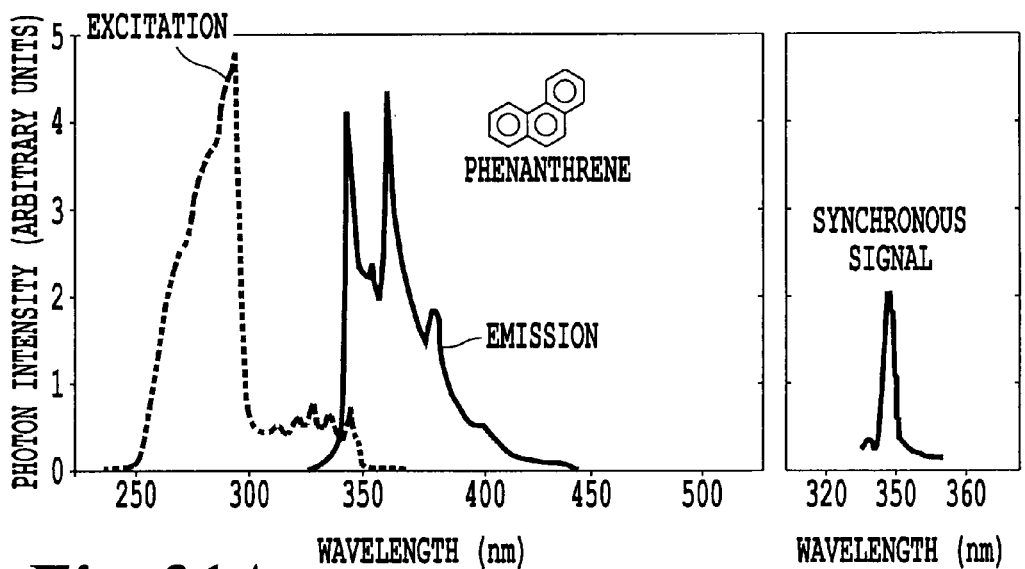
FIGS. 21A-21E are graphical representations of fluorescence spectra of PAH compounds.
Figure 21B:
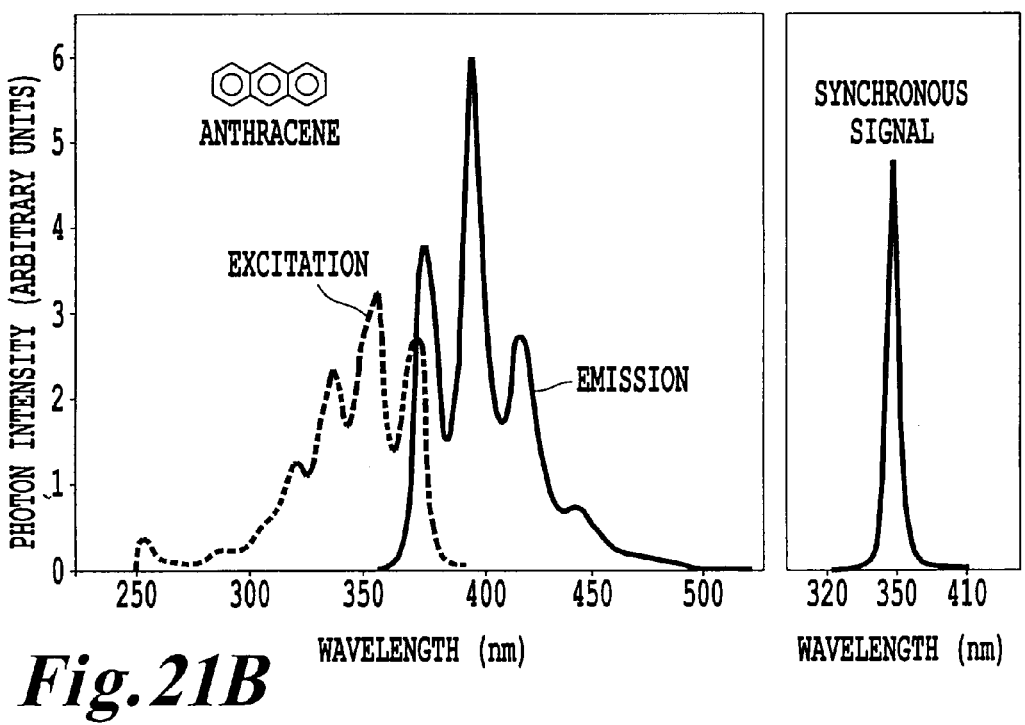
Figure 21C:
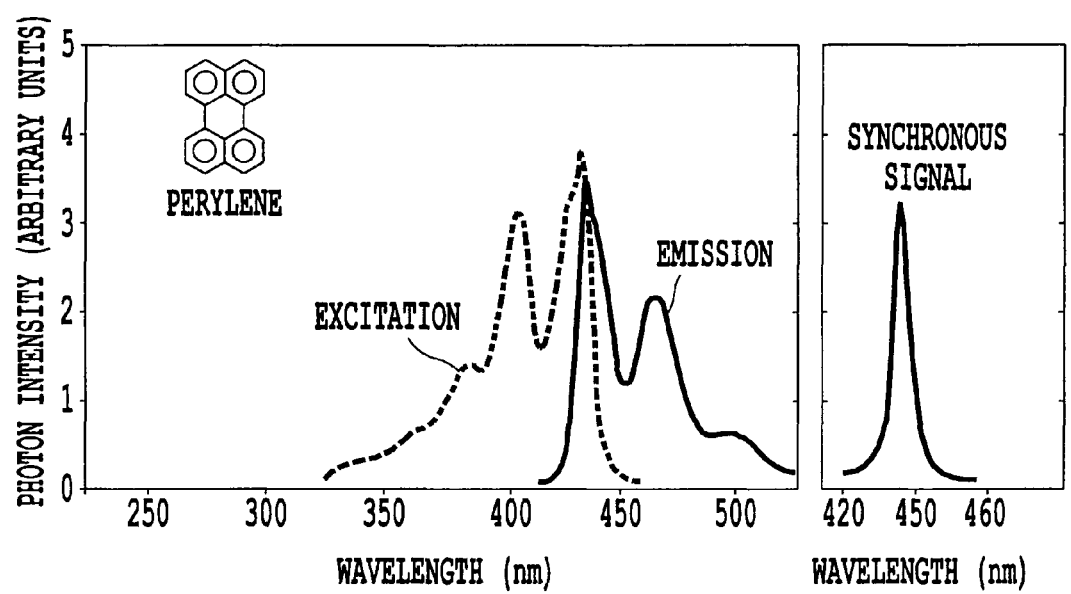
Figure 21D:
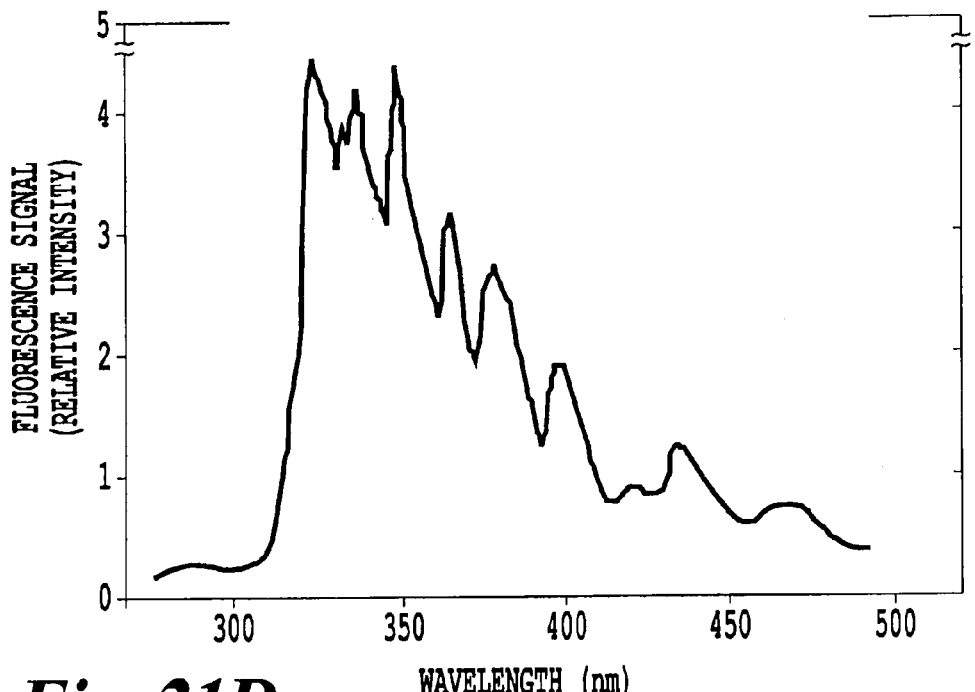
Figure 21E:
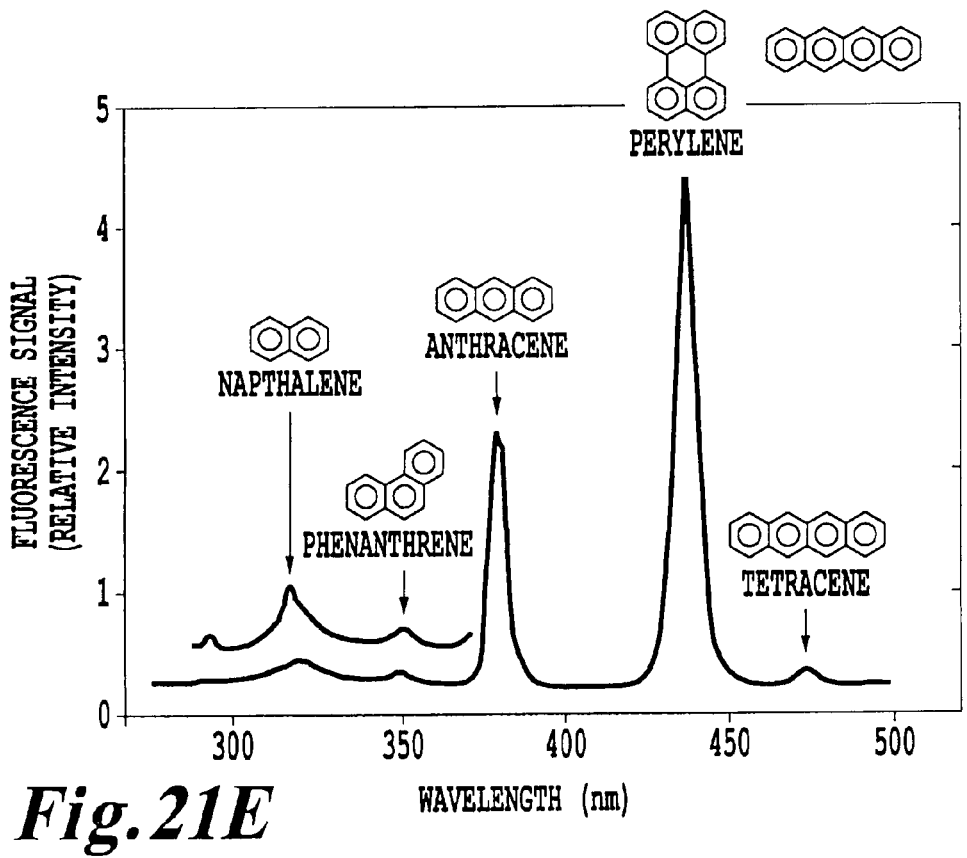

Exciton traps can be produced using impurities in the crystal host matrix. In impure crystals with dipolar guest molecules the electron trap states may arise when electron is localized on a neighbor of the impurity molecule. Such traps have been observed in anthracene doped with carbazole [Kadshchuk, A. K, Ostapenko, N. I., Skryshevskii, Yu. A., Sugakov, V. I. and Susokolova, T. O., *Mol. Cryst. and Liq. Cryst.*, 201, 167 (1991)]. The formation of these traps is due to the interaction of the dipole moment of the impurity with charge carrier. When the concentration of the dopant (or impurities) is increased, spectra exhibit additional structure of spectrum due to the trapping of carriers on clusters of impurity molecules. Sometimes, impurities and dopants are not required: the electron or exciton can also be trapped on a structural defect in such crystals due to the electrostatic interaction with reoriented dipole moment of disturbed crystal molecules [S. V. Izvekov, V. I. Sugakov, *Exciton and Electron Traps on Structural Defects in Molecular Crystals with Dipolar Molecules, Physica Scripta. Vol. T66*, 255-257, 1996]. One can design structural defects in molecular crystals that serve as exiton traps. The development of GaAs/AlGaAs nanostructures and use of nanofabrication technologies can design engineered exciton traps with novel quantum mechanical properties in materials Design, Fabrication and Operation of EIP Probes FIG. 20 shows various embodiments of EIP probes that can be designed:

(A) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have structural defects that serve as traps for excitons.

(B) probe comprising PA molecules bound (through a linker, which can be fixed or detachable) to an energy modulation agent particle that can produce excitons under radiative excitation at a suitable wavelength (e.g., X-ray). In this preferred embodiment, the energy modulation agent materials have impurities or dopant molecules that serve as traps for excitons.

EIP Probes with Tunable Emission:

The embodiment in probes B provide the capability to tune the energy conversion from an X ray excitation source into a wavelength of interest to excite the PA molecules. In 1976, D'Silva et al demonstrated that polynuclear aromatic hydrocarbons (PAH) molecules doped in a frozen n-alkane solids could be excited by X-ray and produce luminescence at visible wavelengths characteristics of their luminescence spectra. [A. P. D'Silva, G. J. Oestreich, and V. A. Fassel, X-ray excited optical luminescence of polynuclear aromatic hydrocarbons, Anal. Chem.; 1976; 48(6) pp 915-917]. Tunable EIP probes can be designed to contain such luminescent dopants such as highly luminescent PAHs exhibiting luminescence emission in the range of 300-400 nm suitable to activate psoralen. A preferred embodiment of the EIP with tunable emission comprises a solid matrix (semiconductors, glass, quartz, conjugated polymers, etc) doped with naphthalene, phenanthrene, pyrene or other compounds exhibiting luminescence (fluorescence) in the 300-400nm range [*T. Vo-Dinh, Multicomponent analysis by synchronous luminescence spectrometry, Anal. Chem.*; 1978; 50(3) pp 396-401]. See FIGS. 21A-21E. The EEC matrix could be a semiconductor material, preferably transparent at optical wavelength of interest (excitation and emission).

Figure 22:
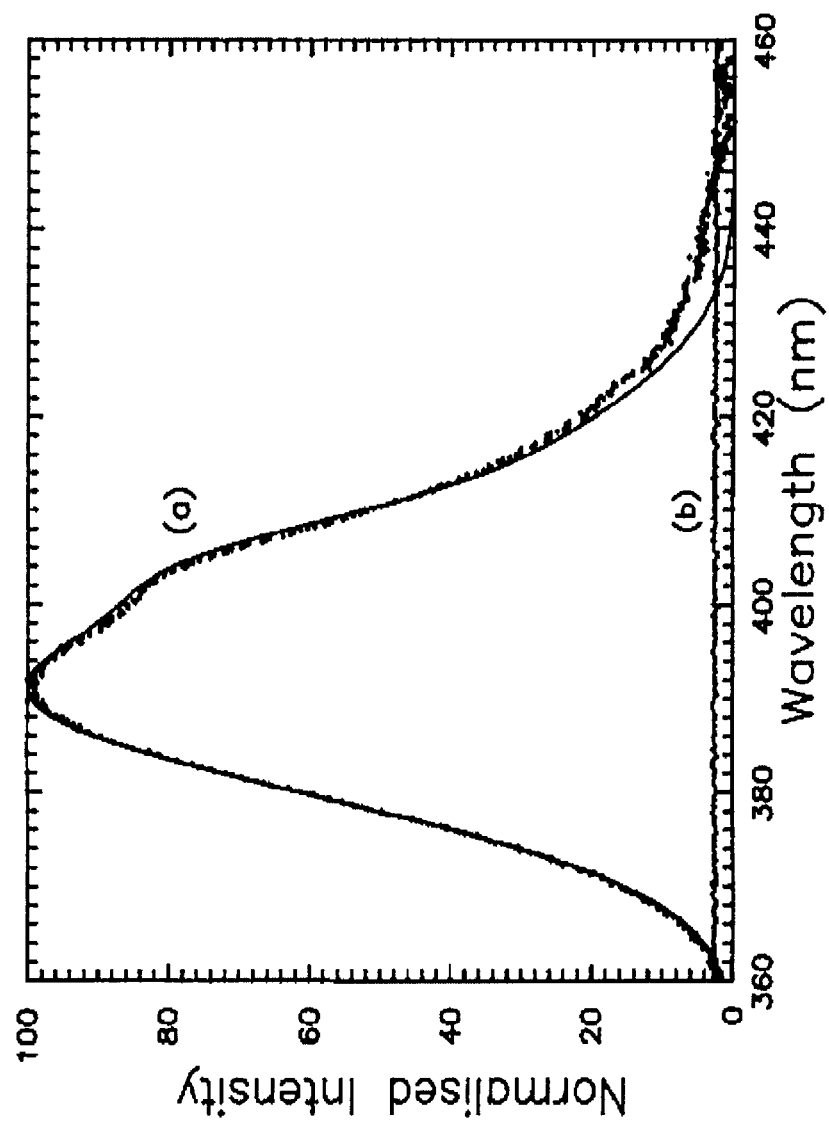
FIG. 22 is a graph showing the XEOL of Eu doped in BaFBr matrix.

Other dopant species such as rare earth materials can also be used as dopants. FIG. 22 shows the X ray excitation optical luminescence (XEOL) of Europium doped in a matrix of BaFBr, emitting at 370-420 nm. U.S. Patent Application Publication No. 2007/0063154 (hereby incorporated by reference) describes these and other nanocomposite materials (and methods of making them) suitable for XEOL.

Figure 23:
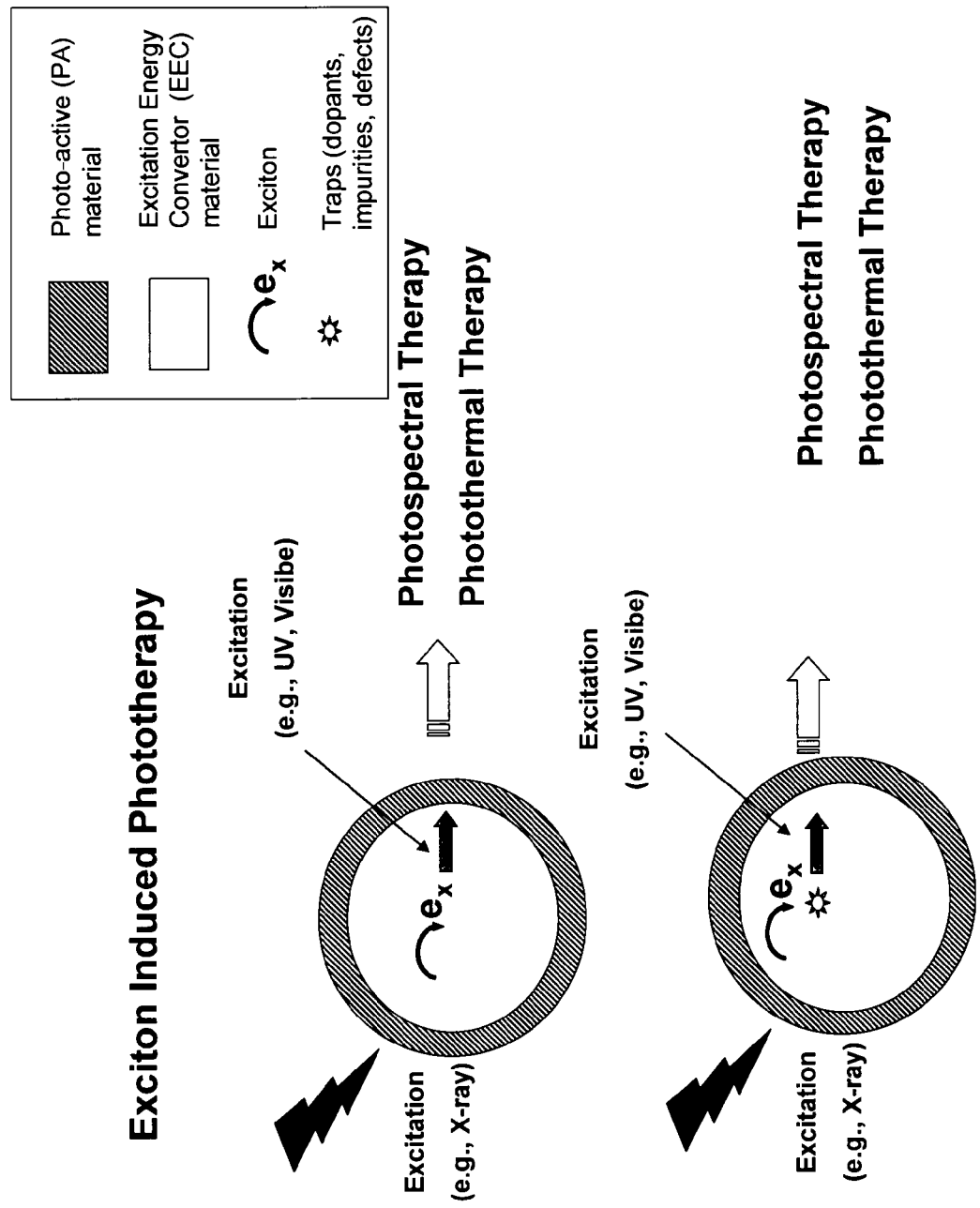
FIG. 23 provides further embodiments of schematic designs of EIP probes.

FIG. 23 shows various embodiments of EIP probes that can be designed:

(A) probe comprising PA molecules bound around the energy modulation agent particle or embedded in a shell around an energy modulation agent particle that can produce excitons under radiative excitation at a suitable wavelength (e.g., X-ray). In this preferred embodiment, the energy modulation agent materials has structural defects that serve as traps for excitons.

(B) probe comprising PA molecules bound around the energy modulation agent particle or embedded in a shell around an energy modulation agent particle that can produce excitons under radiative excitation at a suitable wavelength (e.g., X-ray). In this preferred embodiment, the energy modulation agent materials have impurities or dopant molecules that serve as traps for excitons.

Principle of Exciton-Plasmon Enhanced Phototherapy (EPEP)

There is recent interest in an advanced photophysical concept involving quantum optical coupling between electronic states (excitons), photons and enhanced electromagnetic fields (plasmons). Such a concept involving coupling between excitons and plasmons can be used to enhance a phototherapy modality, referred to as *Exciton-Plasmon Enhanced Phototherapy* (*EPEP*).

A fundamental key concept in photophysics is the formation of new quasiparticles from admixtures of strongly-coupled states. Such mixed states can have unusual properties possessed by neither original particle. The coupling between excitons and plasmons can be either weak or strong. When the light-matter interaction cannot be considered as a perturbation, the system is in the strong coupling regime. Bellesa et al showed a strong coupling between a surface plasmon (SP) mode and organic excitons occurs; the organic semiconductor used is a concentrated cyanine dye in a polymer matrix deposited on a silver film [Ref: J. Bellessa, * C. Bonnand, and J. C. Plenet, J Mugnier, *Strong Coupling between Surface Plasmons and Excitons in an Organic Semiconductor, Phys. Rev. Lett*, 93 (3), 036404-1, 2004]. Govorov et al describe the photophysical properties of excitons in hybrid complexes consisting of semiconductor and metal nanoparticles. The interaction between individual nanoparticles can produce an enhancement or suppression of emission. Enhanced emission comes from electric field amplified by the plasmon resonance, whereas emission suppression is a result of energy transfer from semiconductor to metal nanoparticles. [Alexander O. Govorov, *, † Garnett W. Bryant,;‡ Wei Zhang, † Timur Skeini, † Jaebeom Lee, § Nicholas A. Kotov, § Joseph M Slocik, |and Rajesh R. Naik|, *Exciton-Plasmon Interaction and Hybrid Excitons in Semiconductor-Metal Nanoparticle Assemblies, Nano Lett.*, Vol. 6, No. 5, 984, 2006]. Bondarev et al also described a theory for the interactions between excitonic states and surface electromagnetic modes in small-diameter (<1 nm) semiconducting single-walled carbon nanotubes (CNs). [I. V. Bondarev, K. Tatur and L. M. Woods, *Strong exciton-plasmon coupling in semiconducting carbon nanotubes*].

Fedutik et al reported about the synthesis and optical properties of a composite metal-insulator-semiconductor nanowire system which consists of a wet-chemically grown silver wire core surrounded by a $SiO_2$ shell of controlled thickness, followed by an outer shell of highly luminescent CdSe nanocrystals [Yuri Fedutik, † Vasily Temnov, † Ulrike Woggon, † Elena Ustinovich, ‡ and Mikhail Artemyev* ‡, *Exciton-Plasmon Interaction in a Composite Metal-Insulator-Semiconductor Nanowire System, J. Am. Chem. Soc.,* 129 (48), 14939-14945, 2007]. For a $SiO_2$ spacer thickness of ~15 nm, they observed an efficient excitation of surface plasmons by excitonic emission of CdSe nanocrystals. For small d, well below 10 nm, the emission is strongly suppressed (PL quenching), in agreement with the expected dominance of the dipole-dipole interaction with the damped mirror dipole [G. W. Ford and W. H. Weber, *Electromagnetic interactions of molecules with metal surfaces," Phys. Rep.* 113, 195-287 (1984)]. For nanowire lengths up to ~10 μm, the composite metal-insulator-semiconductor nanowires (($Ag)SiO_2$)CdSe act as a waveguide for ID-surface plasmons at optical frequencies with efficient photon out coupling at the nanowire tips, which is promising for efficient exciton-plasmon-photon conversion and surface plasmon guiding on a submicron scale in the visible spectral range.

Experiments on colloidal solutions of Ag nanoparticles covered with J-aggregates demonstrated the possibility of using the strong scattering cross section and the enhanced field associated with surface plasmon to generate stimulated emission from J-aggregate excitons with very low excitation powers. [Gregory A. Wurtz, * Paul R. Evans, William Hendren, Ronald Atkinson, Wayne Dickson, Robert J Pollard, and Anatoly V Zayats, *Molecular Plasmonics with Tunable Exciton-Plasmon Coupling Strength in J-Aggregate Hybridized Au Nanorod Assemblies, Nano Lett.*, Vol. 7, No. 5, 1297, 2007]. Their coupling to surface plasmons excitations therefore provides a particularly attractive approach for creating low-powered optical devices. This process can lead to efficient X-ray coupling for phototherapy. In addition, the coupling of J-aggregates with plasmonics structures presents genuine fundamental interest in the creation of mixed plasmon-exciton states.

Design, Fabrication and Operation of EPEP Probes

FIGS. 24-1 and 24-2 show various embodiments of EPEP probes of the present invention showing the exciton-plasmon coupling:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle covered with a nanoshell of silica (or other dielectric material). The silica layer (or nanoshell) (see FIG. 24A and FIG. 24B; layer nanoshell in white between energy modulation material and metal nanostructures) is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect also enhances the energy modulation agent emission light. These processes are due to strong coupling between excitons (in the energy modulation agent materials and plasmons in the metal nanoparticles; and (B) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticle via a spacer (linker). The spacer is designed to prevent quenching of the luminescence light emitted by the energy modulation agent particle excited by X-ray.

FIG. 25 shows yet further embodiments of EPEP probes of the present invention:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of separate nanostructures (nano islands, nanorods, nanocubes, etc. . . . ) of metal (preferably Au, Ag). The silica layer (or other dielectric material) is designed to prevent quenching of the luminescence light emitted by the EEC (also referred to as energy modulation agent) particle excited by X-ray. The metal nanostructures (Au, Ag, etc) are designed to induce plasmons that enhance the X ray excitation that subsequently leads to an increase in the EEC light emission, ultimately enhancing the efficiency of photoactivation, i.e. phototherapy. The structure of the nanoparticle can also be designed such that the plasmonics effect also enhance the energy modulation agent emission light. These processes are due to strong coupling between excitons (in the energy modulation agent materials and plasmons in the metal nanostructures).

(B) probe comprising a group of PA molecules in a particle bound (through a linker, which can be fixed or detachable) to an energy modulation agent particle that can produce excitons under radiative excitation at a suitable wavelength (e.g., X-ray). The PA-containing particle is covered with a layer of metallic nanostructures (preferably Au, Ag). The metal nanostructures (Au, Ag, etc) are designed to induce plasmons that enhance the energy modulation agent light emission, ultimately enhancing the efficiency of photoactivation, i.e. phototherapy.

(C) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is covered with a nanoshell of silica (or other dielectric material), which is covered by a layer of metallic nanostructures (Au, Ag). The silica layer (or other dielectric material) is designed to prevent quenching of the luminescence light emitted by the energy modulation agent particle excited by X-ray. The metal nanostructures (Au, Ag, etc) are designed to induce plasmons that enhance the X ray excitation that subsequently leads to an increase in the energy modulation agent light emission, ultimately enhancing the efficiency of photoactivation, i.e. phototherapy. In addition, the PA-containing particle is covered with a layer of metallic nanostructures (Au, Ag). The metal nanostructures (Au, Ag, etc) are designed to induce plasmons that enhance the EEC light emission, ultimately enhancing the efficiency of photoactivation, i.e. phototherapy.

Hybrid EPEP Nano-Superstructures

EPEP probes can also comprise hybrid self-assembled superstructures made of biological and abiotic nanoscale components, which can offer versatile molecular constructs with a spectrum of unique electronic, surface properties and photospectral properties for use in phototherapy.

Biopolymers and nanoparticles can be integrated in superstructures, which offer unique functionalities because the physical properties of inorganic nanomaterials and the chemical flexibility/specificity of polymers can be used. Noteworthy are complex systems combining two types of excitations common in nanomaterials, such as excitons and plasmons leading to coupled excitations. Molecular constructs comprising building blocks including metal, semiconductor nanoparticles (NPs), nanorods (NRs) or nanowires (NWs) can produce EPEP probes with an assortment of photonic properties and enhancement interactions that are fundamentally important for the field of phototherapy. Some examples of assemblies of some NW nanostructures and NPs have been reported in biosensing. Nanoscale superstructures made from CdTe nanowires (NWs) and metal nanoparticles (NPs) are prepared via bioconjugation reactions. Prototypical biomolecules, such as D-biotin and streptavidin pair, were utilized to connect NPs and NWs in solution. It was found that Au NPs form a dense shell around a CdTe NW. The superstructure demonstrated unusual optical effects related to the long-distance interaction of the semiconductor and noble metal nanocolloids. The NWNP complex showed 5-fold enhancement of luminescence intensity and a blue shift of the emission peak as compared to unconjugated NW. [Jaebeom Lee, † Alexander O. Govorov, ‡ John Dulka, ‡ and Nicholas A. Kotov*, †, *Bioconjugates of CdTe Nanowires and Au Nanoparticles: Plasmon-Exciton Interactions, Luminescence Enhancement, and Collective Effects*, Nano Lett., Vol. 4, No. 12, 2323, 2004].

To the present inventors' knowledge, these advanced concepts have not been applied to phototherapy and EPEP probes comprising superstructures from NPs, NRs and NWs are still a new unexplored territory of phototherapy.

FIG. 25 shows various embodiments of EPEP probes of the present invention comprising superstructures of NPs, NWs and NRs.:

(A) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanowire (or nanorod) covered with a nanoshell cylinder of silica (or other dielectric material). The silica nanoshells cylinder is designed to prevent quenching of the luminescence light emitted by the energy modulation agent particle excited by X-ray. The metal nanoparticle (Au, Ag, etc) is designed to induce plasmons that enhance the X ray excitation that subsequently leads to an increase in the energy modulation agent light emission, ultimately enhancing the efficiency of photoactivation, i.e. phototherapy. The structure of the nanoparticle can also be designed such that the plasmonics effect and/or the exciton-plasmon coupling (EPC) effect also enhances the energy modulation agent emission light. These processes are due to strong coupling between excitons (in the energy modulation agent materials and plasmons in the metal nanoparticles; and (B) probe comprising a PA molecule or group of PA molecules bound (through a linker, which can be fixed or detachable) to an energy modulation agent particle that can produce excitons under radiative excitation at a suitable wavelength (e.g., X-ray). The energy modulation agent particle is bound to (or in proximity of) a metal nanoparticles via a spacer (linker). The spacer is designed to prevent quenching of the luminescence light emitted by the energy modulation agent particle excited by X-ray. Same effect as above in (A)

Figure 26:
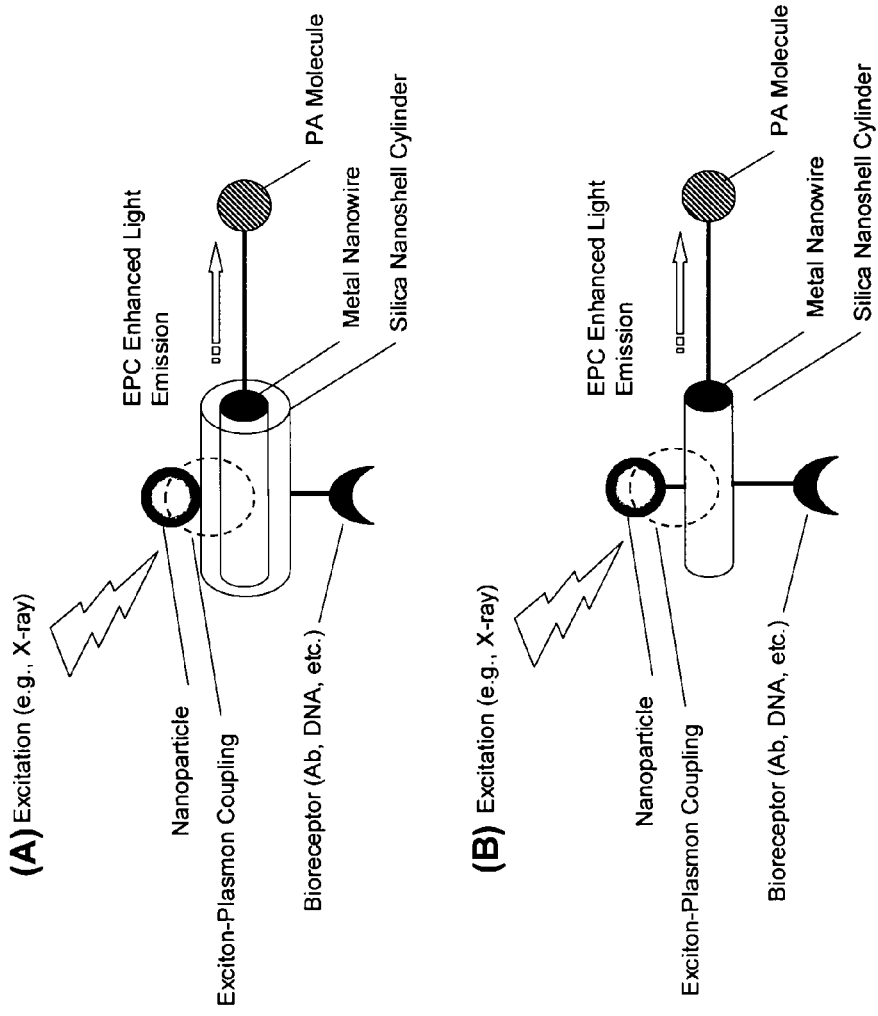
FIG. 26 is a graphical representation of various embodiments of EPEP probes having NPs, NWs, NRs and bioreceptors.

FIG. 26 shows another set of embodiments of EPEP probes of the present invention comprising superstructures of NPs, NWs and NRs and bioreceptors (antibodies, DNA, surface cell receptors, etc.). The use of bioreceptors to target tumor cells has been discussed previously above in relation to PEPST probes. Note that in this embodiment the PA molecules are attached along the NW axis in order to be excited by the emitting light form the NWs.

Figure 27:
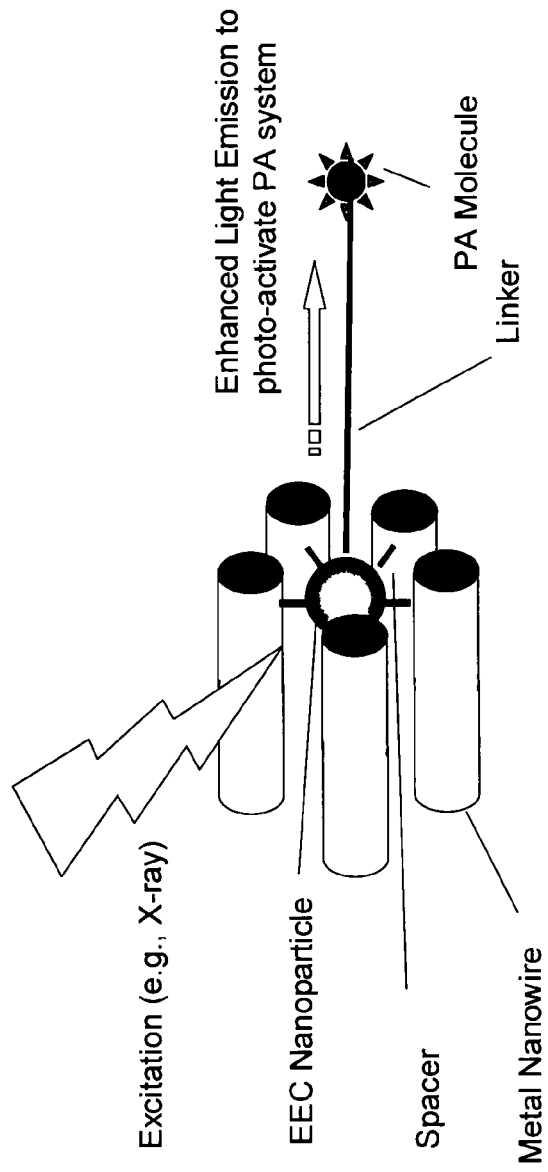
FIG. 27 is a graphical representation of an embodiment of EPEP probes having NPs and multiple NWs.

FIG. 27 shows another embodiment of EPEP probes of the present invention comprising superstructures of NPs linked to multiple NWs.

For some embodiments, by adding metal nanostructures designed to interact specifically with the excitons in the energy modulation agent system, there are significant improvements:

(1) an additional radiative pathway from exciton to photon conversion is introduced (2) the metal nanostructures can be designed to amplify (due to the plasmonics effect) the excitation radiation (e.g., X-ray) and/or the emission radiation (e.g, UV or visible) to excite the photo-active (PA) molecule, thereby enhancing the PA effectiveness.

Various metallic nanostructures that can be used in EPEP probe embodiments of the present invention are the same as those illustrated in FIG. 4 for the PEPST probes.

EPEP Probes with Microresonators

In a preferred embodiment the energy modulation agent system can be designed to serve also as a microresonator having micron or submicron size. Lipson et al described a resonant microcavity and, more particularly, to a resonant microcavity which produces a strong light-matter interaction [M. Lipson; L. C. Kimerling; Lionel C, Resonant microcavities, U.S. Pat. No. 6,627,923, 2000]. A resonant microcavity, typically, is formed in a substrate, such as silicon, and has dimensions that are on the order of microns or fractions of microns. The resonant microcavity contains optically-active matter (i.e., luminescent material) and reflectors which confine light in the optically-active matter. The confined light interacts with the optically-active matter to produce a light-matter interaction. The light-matter interaction in a microcavity can be characterized as strong or weak. Weak interactions do not alter energy levels in the matter, whereas strong interactions alter energy levels in the matter. In strong light-matter interaction arrangements, the confined light can be made to resonate with these energy level transitions to change properties of the microcavity.

Experimental Methods

Preparation of Nanoparticles (Ag, Au)

There many methods to prepare metal nanoparticles for EPEP or PEPST probes. Procedures for preparing gold and silver colloids include electroexplosion, electrodeposition, gas phase condensation, electrochemical methods, and solution-phase chemical methods. Although the methodologies for preparing homogeneous-sized spherical colloidal gold populations 2-40 nm in diameter are well known [N. R. Jana, L. Gearheart and C. J Murphy, *Seeding growth for size control of 5-40 nm diameter gold nanoparticles. Langmuir* 17 (2001), pp. 6782-6786], and particles of this size are commercially available. An effective chemical reduction method for preparing populations of silver particles (with homogeneous optical scattering properties) or gold particles (with improved control of size and shape monodispersity) is based on the use of small-diameter uniform-sized gold particles as nucleation centers for the further growth of silver or gold layers.

A widely used approach involves citrate reduction of a gold salt to produce 12-20 nm size gold particles with a relatively narrow size distribution. The commonly used method for producing smaller gold particles was developed by Brust et al [Brust, M.; Walker, M.; Bethell, D.; Schiffrin, D. J; Whyman, R. *Chem. Commun.* 1994, 801]. This method is based on borohydride reduction of gold salt in the presence of an alkanethiol capping agent to produce 1-3 nm particles. Nanoparticle sizes can be controlled between 2 and 5 nm by varying the thiol concentration, [Hostetler, M. J; Wingate, J. E.; Zhong, C. J.; Harris, J. E.; Vachet, R. W.; Clark, M. R.; Londono, J. D.; Green, S. J; Stokes, J. J.; Wignall, G. D.; Glish, G. L.; Porter, M. D.; Evans, N. D.; Murray, R. W *Langmuir* 1998, 14, 17]. Phosphine-stabilized gold clusters have also been produced and subsequently converted to thiol-capped clusters by ligand exchange in order to improve their stability [Schmid, G.; Pfeil, R.; Boese, R.; Bandrmann, F.; Meyer, S.; Calis, G. H. M.; van der Velden, J. W. A. *Chem. Ber.* 1981, 114, 3634; Warner, M. G.; Reed, S. M.; Hutchison, J. E. *Chem. Mater.* 2000, 12, 3316.] and phosphine-stabilized monodispersed gold particles were prepared using a similar protocol to the Brust method [Weare, W. W.; Reed, S. M.; Warner, M. G.; Hutchison, J. E. *J. Am. Chem. Soc.* 2000, 122, 12890]. See also recent review: Ziyi Zhong, Benoit[1] Male, Keith B.[1] Luong, John H. T., *More Recent Progress in the Preparation of Au Nanostructures, Properties, and Applications, Analytical Letters;* 2003, Vol. 36 Issue 15, p 3097-3118]

Fabrication of Nanoparticle of Metal Coated with Nanoshells of Dyes

The fabrication of metal nanoparticles coated with nanoshells of dye molecules can be performed using the method described by Masuhara et al [AKITO MASUHARA_, SATOSHI OHHASHIy, HITOSHI KASAI, SHUJI OKADA, FABRICATION AND OPTICAL PROPERTIES OF NANOCOMPLEXES COMPOSED OF METAL NANOPARTICLES AND ORGANIC DYES, *Journal of Nonlinear Optical Physics & Materials* Vol. 13, Nos. 3 & 4 (2004) 587-592]. Nanocomplexes composed of Ag or Au as a core and 3-carboxlymethyl-5-[2-(3-octadecyl-2-benzoselenazolinylidene)ethylidene]rhodanine (MCSe) or copper (II) phthalocyanine (CuPc) as a shell are prepared by the co-reprecipitation method. In the case of Ag-MCSe nanocomplexes, 0.5 mM acetone solution of MCSe are injected into 10 ml of Ag nanoparticle water dispersion, prepared by the reduction of $AgNO_3$ using $NaBH_4$: Au-MCSe nanocomplexes are also fabricated in a similar manner. A water dispersion of Au nanoparticles was prepared by the reduction of $HAuCl_4$ using sodium citrate. Subsequently, 2 M $NH_4OH$ (50 µl) was added and the mixture was thermally treated at 50° C. This amine treatment often stimulates the J-aggregate formation of MCSe. 6 Ag—CuPc and Au—CuPc nanocomplexes were also fabricated in the same manner: 1 mM 1-methyl-2-pyrrolidinone (NMP) solution of CuPc (200 µl) was injected into a water dispersion (10 ml) of Ag or Au nanoparticles.

The present invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an autoimmune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Work in the area of photodynamic therapy has shown that the amount of singlet oxygen required to cause cell lysis, and thus cell death, is $0.32 \times 10^{-3}$ mol/liter or more, or 109 singlet oxygen molecules/cell or more. However, in one embodiment of the present invention, it is most preferable to avoid production of an amount of singlet oxygen that would cause cell lysis, due to its indiscriminate nature of attack, lysing both target cells and healthy cells. Accordingly, it is most preferred in the present invention that the level of singlet oxygen production caused by the initiation energy used or activatable pharmaceutical agent upon activation be less than level needed to cause cell lysis.

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy modulation agent and plasmonics compounds and structures, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, kit or dispenser together with instructions for administration.

Methods of administering agents according to the present invention are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection.

Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

It will also be understood that the order of administering the different agents is not particularly limited. Thus in some embodiments the activatable pharmaceutical agent may be administered before the energy modulation agent, while in other embodiments the energy modulation agent may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

An advantage of the methods of the present invention is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A.

The present invention methods can be used alone or in combination with other therapies for treatment of cell proliferation disorders. Additionally, the present invention methods can be used, if desired, in conjunction with recent advances in chronomedicine, such as that detailed in Giacchetti et al, *Journal of Clinical Oncology, Vol* 24, No 22 (August 1), 2006: pp. 3562-3569. In chronomedicine it has been found that cells suffering from certain types of disorders, such as cancer, respond better at certain times of the day than at others. Thus, chronomedicine could be used in conjunction with the present methods in order to augment the effect of the treatments of the present invention.

Another embodiment of the present invention is a computer-implemented system, comprising:

a central processing unit (CPU) having a storage medium on which is provided:

a database of excitable compounds;

a database of plasmonics-active agents;

a first computation module for identifying and designing an excitable compound that is capable of activation and of binding with a target cellular structure or component;

a second computation module predicting the resonance absorption energy of the excitable compound; and a third computation module predicting the plasmonics-enhanced spectroscopic properties of the plasmonics-active agents, wherein the system, upon selection of a target cellular structure or component, computes an excitable compound that is capable of activation and of binding with the target structure followed by a computation to predict the resonance absorption energy of the excitable compound and by a computation of the plasmonics-enhanced spectroscopic properties of the photonics-active agents.

The computer implemented system can further comprise an energy initiation source connected to the CPU, wherein after computation of the resonance absorption energy of the excitable compound and the plasmonics-enhanced spectroscopic properties of the photonics-active agents, the system directs the energy initiation source to provide the computed resonance absorption energy to the excitable compound. In such a computer implemented system, the plasmonics active agent is preferably a PEPST probe or EPEP probe.

In another aspect, the present invention further provides systems and kits for practicing the above described methods.

In one embodiment, a system in accordance with the present invention may include: (1) an initiation energy source; (2) one or more energy modulation agents; and (3) one or more activatable pharmaceutical agents.

In another embodiment, a system in accordance with the present invention may include an initiation energy source and one or more activatable pharmaceutical agents.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.).

In other embodiments, endoscopic or laparoscopic devices equipped with appropriate initiation energy emitter may be used as the initiation energy source. In such systems, the initiation energy may be navigated and positioned at the preselected coordinate to deliver the desired amount of initiation energy to the site.

In further embodiments, dose calculation and robotic manipulation devices may also be included in the system.

The reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, at least one plasmonics agent and containers suitable for storing the agents in stable form, and preferably further comprising instructions for administering the at least one activatable pharmaceutical agent, at least one plasmonics agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

Having generally described this invention, a further understanding can be obtained by reference to certain specific examples which are provided herein for purposes of illustration only and are not intended to be limiting unless otherwise specified.

EXAMPLES

Preparation of Silver Nanoparticles

Silver (or gold) colloids were prepared according to the standard Lee-Meisel method: 200 mL of $10^{-3}$ M $AgNO_3$ aqueous solution was boiled under vigorous stirring, then 5 mL of 35-mM sodium citrate solution were added and the resulting mixture was kept boiling for 1 h. This procedure was reported to yield ~$10^{11}$ particles/mL of homogenously sized colloidal particles with a diameter of ~35-50 nm and an absorption maximum at 390 nm. The colloidal solutions were stored at 4° C. and protected from room light. Further dilutions of the colloidal solutions were carried out using distilled water.

Fabrication/Preparation of Metal Nanocaps

One approach has involved the use of nanospheres spin-coated on a solid support in order to produce and control the desired roughness. The nanostructured support is subsequently covered with a layer of silver that provides the conduction electrons required for the surface plasmon mechanisms. Among the techniques based on solid substrates, the methods using simple nanomaterials, such as Teflon or latex nanospheres, appear to be the simplest to prepare. Teflon and latex nanospheres are commercially available in a wide variety of sizes. The shapes of these materials are very regular and their size can be selected for optimal enhancement. These materials comprise isolated dielectric nanospheres (30-nm diameter) coated with silver producing systems of half-nanoshells, referred to as nanocaps.

Figure 19:
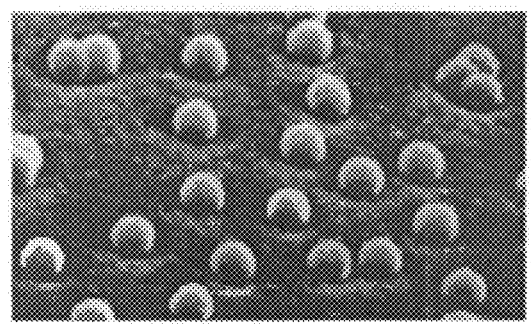
FIG. 19 is an photomicrograph showing nanocaps (half-nanoshells) comprising polystyrene nanospheres coated with silver.

FIG. 19 shows a scanning electron micrograph (SEM) of 300-nm diameter polymer nanospheres covered by a 100-nm thick silver nanocaps (half-nanoshell) coating. The nanoparticles can be sonicated to release them from the underlying substrate. The effect of the sphere size and metal layer thickness upon the SERS effect can be easily investigated. The silver coated nanospheres were found to be among the most plasmonics-active investigated. Gold can also be used instead of silver to coat over nanoparticles comprising PA drug molecules.

Fabrication of Gold Nanoshells

Gold nanoshells have been prepared using the method described by Hirsch et al. [Hirsch L R, Stafford R J, Bankson J A, Sershen S R, Price R E, Hazle J D, Halas N J, West J L (2003) Nanoshell-mediated near infrared thermal therapy of tumors under M R Guidance. Proc Natl Acad Sci 100:13549-13554] using a mechanism involving nucleation and then successive growth of gold nanoparticles around a silica dielectric core. Gold nanoparticles, the seed, prepared as described above using the Frens method, were used to grow the gold shell. Silica nanoparticles (100 nm) used for the core of the nanoshells were monodispersed in solution of 1% APTES in EtOH. The gold "seed" colloid synthesized using the Frens method were grown onto the surface of silica nanoparticles via molecular linkage of amine groups. The "seed" covers the aminated silica nanoparticle surface, first as a discontinuous gold metal layer gradually growing forming a continuous gold shell. Gold nanoparticles used as the "seed" were characterized using optical transmission spectroscopy (UV-Vis Spectrophotometer, Beckman Coulter, Fullerton, Calif.) and atomic force microscopy (Atomic Force Microscope, Veeco Instruments, Woodbury, N.Y.) while gold nanoshells were characterized using optical transmission spectroscopy and scanning electron microscopy (Scanning Electron Microscope, Hitachi S-4700, Hitachi High Technologies America, Inc. Pleasanton, N.Y.).

Probe for Measurement of Apoptosis with the PDT Drug ALA

A method has been developed using nanosensors that can be used to evaluate the effectiveness of PEPST probes. Although one can use conventional methods (not requiring nanosensors), we describe the nanosensor method previously developed [P. M. Kasili, J M. Song, and T Vo-Dinh, "*Optical Sensor for the Detection of Caspase-9 Activity in a Single Cell*", J. Am. Chem. Soc., 126, 2799-2806 (2004)]. The method comprises measuring caspases activated by apoptosis induced by the photoactive drugs. In this experiment, we measure two sets of cells I and II. Set I is treated with the drug ALA and set II is treated by the drug ALA conjugated to a PEPST probe described in the previous section. By comparing the results (amount of Caspases detected), one can evaluate the efficiency of the PEPST-ALA drug compared to ALA alone.

In the classical model of apoptosis, caspases are divided into initiator caspases and effector caspases according to their function and their sequence of activation. Initiator caspases include caspase-8, -9, while effector caspases include, caspases-3, -6 and -7. The activation of caspases is one of the earliest biomarkers of apoptosis making caspases an early and ideal target for measuring apoptosis. Apoptosis, or programmed cell death, is a mode of cell death characterized by specific morphological and biochemical features. The results obtained in these experiments can be used to evaluate the effectiveness of phototherapeutic drugs that induce apoptosis (e.g. PDT drugs). Since caspases play a central role in the induction of apoptosis, tetrapeptide-based optical nanosensors were used to determine their role in response to a photodynamic therapy (PDT) agent, δ-aminolevulinic acid (ALA) in the well-characterized human breast carcinoma cell line, MCF-7. MCF-7 cells were exposed to the photosensitizer ALA to explore ALA-PDT induced apoptosis by monitoring caspase-9 and caspase-7 activity. Caspase-9 and caspase-7 protease activity was assessed in single living MCF-7 cells with the known caspase-9 and caspase-7 substrates, Leucine-aspartic-histidine-glutamic acid 7-amino-4-methylcoumarin (LEHD-AMC) and aspartic-glutamic acid-valine-aspartic acid 7-amino-4-methylcoumarin (DEVD-AMC) respectively, covalently immobilized to the nanotips of optical nanosensors. Upon the induction of apoptosis, activated target caspases recognize the tetrapeptide sequence and specifically cleaves it. The recognition of substrate by caspases is immediately followed by a cleavage reaction yielding the fluorescent AMC which can be excited with a Helium-Cadmium (HeCd) laser to generate a measurable fluorescence signal. By comparing the fluorescence signal generated from AMC within cells with activated caspases and from those with inactive caspases, we are able to successfully detect caspase activity within a single living MCF-7 cell.

Chemicals and Reagents

δ-aminolevulinic acid (ALA), phosphate buffered saline (PBS), hydrochloric acid (HCl), nitric acid ($HNO_3$), Glycidoxypropyltrimethoxysilane (GOPS), 1,1'-Carbonyldiimidazole (CDI), and anhydrous acetonitrile were purchased from Sigma-Aldrich, St. Louis, Mo. Caspase-9 substrate, LEHD-7-amino-4-methylcoumarin (AMC), Caspase-7 substrate, DEVD-7-amino-4-methylcoumarin (AMC), 2× reaction buffer, dithiothreitol (DTT), and dimethylsulfoxide (DMSO) were purchased from BD Biosciences, Palo Alto. Calif.

Cell Lines

Human breast cancer cell line, MCF-7, was obtained from American Type Culture Collection (Rockville, Md., USA, Cat-no. HTB22). MCF-7 cells were grown in Dulbecco's Modified Eagle's Medium ((DMEM) (Mediatech, Inc., Herndon, Va.)) supplemented with 1 mM L-glutamine (Gibco, Grand Island, N.Y.) and 10% fetal bovine serum (Gibco, Grand Island, N.Y.). Cell culture was established in growth medium (described above) in standard T25 tissue culture flasks (Corning, Corning, N.Y.). The flasks were incubated in a humidified incubator at 37° C., 5% $CO_2$ and 86% humidity. Cell growth was monitored daily by microscopic observation until a 60-70% state of confluence was achieved. The growth conditions were chosen so that the cells would be in log phase growth during photosensitizer treatment with ALA, but would not be so close to confluence that a confluent monolayer would form by the termination of the chemical exposure. In preparation for experiments, cells were harvested from the T25 flasks and 0.1 ml ($10^5$ cells/ml) aliquots were seeded into 60 mm tissue culture dishes (Corning Costar Corp., Corning, N.Y.) for overnight attachment. The MCF-7 cells were studied as four separate groups with the first group, Group I, being the experimental, exposed to 0.5 mM ALA for 3 h followed by photoactivation ([+]ALA[+]PDT). This involved incubating the cells at 37° C. in 5% $CO_2$ for 3 h with 0.5 mM ALA. Following incubation the MCF-7 cells were exposed to red light from a HeNe laser ($\lambda$632.8 nm, <15 mW, Melles Griot, Carlsbad, Calif.) positioned about 5.0 cm above the cells for five minutes at a fluence of 5.0 mJ/cm$^2$ to photoactivate ALA and subsequently induce apoptosis. The second and third groups, Group II and III respectively, served as the "treated control" and were exposed to 0.5 mM ALA for 3 hours without photoactivation ([+]ALA[−]PDT) and photoactivation without 0.5 mM ALA ([−]ALA[+]PDT) respectively. The fourth group, Group IV was the "untreated control," which received neither ALA nor photoactivation ([−]ALA[−]PDT Experimental Protocol Preparation of Enzyme Substrate-Based Optical Nanosensors Briefly, this process involved cutting and polishing plastic clad silica (PCS) fibers with a 600-μm-size core (Fiberguide Industries, Stirling, N.J.). The fibers were pulled to a final tip diameter of 50 nm and then coated with ~100 nm of silver metal (99.999% pure) using a thermal evaporation deposition system (Cooke Vacuum Products, South Norwalk, Conn.) achieving a final diameter of 150 nm. The fused silica nanotips were acid-cleaned ($HNO_3$) followed by several rinses with distilled water. Finally, the optical nanofibers were allowed to air dry at room temperature in a dust free environment. The nanotips were then silanized and treated with an organic coupling agent, 10% Glycidoxypropyltrimethoxysilane (GOPS) in distilled water. The silanization agent covalently binds to the silica surface of the nanotips modifying the hydroxyl group to a terminus that is compatible with the organic cross-linking reagent, 1'1, Carbonyldiimidazole (CDI). The use of CDI for activation introducing an imidazole-terminal group was particularly attractive since the protein to be immobilized could be used without chemical modification. Proteins bound using this procedure remained securely immobilized during washing or subsequent manipulations in immunoassay procedures, as opposed to procedures that use adsorption to attach proteins. The silanized and activated nanotips for measuring caspase-9 activity were immersed in a solution containing DMSO, 2× reaction buffer, PBS, and LEHD-AMC, and allowed to incubate for 3 h at 37° C., while those for measuring caspase-7 activity were immersed in a solution containing DMSO, 2× reaction buffer, PBS, and DEVD-AMC, and allowed to incubate for 3 h at 37° C.

Measurement System and Procedure

A schematic representation of the experimental setup used in this work is described in a previous work [[P.M. Kasili, J. M. Song, and T. Vo-Dinh, "*Optical Sensor for the Detection of Caspase-9 Activity in a Single Cell*", J. Am. Chem. Soc., 126, 2799-2806 (2004)]. The components included a HeCd laser (Omnichrome, <5 mW laser power) for excitation, an optical fiber for delivery of excitation light to the optical nanosensor, a Nikon Diaphot 300 inverted fluorescence microscope (Nikon, Inc., Melville, N.Y.), a photon counting photomultiplier tube (PMT) and a PC for data acquisition and processing. This experimental set-up, used to probe single cells, was adapted for this purpose from a standard micromanipulation and microinjection apparatus. The Nikon Diaphot 300 inverted microscope was equipped with a Diaphot 300/Diaphot 200 Incubator to maintain the cell cultures at 37° C. on the microscope stage, during these experiments. The micromanipulation equipment consisted of MN-2 (Narishige Co. Ltd., Tokyo, Japan) Narishige three-dimensional manipulators for coarse adjustment, and Narishige MMW-23 three-dimensional hydraulic micromanipulators for fine adjustments. The optical nanosensor was mounted on a micropipette holder (World Precision Instruments, Inc., Sarasota, Fla.). The 325 nm laser line of a HeCd laser was focused onto a 600-μm-delivery fiber that is terminated with a subminiature A (SMA) connector. The enzyme substrate-based optical nanosensor was coupled to the delivery fiber through the SMA connector and secured to the Nikon inverted microscope with micromanipulators. To record the fluorescence generated by AMC molecules at the nanotips, a Hamamatsu PMT detector assembly (HC125-2) was mounted in the front port of the Diaphot 300 microscope. The fluorescence emitted by AMC from the measurement made using single live cells was collected by the microscope objective and passed through a 330-380 nm filter set and then focused onto a PMT for detection. The output from the PMT was recorded using a universal counter interfaced to a personal computer (PC) for data treatment and processing.

In Vitro Determination of Caspase Activity

After incubation using the following treatment groups, group (I)—[+]ALA[+]PDT, group II—[+]ALA[−]PDT, group III—[−]ALA[+]PDT, and group IV—[−]ALA[−]PDT, MCF-7 cells were washed with PBS solution, pH 7.4, and then resuspended in lysis buffer (100 mM HEPES, pH 7.4, 10% sucrose, 0.1% 3-[(3-cholamidopropyl)-dimethylammonio]-1-propanesulfonate (CHAPS), 1 mM EDTA, 10 mM dithiothreitol (DTT), 1 mM phenylmethylsulphonyl fluoride (PMSF), 10 mg/ml pepstatin, 10 mg/ml leupeptin) and left on ice for 45 minutes. The cells were then repeatedly passed through a syringe with a 25-gauge needle until most of the cell membrane was disrupted, and centrifuged at 1500 RPM for 10 min. Activity of caspases was measured using the fluorogenic substrate peptides; LEHD-AMC for caspase-9 and DEVD-AMC for caspase-7. The release of AMC was measured after incubating optical nanosensors in picofuge tubes containing the cell lysates from the various treatment groups and using a HeCd laser (excitation 325 nm) to excite AMC. Caspase activity was expressed as fluorescence intensity of AMC as a function of equivalent nanomoles of LEHD-AMC and DEVD-AMC respectively.

The results of the in vitro measurement of caspase-9 and caspase-7 activity were plotted. The curves for each fluorescent measurement of AMC were plotted for each as a function of AMC concentration. Caspase-9 activity was determined by incubation of optical nanosensors with the substrate LEHD-7-amino-4-methylcoumarin (AMC) in cell lysate (~$10^5$ cells) obtained from the following treatment groups; group I, II, I and IV, described earlier in the article. The release of AMC was measured after excitation using HeCd laser (325 nm) and collecting the fluorescence signal using a 380 nm longpass filter. The peak emission wavelength of AMC is about 440 nm. Likewise, Caspase-7 activity was determined by incubation in cell lysate (~$10^5$ cells) obtained from the following treatment groups I, II, III, and IV. The release of AMC was measured after excitation using a HeCd laser (325 nm) and collecting the fluorescence signal using a 380 nm longpass filter.

In this experiment, we measure two sets of cells I and II: (1) Set I is treated with the drug ALA and (2) set II is treated by the drug ALA conjugated to a PEPST probe described in the previous section. By comparing the results (amount of caspase detected), one can evaluate the efficiency of the PEPST-ALA drug compared to ALA alone.

Additional modifications and variations of the present invention are possible in light of the above teachings. It is therefore to be understood that within the scope of the appended claims, the invention may be practiced otherwise than as specifically described herein.

The invention claimed is:

1. A pharmaceutical composition for treating cancer, comprising:
    at least one activatable pharmaceutical agent capable of activation and of causing non-lytic cancer cell death upon activation, wherein the at least one activatable pharmaceutical agent is a psoralen or a coumarin;
    at least one plasmonics-active agent capable of enhancing or modifying energy, wherein the at least one plasmonics-active agent is at least one member selected from the group consisting of gold, silver, platinum, palladium, nickel, ruthenium, rhenium, copper, and cobalt;
    at least one energy modulation agent capable of activating the at least one activatable pharmaceutical agent when energized, wherein the at least one energy modulation agent is at least one member selected from the group consisting of CdS, CsCl, ZnS, $Er^{3+}$ doped $BaTiO_3$, $Yb^{3+}$ doped $CsMnCl_3$, CdTe, CdSe, ZnO, CdS, $Y_2O_3$, MgS, CaS, SrS, BaS, $BaF_2$, BaFBr, $BaTiO_3$, ZnS:Mn,Er; ZnSe:Mn,Er; MgS:Mn,Er; CaS:Mn,Er; ZnS:Mn,Yb; ZnSe:Mn,Yb; MgS:Mn,Yb; CaS:Mn,Yb; ZnS:$Tb^{3+}$, $Er^{3+}$; ZnS:$Tb^{3+}$; $Y_2O_3$:$Tb^{3+}$; $Y_2O_3$:$Tb^{3+}$, $Er3^+$; ZnS:$Mn^{2+}$; and ZnS:Mn,$Er^{3+}$; and
    a pharmaceutically acceptable carrier,
    wherein the pharmaceutical composition is in a form of a plasmonics enhanced photospectral therapy (PEPST) probe comprising (a) the at least one plasmonics active agent as a plasmonics active metal nanoparticle, (b) the at least one activatable pharmaceutical agent, and (c) the at least one energy modulation agent, and has a configuration selected from the following:
    the at least one activatable pharmaceutical agent bound to the at least one energy modulation agent, which is bound to the at least one plasmonics active metal nanoparticle;
    the at least one plasmonics active metal nanoparticle having a nanocap formed of the at least one energy modulation agent, wherein the nanocap has attached thereto molecules of the at least one activatable pharmaceutical agent;
    nanoparticles of the at least one energy modulation agent having on a surface thereof a mixture of the at least one plasmonics active metal nanoparticles and the at least one activatable pharmaceutical agent;
    nanoparticles of the at least one energy modulation agent having a nanocap formed of the at least one plasmonics active metal nanoparticle, wherein the nanoparticles of the at least one energy modulation agent also have on a surface thereof molecules of the at least one activatable pharmaceutical agent;
    a core formed from the at least one plasmonics active metal nanoparticle having a nanoshell formed of the at least one energy modulation agent, wherein the nanoshell has on a surface thereof molecules of the at least one activatable pharmaceutical agent; or
    at least one nanoparticle of the at least one plasmonics active metal nanoparticle attached to at least one nanoparticle of the at least one energy modulation agent, wherein the at least one nanoparticle of the at least one energy modulation agent has the at least one activatable pharmaceutical agent attached thereto by a detachable biochemical bond.

2. The pharmaceutical composition of claim 1, wherein the at least one activatable pharmaceutical agent is 8-methoxypsoralen (8-MOP) or 4'-aminomethyl-4,5',8 -trimethylpsoralen (AMT).

3. The pharmaceutical composition of claim 1, wherein the non-lytic cell death is apoptosis in a target cell.

4. The pharmaceutical composition of claim 1, wherein said at least one energy modulation agent is a single energy modulation agent, and is coupled to said at least one activatable pharmaceutical agent.

5. The pharmaceutical composition of claim 1, wherein the PEPST probe has a configuration wherein the core is formed from the at least one plasmonics active metal nanoparticle having the nanoshell formed of the at least one energy modulation agent, wherein the nanoshell has molecules of the at least one activatable pharmaceutical agent bound to the surface thereof.

6. The pharmaceutical composition of claim 5, wherein the at least one plasmonics active metal nanoparticle is a gold nanoparticle and the at least one energy modulation agent is $Y_2O_3$.

7. The pharmaceutical composition of claim 1, wherein the at least one plasmonics active agent is gold, the at least one energy modulation agent is $Y_2O_3$, and the at least one pharmaceutical agent is 8-methoxypsoralen (8-MOP).

8. A pharmaceutical composition for treating cancer, comprising:
- at least one activatable pharmaceutical agent capable of activation and of causing non-lytic cancer cell death upon activation, wherein the at least one activatable pharmaceutical agent is 8-methoxypsoralen (8-MOP);
- at least one plasmonics-active agent capable of enhancing or modifying energy, wherein the at least one plasmonics-active agent comprises gold;
- at least one energy modulation agent capable of activating the at least one activatable pharmaceutical agent when energized, wherein the at least one energy modulation agent comprises $Y_2O_3$; and
- a pharmaceutically acceptable carrier.

9. The pharmaceutical composition of claim 8, wherein the non-lytic cell death is apoptosis in a target cell.

10. The pharmaceutical composition of claim 8, wherein said at least one energy modulation agent is a single energy modulation agent, and is coupled to said at least one activatable pharmaceutical agent.

\* \* \* \* \*

UNITED STATES PATENT AND TRADEMARK OFFICE
CERTIFICATE OF CORRECTION

PATENT NO. : 8,951,561 B2  
APPLICATION NO. : 12/389946  
DATED : February 10, 2015  
INVENTOR(S) : Tuan Vo Dinh et al.

Page 1 of 1

It is certified that error appears in the above-identified patent and that said Letters Patent is hereby corrected as shown below:

In the specification,

Column 8, line 46, "oxygen" should read --oxygen.--

Column 9, line 40, "Corner" should read --Comer--

Column 25, line 63, "molecules" should read --molecules.--

Column 25, line 67, "molecues" should read --molecules.--

Column 26, line 3, "nanoparticles" should read --nanoparticles.--

Column 26, lines 7-8, "nanoparticles" should read --nanoparticles.--

Column 26, line 10, "molecule" should read --molecule.--

Column 32, line 3, "Heme" should read --Herne--

Column 32, line 4, "Heme" should read --Herne--

Column 39, line 8, "Mark R. Antonioc" should read --Mark R. Antonio--

Column 43, line 44, "[002]-9258]" should read --[0021-9258]--

Column 51, line 65, "SATOSHI OHHASHIy" should read --SATOSHI OHHASHI--

Signed and Sealed this  
Twenty-third Day of February, 2016

Michelle K. Lee  
*Director of the United States Patent and Trademark Office*